(12) United States Patent
Lee et al.

(10) Patent No.: US 8,471,043 B2
(45) Date of Patent: Jun. 25, 2013

(54) PLATENSIMYCIN DERIVATIVES, THEIR INTERMEDIATES, AND PROCESS FOR PREPARING THE SAME, AND NEW PROCESS FOR PREPARING PLATENSIMYCIN

(75) Inventors: Eun Lee, Seoul (KR); Ki Po Jang, Seoul (KR); Chan Hyuk Kim, Seoul (KR); Seong Wook Na, Cheongju-si (KR); Dong Seok Jang, Seoul (KR)

(73) Assignee: SNU R&DB Foundation, Seoul (KR)

( * ) Notice: Subject to any disclaimer, the term of this patent is extended or adjusted under 35 U.S.C. 154(b) by 442 days.

(21) Appl. No.: 12/936,856

(22) PCT Filed: Mar. 31, 2009

(86) PCT No.: PCT/KR2009/001618
§ 371 (c)(1),
(2), (4) Date: Oct. 7, 2010

(87) PCT Pub. No.: WO2009/125938
PCT Pub. Date: Oct. 15, 2009

(65) Prior Publication Data
US 2011/0028741 A1 Feb. 3, 2011

(30) Foreign Application Priority Data

Apr. 8, 2008 (KR) .......................... 10-2008-0032713
Dec. 12, 2008 (KR) .......................... 10-2008-0126506

(51) Int. Cl.
*C07D 493/08* (2006.01)
*C07C 245/14* (2006.01)

(52) U.S. Cl.
USPC ............................ 549/383; 549/386; 534/564

(58) Field of Classification Search
USPC .................................. 549/383, 386; 534/564
See application file for complete search history.

(56) References Cited

U.S. PATENT DOCUMENTS 7,745,644 B2 * 6/2010 Basilio et al. ................. 549/212

FOREIGN PATENT DOCUMENTS

WO 2005009391 A2 2/2005

OTHER PUBLICATIONS

Tiefenbacher et al., "Synthesis of Platensimycin," Angewandte Chemie, 2008, pp. 2548-2555, 47.
Zou et al., "Formal Synthesis of (±)-Platensimycin," Organic Letters, 2007, pp. 1825-1828, vol. 9, No. 9.
Nicolaou et al., "Adamantaplatensimycin: A Bioactive Analogue of Platensimycin," Angewandte Chemie, 2007, pp. 4712-4714, 46.

* cited by examiner

*Primary Examiner* — Bernard Dentz
(74) *Attorney, Agent, or Firm* — The Webb Law Firm

(57) ABSTRACT

The present invention relates to novel platensimycin derivatives, their intermediates and preparing methods of the same. Platensimycin is known as an effective antibiotic material having a broad antimicrobial spectrum and its derivatives are also expected to be effective antibiotic candidates. The present invention also relates to a novel preparing method of platensimycin. The intermediates used for the production of platensimycin and its derivatives of the present invention are tricyclo ketone derivatives and tetracyclo derivatives. Tetracyclo derivatives are prepared from tricyclo ketone derivatives prepared by carbonyl ylide [3+2] cycloaddition of diazoketone derivative.

12 Claims, No Drawings

PLATENSIMYCIN DERIVATIVES, THEIR INTERMEDIATES, AND PROCESS FOR PREPARING THE SAME, AND NEW PROCESS FOR PREPARING PLATENSIMYCIN

TECHNICAL FIELD

The present invention relates to novel platensimycin derivatives represented by formula 1 and a preparing method of the same. The present invention also relates to a novel preparing method of platensimycin. Platensimycin is known as a useful antibiotic having a wide antimicrobial spectrum and its derivatives are also expected to be useful antibiotics.

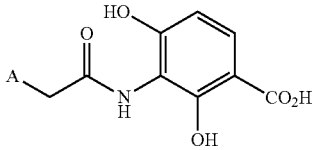

[Formula 1]

[In formula 1, A is

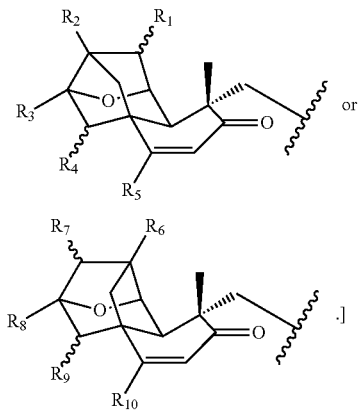

.]

The present invention relates to intermediates for the production of platensimycin and its derivatives and a preparing method of the same, more precisely tricyclo ketone derivatives represented by formula 10 or formula 24 and a preparing method of the same and a preparing method of tetracyclo derivatives represented by formula 4 or formula 19. Tricyclo ketone derivatives are produced from diazoketone derivatives via carbonyl ylide [3+2] cycloaddition reaction. Tetracyclo derivatives are important intermediates for the production of platensimycin and its derivatives, which are produced from tricyclo ketone derivatives, the starting material.

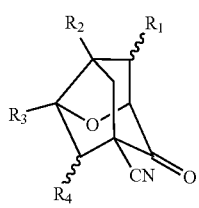

[Formula 10]

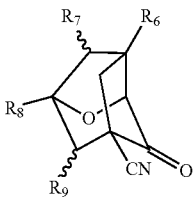

[Formula 24]

[In formula 10 and formula 24, $R_1$ and $R_6$ are independently H, (C1-C10)alkyl, iodo, bromo or chloro; $R_2$, $R_3$, $R_7$, and $R_8$ are independently H, (C1-C10)alkyl or (C6-C20) aryl; $R_4$ and $R_9$ are independently H, (C1-C10)alkyl, (C6-C20) aryl or (C6-C20) aryl (C1-C10)alkyl.]

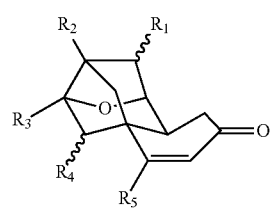

[Formula 4]

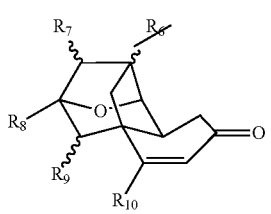

[Formula 19]

[In formula 4 and formula 19, $R_1$ and $R_6$ are independently H, (C1-C10)alkyl, iodo, bromo or chloro; $R_2$, $R_3$, $R_5$, $R_7$, $R_8$ and $R_{10}$ are independently H, (C1-C10)alkyl or (C6-C20) aryl; $R_4$ and $R_9$ are independently H, (C1-C10)alkyl, (C6-C20) aryl or (C6-C20) aryl(C1-C10)alkyl.]

BACKGROUND ART

Platensimycin is a novel antibiotic having a wide antimicrobial spectrum, which has been isolated from *Streptomyces platensis*, a kind of fungi found in the soil of South Africa by Merck Co., USA.

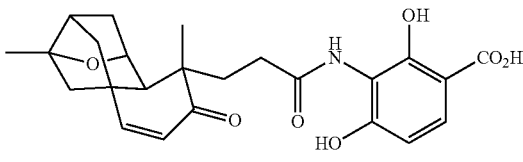

platensimycin

In the past decades, novel antibiotics kept being discovered from nature and in the laboratory. But human defense system against infection has been consistently compromised. Microbes keep developing resistance against the conventional antibiotics. Multi-drug resistant bacteria bring serious infection problems; and particularly hospital acquired (nosocomial) infection is more serious. In-patients are weak, and they are more easily infected. Once they are infected, it is very difficult to treat the infection with drugs and it might even result in death.

Therefore, development of new drugs having completely different physiological mechanisms to attack pathogens is required. Platensimycin isolated from the fungus *Streptomyces platensis* is one of them.

Platensimycin is a selective intracellular lipid synthesis inhibitor, which works on β-ketoacyl-(acyl-carrier-protein (ACP)) synthase I/II (FabF/B) to inhibit lipid synthesis. It was confirmed from the X-ray crystallographic studies that platensimycin targets the modified structure resulted from acylation of the lipogenic enzyme FabF/B. The mechanism of platensimycin is different from those of the conventional antibiotics being used clinically.

In the laboratory, chemists try to establish total synthesis routes to new compounds. In total synthesis, a complex compound is prepared from simple materials by using organic chemistry knowledge. For development of a new drug from a natural substance, investigation of structure-activity correlation is necessary. And then synthetic routes should be found for large scale preparation of the final target compound from less expensive starting materials. Total synthesis of platensimycin was first accomplished by Prof. Nicolau's research team at the Scripps Research Institute.

Platensimycin inhibits fatty acid synthesis in bacteria, and it possesses a broad spectrum antimicrobial activity against Gram-positive bacteria including methicillin-resistant *Staphylococcus aureus* (MRSA) and vancomycin-resistant *Enterococcus* (VRE).

Platensimycin derivatives may be designed by introducing different substituents in the backbone of platensimycin itself. They are good candidates as promising antibiotics by inhibiting fatty acid synthesis in bacteria. A good scheme for efficient total synthesis of platensimycin should also allow facile preparation of wide variety platensimycin derivatives for bioassay.

DISCLOSURE OF INVENTION

Technical Problem

The present invention relates to novel platensimycin derivatives represented by formula 1 and a preparing method of the same. The present invention also relates to a novel preparing method of platensimycin. Platensimycin is known to have a broad antimicrobial spectrum, so that it has been known as an effective antibiotic material. And thus, its derivatives are also expected to be effective antibiotic candidates.

Platensimycin derivatives represented by formula 1 include those platensimycin derivatives retaining backbone structure of the informed platensimycin but having diverse substituents introduced therein and isoplatensimycin and its derivatives maintaining backbone structure of the said platensimycin.

[Formula 1]

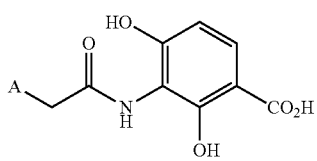

[In formula 1, A is

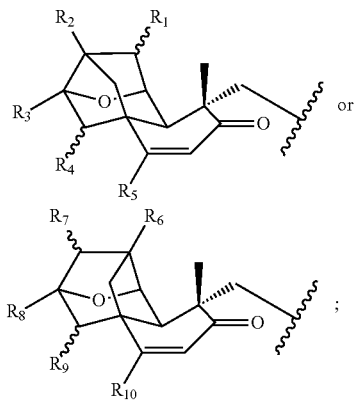

$R_1$ and $R_6$ are independently H, (C1-C10)alkyl, iodo, bromo or chloro;

$R_2$, $R_3$, $R_5$, $R_7$, $R_8$ and $R_{10}$ are independently H, (C1-C10)alkyl or (C6-C20) aryl;

$R_4$ and $R_9$ are independently H, (C1-C10)alkyl, (C6-C20) aryl or (C6-C20) aryl (C1-C10)alkyl;

But, it is excluded that $R_1=R_2=R_4=R_5=H$ and $R_3$=methyl.]

The present invention includes novel platensimycin derivatives represented by formula 2 and novel isoplatensimycin and its derivatives represented by formula 3.

[Formula 2]

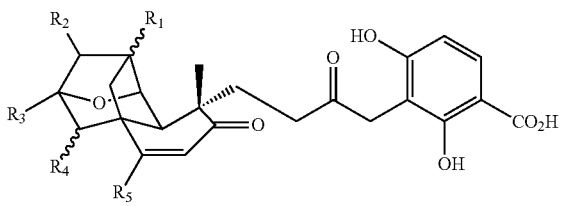

[$R_1$ is H, methyl, ethyl, n-propyl, i-propyl, n-butyl, i-butyl, t-butyl, iodo, bromo or chloro; $R_2$, $R_3$ and $R_5$ are independently H, methyl, ethyl, n-propyl, i-propyl, n-butyl, i-butyl, t-butyl or phenyl; $R_4$ is H, methyl, ethyl, n-propyl, i-propyl, n-butyl, i-butyl, t-butyl, phenyl or benzyl; but, it is excluded that $R_1=R_2=R_4=R_5=H$ and $R_3$=methyl.]

[Formula 3]

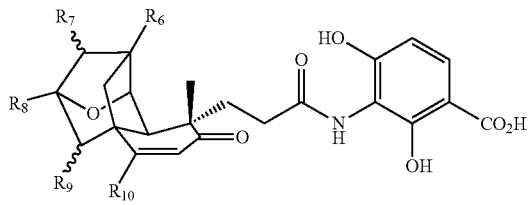

[$R_6$ is H, methyl, ethyl, n-propyl, i-propyl, n-butyl, i-butyl, t-butyl, iodo, bromo or chloro; $R_7$, $R_8$ and $R_{10}$ are independently H, methyl, ethyl, n-propyl, i-propyl, n-butyl, i-butyl, t-butyl or phenyl; $R_9$ is H, methyl, ethyl, n-propyl, i-propyl, n-butyl, i-butyl, t-butyl, phenyl or benzyl.]

In formula 2, $R_1$ is H, methyl, ethyl, n-propyl, i-propyl, n-butyl, i-butyl, t-butyl, iodo, bromo or chloro; $R_2$ is H or phenyl; $R_3$ is H, methyl, ethyl, n-propyl, i-propyl, n-butyl, i-butyl, t-butyl or phenyl; $R_4$ is H; $R_5$ is H, methyl, ethyl, n-propyl, i-propyl, n-butyl, i-butyl, t-butyl or phenyl; but, it is excluded that $R_1=R_2=R_4=R_5=H$ and $R_3=$methyl.

In formula 3, $R_6$ is H, methyl, ethyl, n-propyl, i-propyl, n-butyl, i-butyl, t-butyl, iodo, bromo or chloro; $R_7$ is H or phenyl; $R_8$ is methyl, ethyl, n-propyl, i-propyl, n-butyl, i-butyl or t-butyl; $R_9$ and $R_{10}$ are independently H.

Platensimycin and its derivatives represented by formula 2 are prepared by the following steps:

1) reacting enone derivative represented by formula 5 and acrylonitrile, leading to cyanoethylation to give enone derivative represented by formula 6;

2) hydrolyzing enone derivative represented by formula 6 to give carboxylic acid derivative represented by formula 7;

3) reacting carboxylic acid derivative represented by formula 7 and aniline derivative represented by formula 8, leading to amidation to give ester compound represented by formula 9; and 4) de-protecting the protection group of ester compound represented by formula 9 by using TASF reagent [$((CH_3)_2N)_3S]^+[F_2Si(CH_3)_3]^-$ to give platensimycin and its derivatives represented by formula 2.

[Formula 2]

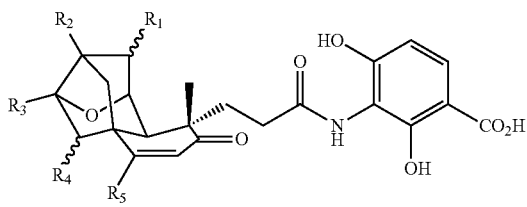

[Formula 5]

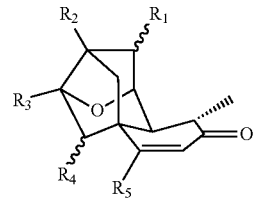

[Formula 6]

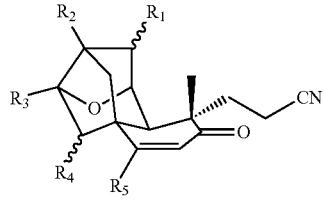

[Formula 7]

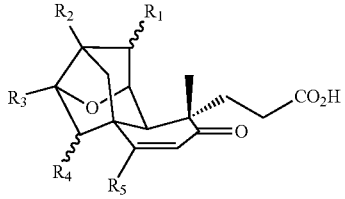

[Formula 8]

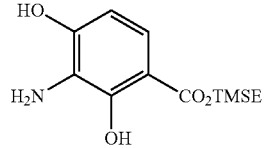

[Formula 9]

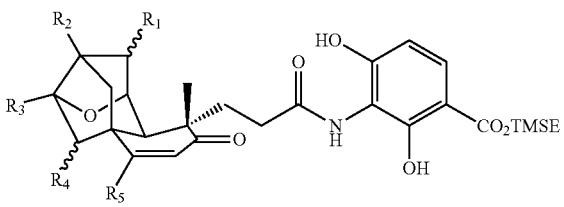

[In formulas 2, 5, 6, 7 and 9, $R_1$ is H, (C1-C10)alkyl, iodo, bromo or chloro; $R_2$, $R_3$ and $R_5$ are independently H, (C1-C10)alkyl or (C6-C20)aryl; $R_4$ is H, (C1-C10)alkyl, (C6-C20)aryl or (C6-C20)aryl(C1-C10)alkyl.]

When the substituent $R_5$ of enone derivative represented by formula 5 is H, the compound is prepared by the following steps:

5-1) reacting tricyclo ketone derivative represented by formula 10 and dimethyl 2-oxopropylphosphonate to give enone compound represented by formula 11;

6-1) inducing hydrosilylation of enone compound represented by formula 11 in the presence of ruthenium (I) catalyst, which is reduced into diisobutylaluminum hydride or diisopropylaluminum hydride, followed by hydrolysis to give ketoaldehyde compound represented by formula 12;

7-1) inducing intramolecular condensation of ketoaldehyde compound represented by formula 12 to give tetracyclo derivative represented by formula 4; and 8-1) inducing methylation of tetracyclo derivative represented by formula 4 to give enone derivative represented by formula 5.

[Formula 5]

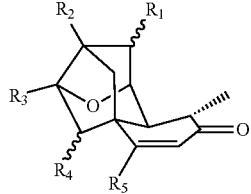

[Formula 10]

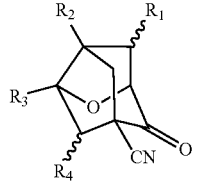

[Formula 11]

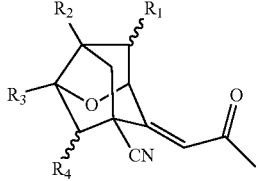

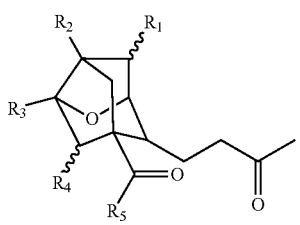

[Formula 12]

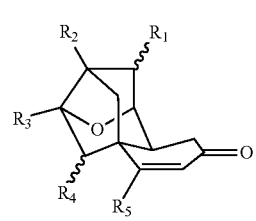

[Formula 4]

[In formulas 4, 5, 10, 11 and 12, $R_1$ is H, (C1-C10)alkyl, iodo, bromo or chloro; $R_2$ and $R_3$ are independently H, (C1-C10)alkyl or (C6-C20)aryl; $R_4$ is H, (C1-C10)alkyl, (C6-C20)aryl or (C6-C20)aryl(C1-C10)alkyl; $R_5$ is H.]

When the substituent $R_5$ of enone derivative represented by formula 5 is (C1-C10)alkyl or (C6-C20)aryl, the compound is prepared by the following steps:

5-2) reacting tricyclo ketone derivative represented by formula 10 and dimethyl 2-oxopropylphosphonate to give enone compound represented by formula 11;

6-2) inducing hydrosilylation of enone compound represented by formula 11 in the presence of ruthenium(I) catalyst, to which organic lithium ($R_5$—Li; $R_5$=(C1-C10)alkyl or (C6-C20)aryl) is added, followed by hydrolysis to give diketone compound represented by formula 12;

7-2) inducing intramolecular condensation of diketone compound represented by formula 12 to give tetracyclo derivative represented by formula 4; and 8-2) inducing methylation of tetracyclo derivative represented by formula 5.

[Formula 5]

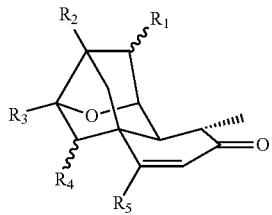

[Formula 10]

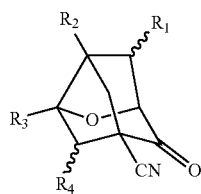

[Formula 11]

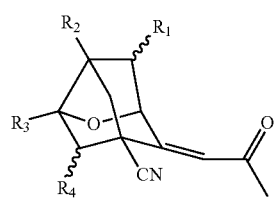

[Formula 12]

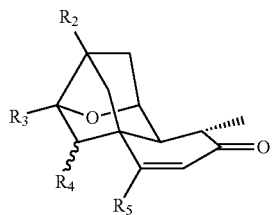

[Formula 4]

[In formulas 4, 5, 10, 11 and 12, $R_1$ is H, (C1-C10)alkyl, iodo, bromo or chloro; $R_2$, and $R_3$ are independently H, (C1-C10)alkyl or (C6-C20)aryl; $R_4$ is H, (C1-C10)alkyl, (C6-C20)aryl or (C6-C20)aryl(C1-C10)alkyl; $R_5$ is (C1-C10)alkyl or (C6-C20)aryl.]

Enone derivative represented by formula 5 can be prepared by the following steps:

5-1) inducing dehalogenation of tricyclo ketone derivative represented by formula 10 to give the compound represented by formula 10-1;

5-2) reacting the compound represented by formula 10-1 with dimethyl 2-oxopropylphosphonate to give enone compound represented by formula 11-1;

6) inducing hydrosilylation of the compound represented by formula 10-1 in the presence of ruthenium(I) catalyst, followed by reducing thereof to diisobutylaluminum hydride or diisopropylaluminum hydride, or reacting the said compound with organic lithium (R5-Li; R5=(C1-C10)alkyl or (C6-C20)aryl), followed by hydrolyzing thereof to give the compound represented by formula 12-1;

7) inducing intramolecular condensation of the compound represented by formula 12-1 to give tetracyclo derivative represented by formula 4-1; and 8) inducing methylation of tetracyclo derivative represented by formula 4-1 to give enone derivative represented by formula 5-1.

[Formula 5-1]

-continued

[Formula 10]

[Formula 10-1]

[Formula 11-1]

[Formula 12-1]

[Formula 4-1]

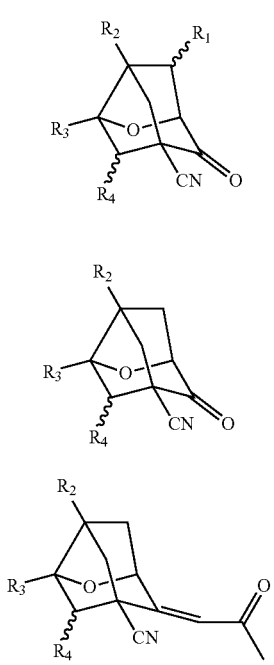

[In formulas 4-1, 5-1, 10, 10-1, 11-1 and 12-1, $R_1$ is iodo, bromo or chloro; $R_2$, $R_3$ and $R_5$ are independently H, (C1-C10)alkyl or (C6-C20)aryl; $R_4$ is H, (C1-C10)alkyl, (C6-C20)aryl or (C6-C20)aryl(C1-C10)alkyl.]

When the substituent $R_5$ of enone derivative represented by formula 6 is H, which is used as the starting material, the substituent $R_5$ of enone derivative represented by formula 6 can be substituted with (C1-C10)alkyl or (C6-C20)aryl by the following steps:

9) reacting CuI and organic lithium ($R_5$—Li; $R_5$=(C1-C10)alkyl or (C6-C20)aryl), to which the compound represented by formula 6-1 and tri(C1-C10)alkylsilyl chloride are added to give the compound represented by formula 6-2; and 10) inducing oxidation and de-protection of the compound represented by formula 6-2 in the presence of DDQ (2,3-dichloro-5,6-dicyano-1,4-benzoquinone) and HMDS (hexamethyldisilazide) to give the compound represented by formula 6.

[Formula 6]

[Formula 6-1]

[Formula 6-2]

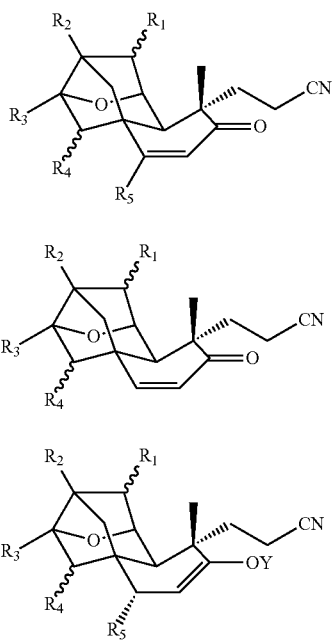

[In formulas 6, 6-1 and 6-2, $R_1$ is H, (C1-C10)alkyl, iodo, bromo or chloro; $R_2$ and $R_3$ are independently H, (C1-C10)alkyl or (C6-C20)aryl; $R_4$ is H, (C1-C10)alkyl, (C6-C20)aryl or (C6-C20)aryl(C1-C10)alkyl; $R_5$ is (C1-C10)alkyl or (C6-C20)aryl; Y is tri(C1-C10)alkylsilyl.]

Tricyclo ketone derivative represented by formula 10 is prepared by the following steps:

11) reacting the compound represented by formula 16 and allyl derivative represented by formula 17 in the presence of sodium hydride, followed by hydrolysis and reaction with diazomethane to give diazoketone derivative represented by formula 13; and 12) inducing carbonyl ylide [3+2] cycloaddition of diazoketone derivative represented by formula 13 in the presence of rhodium catalyst to give tricyclo ketone derivative represented by formula 10.

[Formula 10]

[Formula 16]

[Formula 17]

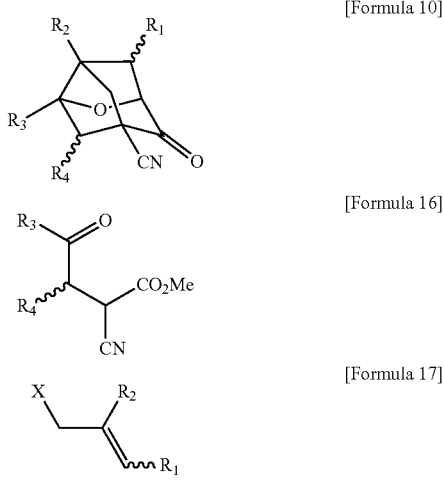

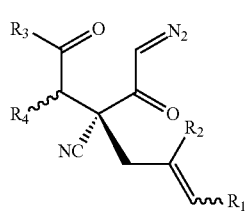

[Formula 13]

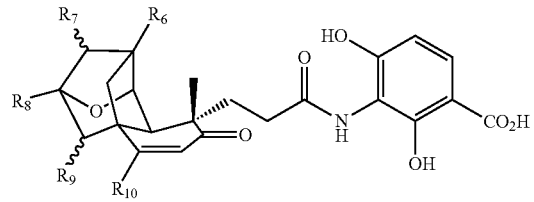

[Formula 3]

[In formulas 10, 13, 16 and 17, $R_1$ is (C1-C10)alkyl, iodo, bromo or chloro; $R_2$ and R 3 are independently H, (C1-C10)alkyl or (C6-C20)aryl; $R_4$ is H, (C1-C10)alkyl, (C6-C20)aryl or (C6-C20)aryl(C1-C10)alkyl; X is iodo, bromo or chloro.]

The rhodium catalyst used herein is preferably selected from the group consisting of rhodium(II) acetate ($Rh_2(OAc)_4$) and rhodium(II) trifluoroacetate ($[(CF_3COO)_2Rh]_2$). The preferable concentration of the rhodium catalyst is 2-5 mol %. If the concentration is less than 2 mol % or more than 5 mol %, yield will be reduced, indicating economically inefficiency.

The method for preparing tricyclo ketone derivative represented by formula 10 by carbonyl ylide [3+2] cycloaddition of diazoketone derivative represented by formula 13 is illustrated in reaction formula 1.

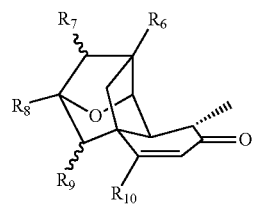

[Formula 20]

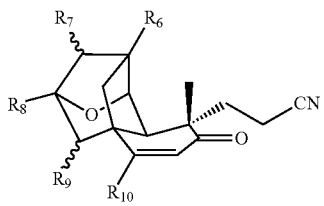

[Formula 21]

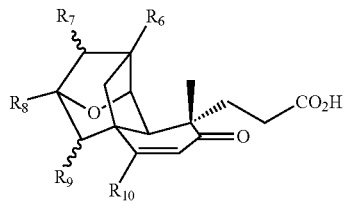

[Formula 22]

[Reaction Formula 1]

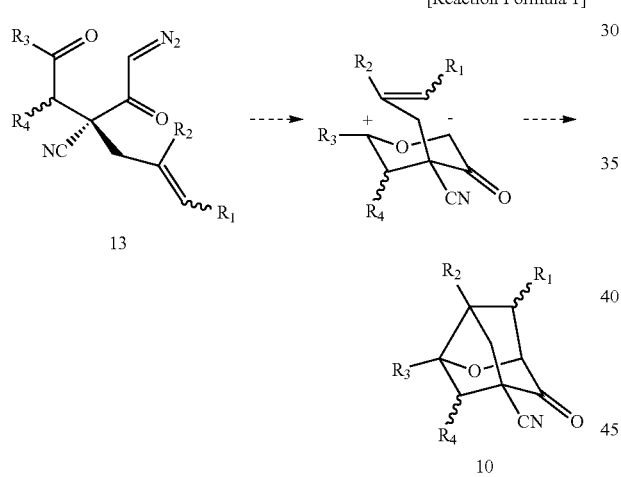

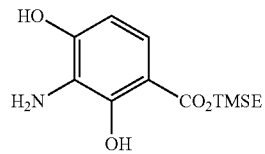

[Formula 8]

[Wherein, $R_1$ is (C1-C10)alkyl, iodo, bromo or chloro; $R_2$ and $R_3$ are independently H, (C1-C10)alkyl or (C6-C20)aryl; $R_4$ is H, (C1-C10)alkyl, (C6-C20)aryl or (C6-C20)aryl(C1-C10)alkyl.]

Isoplatensimycin and its derivatives represented by formula 3 are prepared by the following steps:

1) reacting enone derivative represented by formula 20 and acrylonitrile, leading to cyanoethylation to give enone derivative represented by formula 21;
2) hydrolyzing enone derivative represented by formula 21 to give carboxylic acid derivative represented by formula 22;
3) reacting carboxylic acid derivative represented by formula 22 and aniline derivative represented by formula 8, leading to amidation to give ester compound represented by formula 23; and
4) de-protecting the protection group of ester compound represented by formula 23 by using TASF reagent [$(CH_3)_2N)_3S]^+[F_2Si(CH_3)_3]^-$ to give isoplatensimycin and its derivatives represented by formula 3.

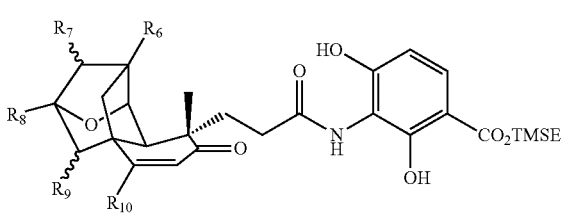

[Formula 23]

[In formulas 3, 20, 21, 22 and 23, $R_6$ is H, (C1-C10)alkyl, iodo, bromo or chloro; $R_7$, $R_8$ and $R_{10}$ are independently H, (C1-C10)alkyl or (C6-C20)aryl; $R_9$ is H, (C1-C10)alkyl, (C6-C20)aryl or (C6-C20)aryl(C1-C10)alkyl.]

When the substituent $R_{10}$ of enone derivative represented by formula 20 is H, the compound is prepared by the following steps:

5-1) reacting tricyclo ketone derivative represented by formula 24 and dimethyl 2-oxopropylphosphonate to give enone compound represented by formula 25;
6-1) inducing hydrosilylation of enone compound represented by formula 25 in the presence of ruthenium(I) catalyst, which is reduced into diisobutylaluminum hydride or diisopropylaluminum hydride, followed by hydrolysis to give ketoaldehyde compound represented by formula 26;

7-1) inducing intramolecular condensation of ketoaldehyde compound represented by formula 26 to give tetracyclo derivative represented by formula 19; and 8-1) inducing methylation of tetracyclo derivative represented by formula 19 to give enone derivative represented by formula 20.

7-2) inducing intramolecular condensation of diketone compound represented by formula 26 to give tetracyclo derivative represented by formula 19; and 8-2) inducing methylation of tetracyclo derivative represented by formula 19 to give enone derivative represented by formula 20.

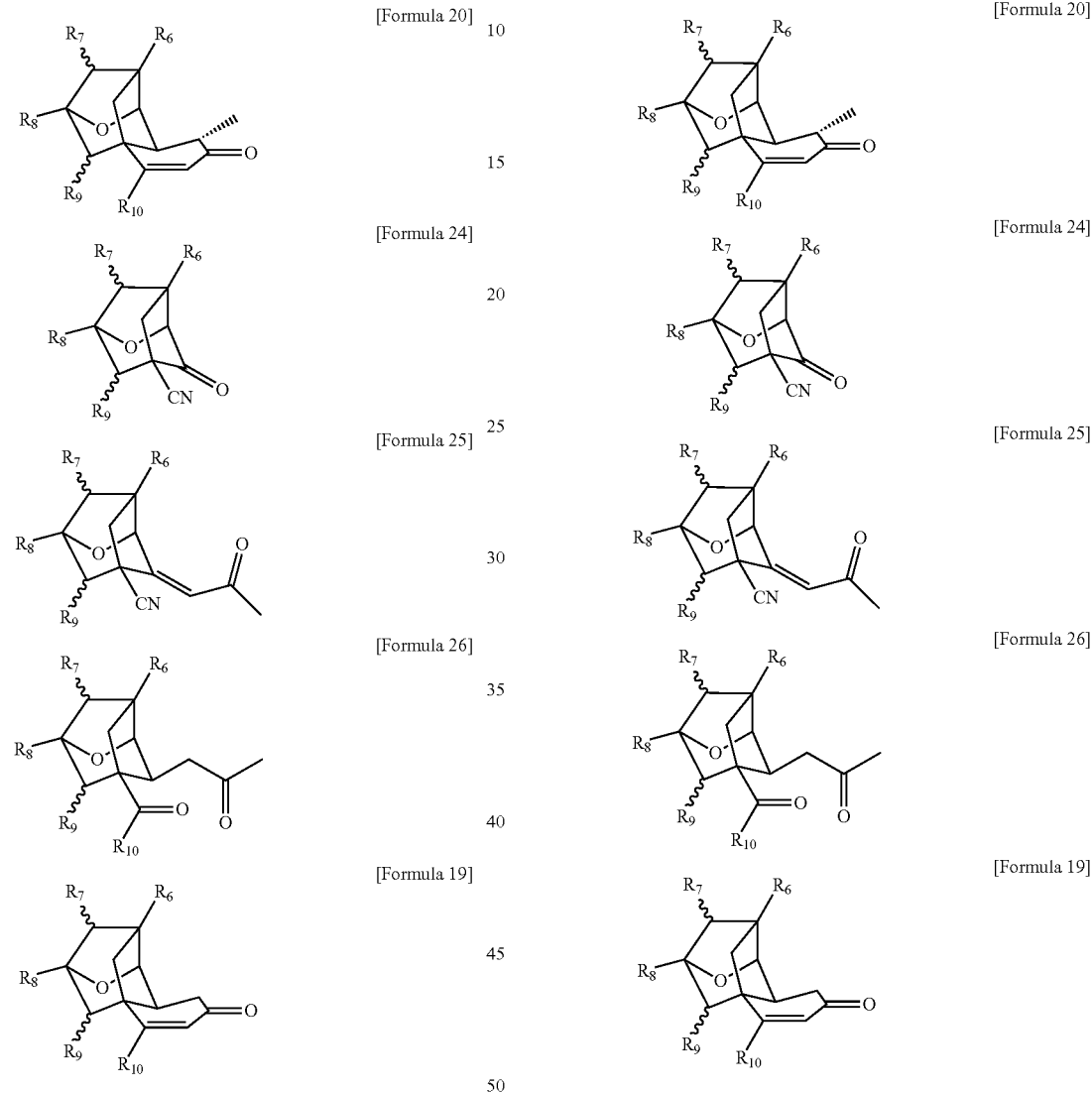

[In formulas 19, 20, 24, 25 and 26, $R_6$ is H, (C1-C10)alkyl, iodo, bromo or chloro; $R_7$, and $R_8$ are independently H, (C1-C10)alkyl or (C6-C20)aryl; $R_9$ is H, (C1-C10)alkyl, (C6-C20)aryl or (C6-C20)aryl(C1-C10)alkyl; $R_{10}$ is H.]

When the substituent $R_{10}$ of enone derivative represented by formula 20 is (C1-C10)alkyl or (C6-C20)aryl, the compound is prepared by the following steps:

5-2) reacting tricyclo ketone derivative represented by formula 24 and dimethyl 2-oxopropylphosphonate to give enone compound represented by formula 25;

6-2) inducing hydrosilylation of enone compound represented by formula 25 in the presence of ruthenium(I) catalyst, to which organic lithium ($R_{10}$—Li; $R_{10}$=(C1-C10)alkyl or (C6-C20)aryl) is added, followed by hydrolysis to give diketone compound represented by formula 26;

[In formulas 19, 20, 24, 25 and 26, $R_6$ is H, (C1-C10)alkyl, iodo, bromo or chloro; $R_7$ and $R_8$ are independently H, (C1-C10)alkyl or (C6-C20)aryl; $R_9$ is H, (C1-C10)alkyl, (C6-C20)aryl or (C6-C20)aryl(C1-C10)alkyl; $R_{10}$ is (C1-C10)alkyl or (C6-C20)aryl.]

When the substituent $R_{10}$ of enone derivative represented by formula 21 is H, which is used as the starting material, the substituent $R_{10}$ of enone derivative represented by formula 21 can be substituted with (C1-C10)alkyl or (C6-C20)aryl by the following steps:

9) reacting CuI and organic lithium ($R_{10}$—Li; $R_{10}$=(C1-C10)alkyl or (C6-C20)aryl), to which the compound represented by formula 21-1 and tri(C1-C10)alkylsilyl chloride are added to give the compound represented by formula 21-2; and 10) inducing oxidation and de-protection of the compound represented by formula 21-2 in the presence of DDQ (2,3- dichloro-5,6-dicyano-1,4-benzoquinone) and HMDS (hexamethyldisilazide) to give the compound represented by formula 21.

[Formula 21]

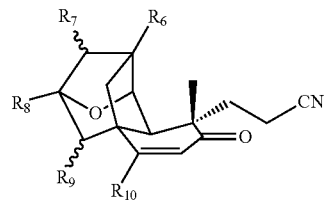

[Formula 21-1]

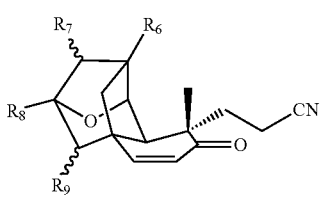

[Formula 21-2]

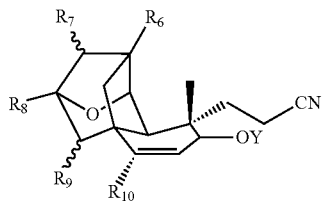

[In formulas 21, 21-1 and 21-2, $R_6$ is H, (C1-C10)alkyl, iodo, bromo or chloro; $R_7$ and $R_8$ are independently H, (C1-C10)alkyl or (C6-C20)aryl; $R_9$ is H, (C1-C10)alkyl, (C6-C20)aryl or (C6-C20)aryl(C1-C10)alkyl; $R_{10}$ is (C1-C10)alkyl or (C6-C20)aryl; Y is tri(C1-C10)alkylsilyl.]

Tricyclo ketone derivative represented by formula 24 is prepared by the following steps:

11) reacting the compound represented by formula 29 and allyl derivative represented by formula 30 in the presence of sodium hydride, followed by hydrolysis and reaction with diazomethane to give diazoketone derivative represented by formula 27; and 12) inducing carbonyl ylide [3+2] cycloaddition of diazoketone derivative represented by formula 27 in the presence of rhodium catalyst to give tricyclo ketone derivative represented by formula 24.

[Formula 24]

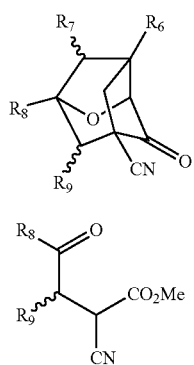

[Formula 29]

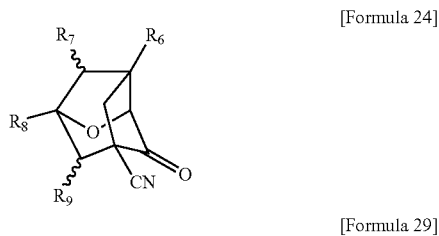

[Formula 30]

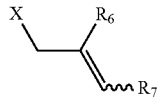

[Formula 27]

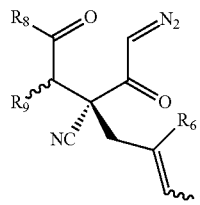

[In formulas 24, 27, 29 and 30, $R_6$ is H, (C1-C10)alkyl, iodo, bromo or chloro; $R_7$ and $R_8$ are independently H, (C1-C10)alkyl or (C6-C20)aryl; $R_9$ is H, (C1-C10)alkyl, (C6-C20)aryl or (C6-C20)aryl(C1-C10)alkyl; X is iodo, bromo or chloro.]

The rhodium catalyst used herein is preferably selected from the group consisting of rhodium(II) acetate ($Rh_2(OAc)_4$) and rhodium(II) trifluoroacetate ($[(CF_3COO)_2Rh]_2$). The preferable concentration of the rhodium catalyst is 2-5 mol %. If the concentration is less than 2 mol % or more than 5 mol %, yield will be reduced, indicating economically inefficiency.

The method for preparing tricyclo ketone derivative represented by formula 24 by carbonyl ylide [3+2] cycloaddition of diazoketone derivative represented by formula 27 is illustrated in reaction formula 2.

[Reaction Formula 2]

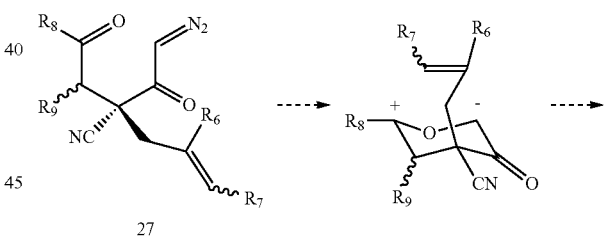

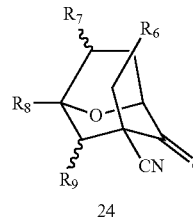

[Wherein, $R_6$ is H, (C1-C10)alkyl, iodo, bromo or chloro; $R_7$ and $R_8$ are independently H, (C1-C10)alkyl or (C6-C20)aryl; $R_9$ is H, (C1-C10)alkyl, (C6-C20)aryl or (C6-C20)aryl(C1-C10)alkyl.]

The present invention also relates to tricyclo ketone derivative represented by formula 10 or formula 24 and a preparing method of the same, in which tricyclo ketone derivative is characteristically prepared from diazoketone derivative by carbonyl ylide [3+2] cycloaddition.

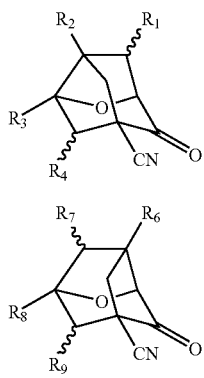

[Formula 10]

[Formula 24]

[In formulas 10 and 24, $R_1$ and $R_6$ are independently H, (C1-C10)alkyl, iodo, bromo or chloro; $R_2$, $R_3$, $R_7$, and $R_8$ are independently H, (C1-C10)alkyl or (C6-C20)aryl; $R_4$ and $R_9$ are independently H, (C1-C10)alkyl, (C6-C20)aryl or (C6-C20)aryl(C1-C10)alkyl.]

In formula 10, $R_1$ is H, methyl, ethyl, n-propyl, i-propyl, n-butyl, i-butyl, t-butyl, iodo, bromo or chloro; $R_2$ and $R_3$ are independently H, methyl, ethyl, n-propyl, i-propyl, n-butyl, i-butyl, t-butyl or phenyl; $R_4$ is H, methyl, ethyl, n-propyl, i-propyl, n-butyl, i-butyl, t-butyl, phenyl or benzyl, more preferably, $R_1$ is H, methyl, ethyl, n-propyl, i-propyl, n-butyl, i-butyl, t-butyl, iodo, bromo or chloro; $R_2$ is H or phenyl; $R_3$ is H, methyl, ethyl, n-propyl, i-propyl, n-butyl, i-butyl, t-butyl or phenyl; $R_4$ is H.

In formula 24, $R_6$ is H, methyl, ethyl, n-propyl, i-propyl, n-butyl, i-butyl, t-butyl, iodo, bromo or chloro; $R_7$ and $R_8$ are independently H, methyl, ethyl, n-propyl, i-propyl, n-butyl, i-butyl, t-butyl or phenyl; $R_9$ is H, methyl, ethyl, n-propyl, i-propyl, n-butyl, i-butyl, t-butyl, phenyl or benzyl, more preferably, $R_6$ is H, methyl, ethyl, n-propyl, i-propyl, n-butyl, i-butyl, t-butyl, iodo, bromo or chloro; $R_7$ is H or phenyl; $R_8$ is methyl, ethyl, n-propyl, i-propyl, n-butyl, i-butyl, t-butyl or phenyl; $R_9$ is H.

Tricyclo ketone derivative represented by formula 10 is prepared from diazoketone derivative represented by formula 13 in the presence of rhodium catalyst by carbonyl ylide [3+2] cycloaddition.

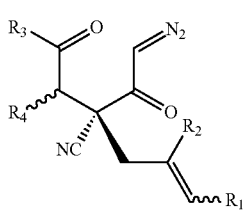

[Formula 13]

[In formula 13, $R_1$ is (C1-C10)alkyl, iodo, bromo or chloro; $R_2$ and $R_3$ are independently H, (C1-C10)alkyl or (C6-C20)aryl; $R_4$ is H, (C1-C10)alkyl, (C6-C20)aryl or (C6-C20)aryl(C1-C10)alkyl.]

Tricyclo ketone derivative represented by formula 24 is prepared from diazoketone derivative represented by formula 27 in the presence of rhodium catalyst by carbonyl ylide [3+2] cycloaddition.

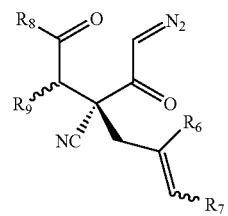

[Formula 27]

[In formula 27, $R_6$ is H, (C1-C10)alkyl, iodo, bromo or chloro; $R_7$ and $R_8$ are independently H, (C1-C10)alkyl or (C6-C20)aryl; $R_9$ is H, (C1-C10)alkyl, (C6-C20)aryl or (C6-C20)aryl(C1-C10)alkyl.]

The rhodium catalyst used herein is preferably selected from the group consisting of rhodium(II) acetate and rhodium (II) trifluoroacetate. The preferable concentration of the rhodium catalyst is 2-5 mol %. If the concentration is less than 2 mol % or more than 5 mol %, yield will be reduced, indicating economically inefficiency.

Diazoketone derivative represented by formula 13 is prepared by the following steps:

13) reacting ethyl cyanoacetate represented by formula 14 and carbonyl chloride compound represented by formula 15 in the presence of sodium (C1-C10)alkoxide to give the compound represented by formula 16;

14) reacting the compound represented by formula 16 and allyl derivative represented by formula 17 in the presence of sodium hydride, followed by hydrolysis to give the compound represented by formula 18; and 15) reacting the compound represented by formula 18 and diazomethane to give diazoketone derivative represented by formula 13.

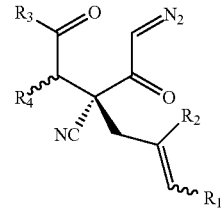

[Formula 13]

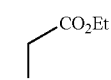

[Formula 14]

[Formula 15]

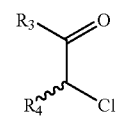

[Formula 16]

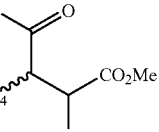

[Formula 17]

-continued

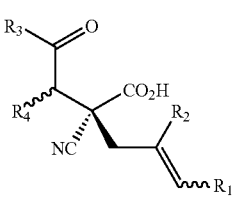

[Formula 18]

[In formulas 13 and 15 to 18, $R_1$ is (C1-C10)alkyl, iodo, bromo or chloro; $R_2$ and $R_3$ are independently H, (C1-C10)alkyl or (C6-C20)aryl; $R_4$ is H, (C1-C10)alkyl, (C6-C20)aryl or (C6-C20)aryl(C1-C10)alkyl; X is iodo, bromo or chloro.]

Another method for preparing diazoketone derivative represented by formula 13 comprises the following steps:

13) reacting isopropyl 2-cyanoacetate, (S)-propyleneoxide derivative represented by formula C and allyl derivative represented by formula 17 stepwise in the presence of sodium hydride to give lactone compound represented by formula A;

14) reacting 2-methyl-2-propanethiol, the lactone compound represented by formula A prepared above and DMP (Dess-Martin periodinane) stepwise in the presence of trimethylaluminum to give thioester compound represented by formula B; and 15) hydrolyzing the thioester compound represented by formula B prepared above, followed by reaction with diazomethane to give diazoketone derivative represented by formula 13.

[Formula 13]

[Formula A]

[Formula B]

[Formula C]

[Formula 17]

[In formulas 13, A, B, C and 17, $R_1$ is iodo, bromo or chloro; $R_2$ and $R_3$ are independently H, (C1-C10)alkyl or (C6-C20)aryl; $R_4$ is H, (C1-C10)alkyl, (C6-C20)aryl or (C6-C20)aryl(C1-C10)alkyl; X is iodo, bromo or chloro.]

Diazoketone derivative represented by formula 27 is prepared by the following steps:

13) reacting ethyl cyanoacetate represented by formula 14 and carbonyl chloride compound represented by formula 28 in the presence of sodium (C1-C10)alkoxide to give the compound represented by formula 29;

14) reacting the compound represented by formula 29 and allyl derivative represented by formula 30 in the presence of sodium hydride, followed by hydrolysis to give the compound represented by formula 31; and 15) reacting the compound represented by formula 31 and diazomethane to give diazoketone derivative represented by formula 27.

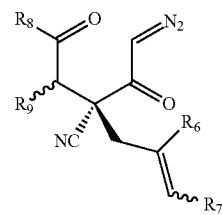

[Formula 27]

[Formula 14]

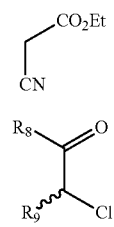

[Formula 28]

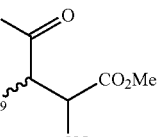

[Formula 29]

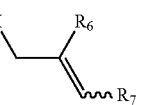

[Formula 30]

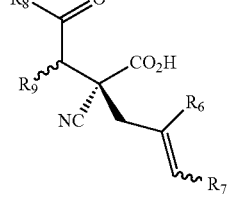

[Formula 31]

[In formulas 27 to 31, $R_6$, $R_7$, $R_8$ and $R_9$ are the same as defined in formula 24; X is iodo, bromo or chloro.]

The present invention also relates to tetracyclo derivative represented by formula 4 which plays an important role in the production of the antibiotic platensimycin as a major intermediate, in which tricyclo ketone derivative represented by formula 10 is characteristically used to give tetracyclo derivative represented by formula 4 according to the following steps:

5) reacting tricyclo ketone derivative represented by formula 10 and dimethyl 2-oxopropylphosphonate to give enone compound represented by formula 11;

6) inducing hydrosilylation of enone compound represented by formula 11 in the presence of ruthenium(I) catalyst, which is reduced into diisobutylaluminum hydride or diisopropylaluminum hydride or reacted with organic lithium ($R_5$—Li; $R_5$=(C1-C10)alkyl or (C6-C20)aryl) followed by hydrolysis to give the compound represented by formula 12; and 7) inducing intramolecular condensation of the compound represented by formula 12 to give tetracyclo derivative represented by formula 4.

6) inducing hydrosilylation of enone compound represented by formula 25 in the presence of ruthenium(I) catalyst, which is reduced into diisobutylaluminum hydride or diisopropylaluminum hydride or reacted with organic lithium ($R_{10}$—Li; $R_{10}$=(C1-C10)alkyl or (C6-C20)aryl), followed by hydrolysis to give the compound represented by formula 26; and 7) inducing intramolecular condensation of the compound represented by formula 26 to give tetracyclo derivative represented by formula 19.

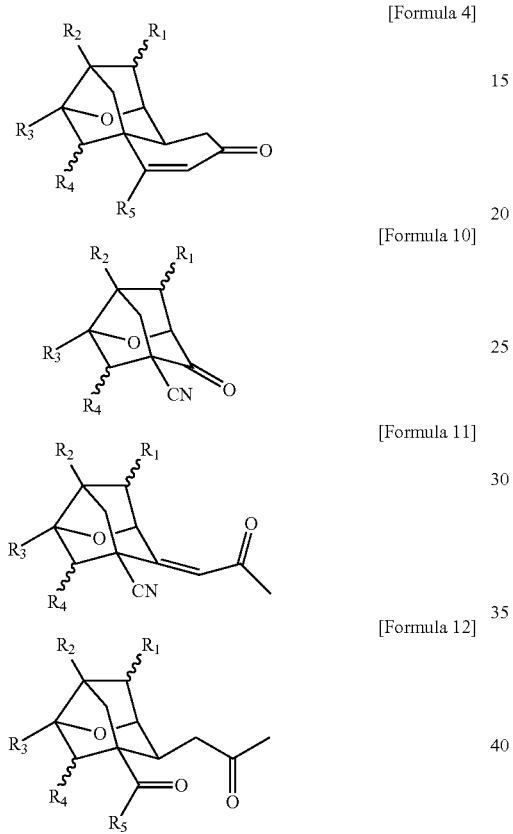

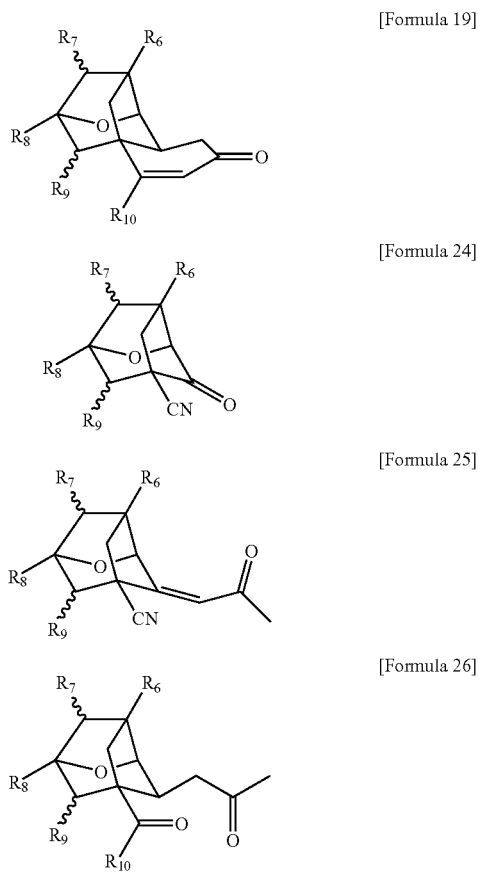

[In formulas 4, 10 to 12, $R_1$ is H, (C1-C10)alkyl, iodo, bromo or chloro; $R_2$, $R_3$ and $R_5$ are independently H, (C1-C10)alkyl or (C6-C20)aryl; $R_4$ is H, (C1-C10)alkyl, (C6-C20)aryl or (C6-C20)aryl(C1-C10)alkyl.]

In step 6), the compound represented by formula 12 prepared by the processes of hydrosilylation; reduction into diisobutylaluminum hydride or diisopropylaluminum hydride; and hydrolysis is keto aldehyde compound, in which the substituent $R_5$ is H. In the meantime, in step 6), the compound represented by formula 12 prepared by the processes of hydrosilylation; reaction with organic lithium ($R_5$—Li; $R_5$=(C1-C10)alkyl or (C6-C20)aryl); and hydrolysis is diketone compound, in which the substituent $R_5$ is (C1-C10)alkyl or (C6-C20)aryl.

The present invention also relates to tetracyclo derivative represented by formula 19 which plays an important role in the production of isoplatensimycin as a major intermediate, in which tricyclo ketone derivative represented by formula 24 is characteristically used to give tetracyclo derivative represented by formula 19 according to the following steps:

5) reacting tricyclo ketone derivative represented by formula 24 and dimethyl 2-oxopropylphosphonate to give enone compound represented by formula 25;

[In formulas 19, 24, 25 and 26, $R_6$ is H, (C1-C10)alkyl, iodo, bromo or chloro; $R_7$, $R_8$ and $R_{10}$ are independently H, (C1-C10)alkyl or (C6-C20)aryl; $R_9$ is H, (C1-C10)alkyl, (C6-C20)aryl or (C6-C20)aryl(C1-C10)alkyl.]

In step 6), the compound represented by formula 26 prepared by the processes of hydrosilylation; reduction into diisobutylaluminum hydride or diisopropylaluminum hydride; and hydrolysis is keto aldehyde compound, in which the substituent $R_5$ is H. In the meantime, in step 6), the compound represented by formula 26 prepared by the processes of hydrosilylation; reaction with organic lithium ($R_{10}$—Li; $R_{10}$=(C1-C10)alkyl or (C6-C20)aryl); and hydrolysis is diketone compound, in which the substituent $R_{10}$ is (C1-C10)alkyl or (C6-C20)aryl.

The preparing method of diazoketone derivative represented by formula 13 is illustrated in reaction formula 3 and the preparing method of tetracyclo derivative represented by formula 4 is illustrated in reaction formula 4.

[Reaction Formula 3]

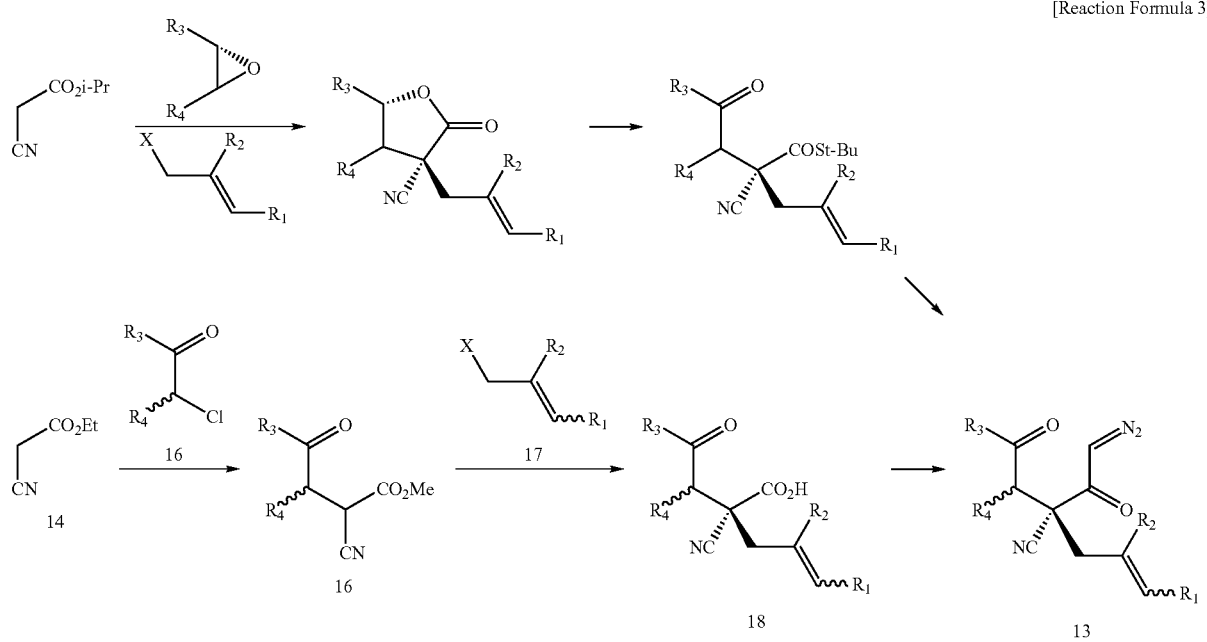

[In reaction formula 3, $R_1$ is (C1-C10)alkyl, iodo, bromo or chloro; $R_2$ and $R_3$ are independently H, (C1-C10)alkyl or (C6-C20)aryl; $R_4$ is H, (C1-C10)alkyl, (C6-C20)aryl or (C6-C20)aryl(C1-C10)alkyl; X is iodo, bromo or chloro.]

[Reaction Formula 4]

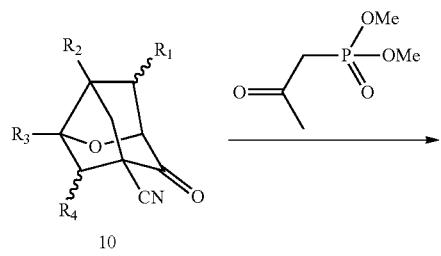

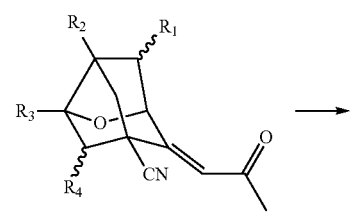

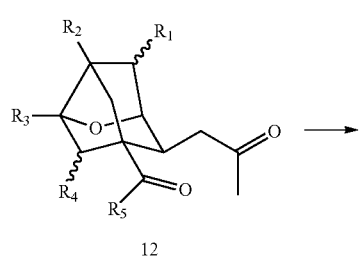

-continued

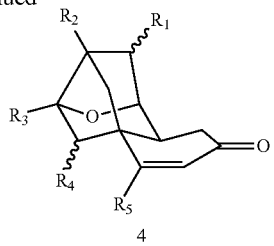

[In reaction formula 4, $R_1$ is H, (C1-C10)alkyl, iodo, bromo or chloro; $R_2$ and $R_3$ are independently H, (C1-C10) alkyl or (C6-C20)aryl; $R_4$ is H, (C1-C10)alkyl, (C6-C20)aryl or (C6-C20)aryl(C1-C10)alkyl; X is iodo, bromo or chloro.]

The preparing method of diazoketone derivative represented by formula 27 is illustrated in reaction formula 5 and the preparing method of tetracyclo derivative represented by formula 19 is illustrated in reaction formula 6.

[Reaction Formula 5]

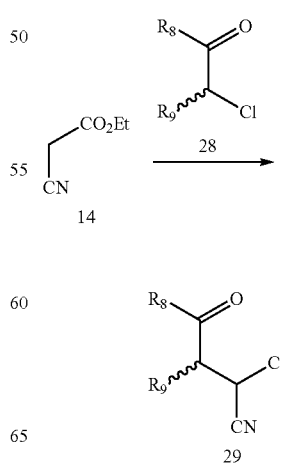

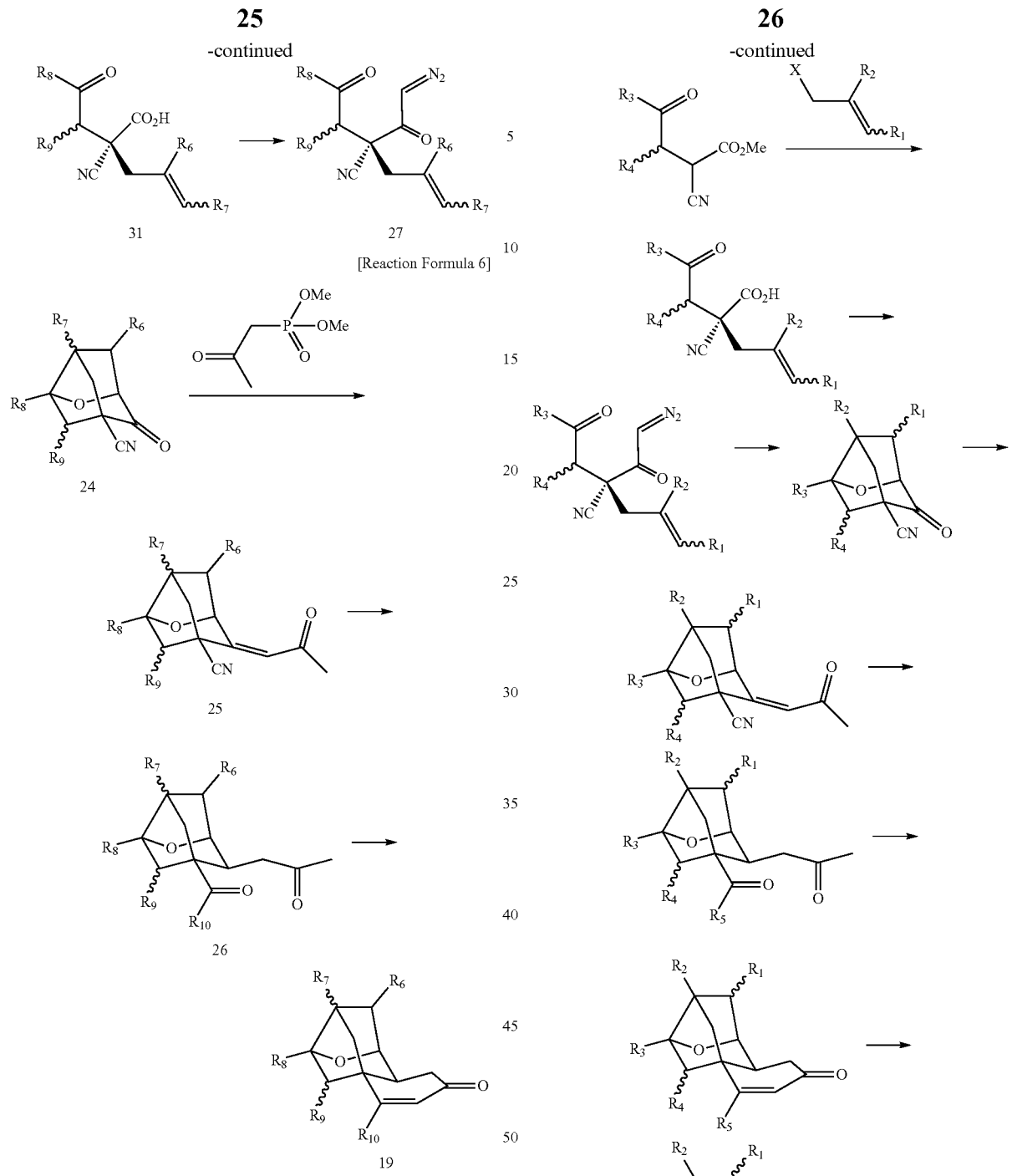
[In reaction formulas 5 and 6, $R_6$, $R_7$, $R_8$ and $R_9$ are the same as defined in formula 24; X is iodo, bromo or chloro.]
The preparing method of platensimycin and its derivatives is summarized and illustrated in reaction formulas 7 and 8.
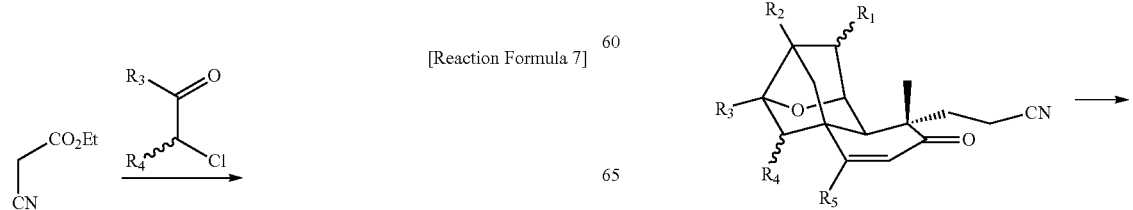

27
-continued
28
-continued
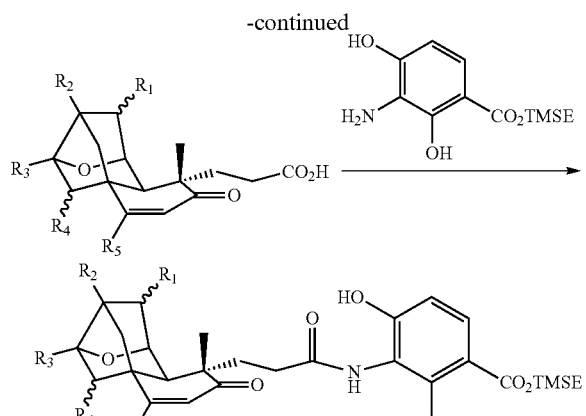
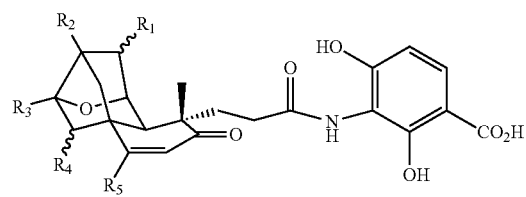
[In reaction formula 7, $R_1$ is (C1-C10)alkyl, iodo, bromo or chloro; $R_2$, $R_3$ and $R_5$ are independently H, (C1-C10)alkyl or (C6-C20)aryl; $R_4$ is H, (C1-C10)alkyl, (C6-C20)aryl or (C6-C20)aryl(C1-C10)alkyl.]
[Reaction Formula 8]
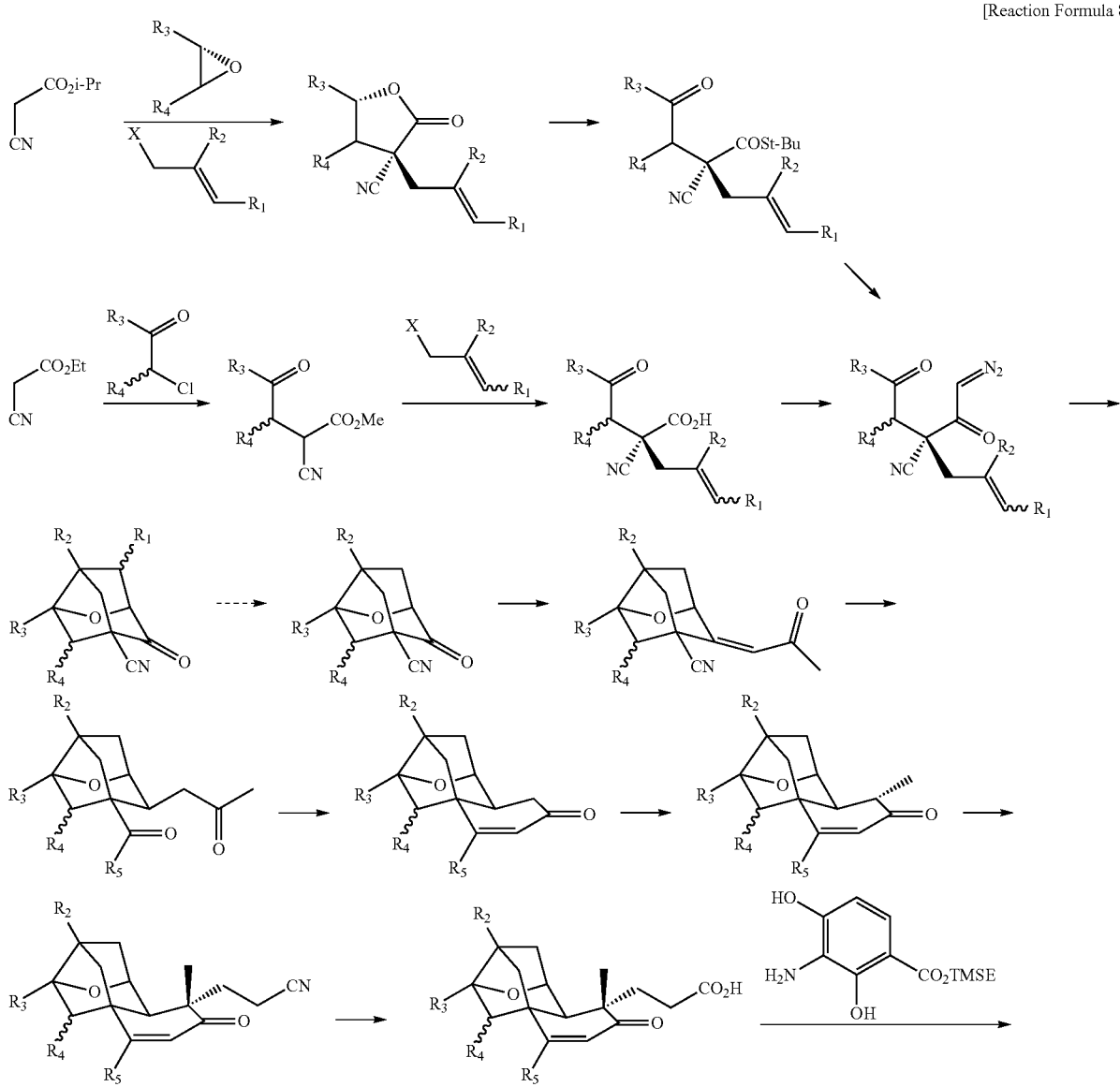

-continued
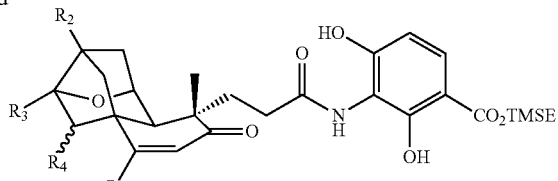
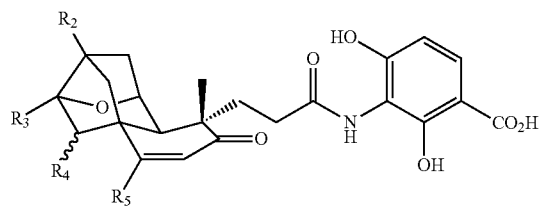
[In reaction formula 8, $R_1$ is iodo, bromo or chloro; $R_2$, $R_3$ and $R_5$ are independently H, (C1-C10)alkyl or (C6-C20)aryl; $R_4$ is H, (C1-C10)alkyl, (C6-C20)aryl or (C6-C20)aryl(C1-C10)alkyl.]
The preparing method of isoplatensimycin and its derivatives is summarized and illustrated in reaction formula 9.
[Reaction Formula 9]
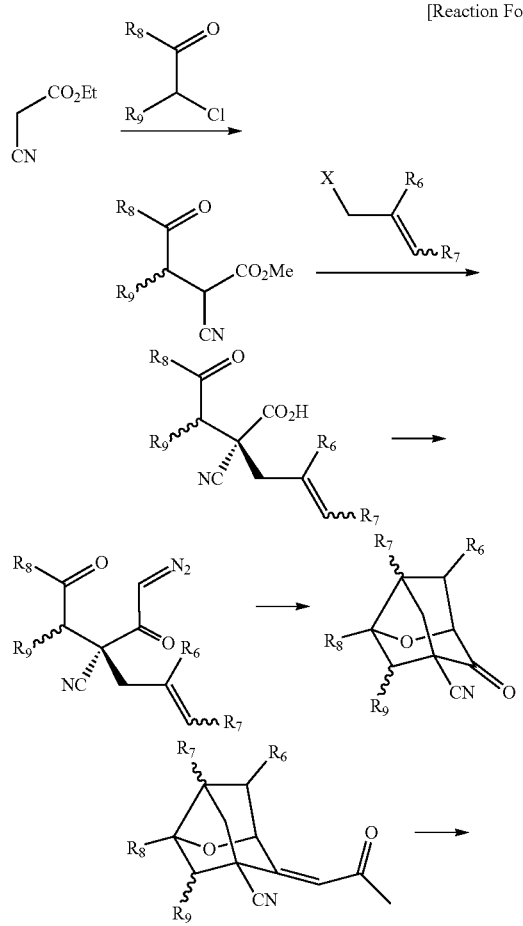
-continued
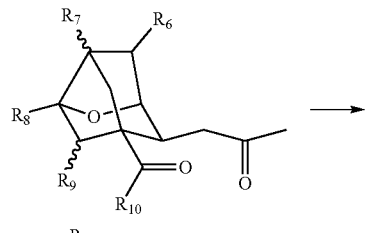
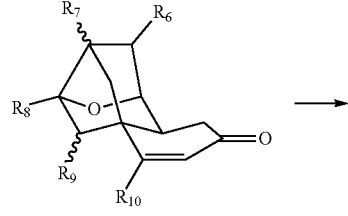
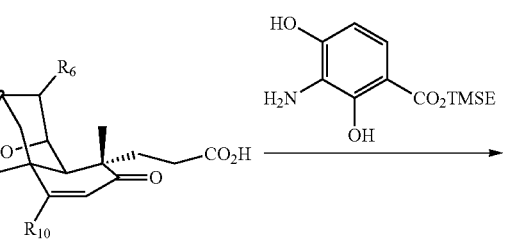

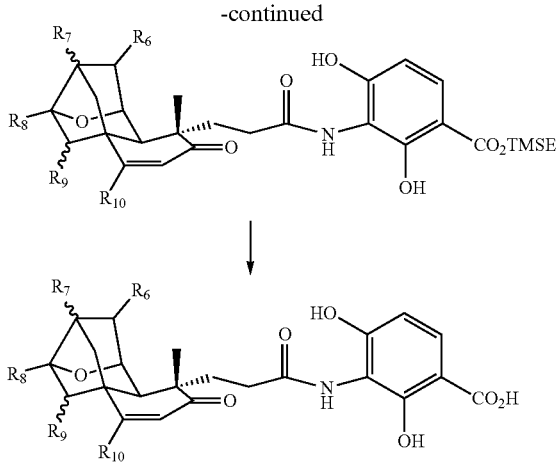

[In reaction formula 9, $R_6$ is H, (C1-C10)alkyl, iodo, bromo or chloro; $R_7$, $R_8$ and $R_{10}$ are independently H, (C1-C10)alkyl or (C6-C20)aryl; $R_9$ is H, (C1-C10)alkyl, (C6-C20)aryl or (C6-C20)aryl(C1-C10)alkyl.]

MODE FOR THE INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

General Information $^1$H- and $^{13}$C-NMR spectra were obtained on a Bruker DPX-300 (300 MHz), a Bruker Avance-600 (600 MHz), or a Varian/Oxford As-500 (500 MHz) spectrophotometer. Chemical shift values were recorded as parts per million relative to tetramethylsilane as an internal standard unless otherwise indicated, and coupling constants in Hertz. Mass spectra were recorded on a JEOL JMS 600W spectrometer using electron impact (EI) or chemical ionization (CI) methods, and a JEOL JMS AX505WA spectrometer using fast atom bombardment (FAB) method. Significant fragments are reported in the following fashion: m/z (relative intensity).

The progress of reaction was checked on TLC plates (Merck 5554 Kiesel gel 60 F254), and the spots were visualized under 254 nm UV light and/or by charring after dipping the TLC plate into a vanillin solution (9.0 g of vanillin and 1.5 mL of concentrated sulfuric acid in 300 mL of methanol), a $KMnO_4$ solution (3 g of $KMnO_4$, 20 g of $K_2CO_3$, and 5 mL of 5% NaOH solution in 300 mL of water), or a phosphomolybdic acid solution (250 mg phosphomolybdic acid in 50 mL ethanol). Column chromatography was performed on silica gel (Merck 9385 Kiesel gel 60) using hexanes-EtOAc (v/v). The solvents were simple distilled unless otherwise noted.

Unless otherwise specified, all reactions were conducted under a slight positive pressure of dry nitrogen. The usual work-up refers to washing the quenched reaction mixture with brine, drying the organic extracts over anhydrous $MgSO_4$ and evaporating under reduced pressure using a rotary evaporator.

Solvents used in the reactions were dried under nitrogen atmosphere. THF was distilled from Na-benzophenone, and $CH_2Cl_2$ was distilled from $P_2O_5$. Benzene was washed with conc. $H_2SO_4$, distilled from Na-benzophenone, and stored over 4 molecular sieves. $Et_2O$ was distilled from LAH. $CH_3CN$ was distilled from $CaH_2$ and stored over 4 Å molecular sieves. Pyridine and TEA was distilled over KOH and stored over 4 Å molecular sieves.

EXAMPLE 1 TO 8

Preparation of Intermediates

Example 1

Preparation of Diazoketone (C)

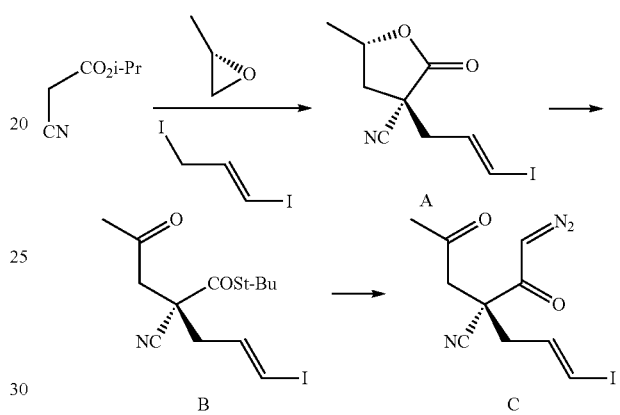

Preparation of Lactone (A)

Isopropyl cyanoacetate (0.5 g, 3.9 mmol) was slowly added to a solution of sodium hydride (60% dispersion in mineral oil, 157 mg, 3.9 mmol) in THF (16 mL) at 0° C. The mixture was stirred for 10 min before addition of (S)-propylene oxide (purchased from Aldrich, 0.27 mL, 3.9 mmol). After heating under reflux for 6 h, the mixture was cooled to r.t. and an other portion of (S)-propylene oxide (0.27 mL, 3.9 mmol) was added to the mixture. The mixture was further refluxed for 6 h then cooled to 0° C. (E)-Iodoallyl iodide (1.6 g, 5.4 mmol) in THF (3 mL) was slowly added to the mixture. After stirring at r.t. for 30 min, the mixture was diluted with $Et_2O$ (200 mL) before addition of 1 N HCl (20 mL). The organic phase was washed with brine (30 mL), dried over $MgSO_4$, filtered and concentrated. The residue was purified by flash column chromatography (hexanes-EtOAc, 5:1) to give lactone (A) (726 mg, 63%).

$R_f$ 0.42 (hexanes-EtOAc, 2:1). $^1$H NMR (500 MHz, $CDCl_3$): δ 6.46-6.62 (m, 2H), 4.60-4.73 (m, 1H), 2.76 (dd, J=14.2, 6.4 Hz, 1H), 2.49-2.63 (m, 2H), 2.37 (dd, J=13.5, 7.6 Hz, 1H), 1.54 (d, J=6.1 Hz, 3H). $^{13}$C NMR (125 MHz, $CDCl_3$): δ 169.9, 137.0, 117.6, 83.1, 75.3, 43.3, 41.1, 39.4, 21.2. IR (neat): $v_{max}$=3056, 2983, 2932, 2320, 2248, 1778, 1607, 1449, 1387, 1346, 1199, 1047, 944 $cm^-$. $[α]^{25}_D$–38.8 (c 0.41, $CHCl_3$).

Preparation of Thioester (B)

To a solution of trimethylaluminium (2 M in toluene, 5.1 mL, 10.2 mmol) in dry $CH_2Cl_2$ (12 mL) was carefully added 2-methyl-2-propanethiol (1.1 mL, 10.2 mmol) at 0° C. and the resultant mixture was allowed to warm to r.t. over 20 min and cooled again to 0° C. A solution of lactone (A) (370 mg, 1.27 mmol) in CH$_2$Cl$_2$ (2 mL) was added and the mixture was stirred at 0° C. for 3 h. The mixture was cooled to −78° C. and quenched with Et$_2$O (40 mL) followed by careful addition of 1 N HCl (15 mL). The organic phase was washed with 1 N HCl (15 mL×2), sat. NaHCO$_3$ (10 mL), and brine (10 mL), dried over Na$_2$SO$_4$, and concentrated under reduced pressure. The residue was dissolved in CH$_2$Cl$_2$ (3 mL) and added to a solution of Dess-Martin periodinane (1.1 g, 2.6 mmol) in CH$_2$Cl$_2$ (6 mL) at 0° C. After 2 h, the reaction mixture was treated with sat. NaHCO$_3$ solution (10 mL) and the aqueous phase was extracted with Et$_2$O (20 mL×2). The combined organic phase was washed with brine (10 mL), dried over MgSO$_4$, and concentrated. The residue was purified by flash column chromatography (hexanes-EtOAc, 4:1) to give thioester (B) (443 mg, 92%, two steps).

R$_f$ 0.45 (hexanes-EtOAc, 2:1). $^1$H NMR (500 MHz, CDCl$_3$): δ 6.47-6.59 (m, 1H), 6.36 (d, J=14.4 Hz, 1H), 3.18 and 2.90 (ABq, J=18.0 Hz, 2H), 2.62 and 2.54 (ABX, J$_{AB}$=13.8, J$_{AX}$=7.8, J$_{AX}$=7.6 Hz, 2H), 2.19 (s, 3H), 1.50 (s, 9H). $^{13}$C NMR (125 MHz, CDCl$_3$): δ 202.1, 194.7, 137.6, 118.7, 82.0, 50.7, 50.5, 48.7, 43.9, 29.8. IR (neat): ν$_{max}$=2964, 2924, 2240, 1723, 1674, 1607, 1475, 1365, 1173, 925, 767 cm$^{-1}$. [α]$^{25}_D$−107.2 (c 1.03, CHCl$_3$).

Preparation of Diazoketone (C)

Thioester (B) (443 mg, 1.17 mmol) was dissolved in MeOH (6 mL) and 1 N KOH solution (2 mL) was added to the solution at 0° C. The reaction mixture was stirred for 10 min at r.t. and treated slowly with 1 N HCl (3 mL) at 0° C. After extraction with EtOAc (30 mL×2), the organic phase was washed with brine (5 mL×2), dried over MgSO$_4$, filtered and concentrated.

TEA (0.20 mL, 1.40 mmol) was added to the solution of the residue was in Et$_2$O (15 mL) at −20° C. and the mixture was treated with isobutyl chloroformate (0.17 mL, 1.29 mmol). After 30 min, an ethereal solution of diazomethane, which was prepared by the reaction of Diazald (1.5 g, 7.1 mmol) with KOH (1.5 g, 27 mmol), was slowly added to the reaction mixture, and the mixture was allowed to warm to 0° C. After stirring the reaction mixture for 4 h, excess diazomethane was decomposed by careful addition of acetic acid. The reaction mixture was filtered through a short column of silicagel with the aid of Et$_2$O and concentrated. The residue was purified by flash column chromatography (hexanes-EtOAc, 4:1) to provide enantiomerically enriched diazoketone (C) (337 mg, 88%, two steps). [α]$^{25}_D$−212.0 (c 0.50, CHCl$_3$).

Example 2

Preparation of Diazoketone (C)

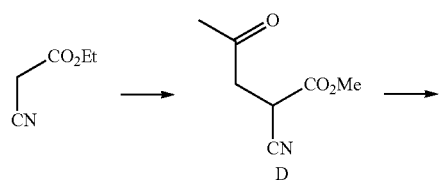

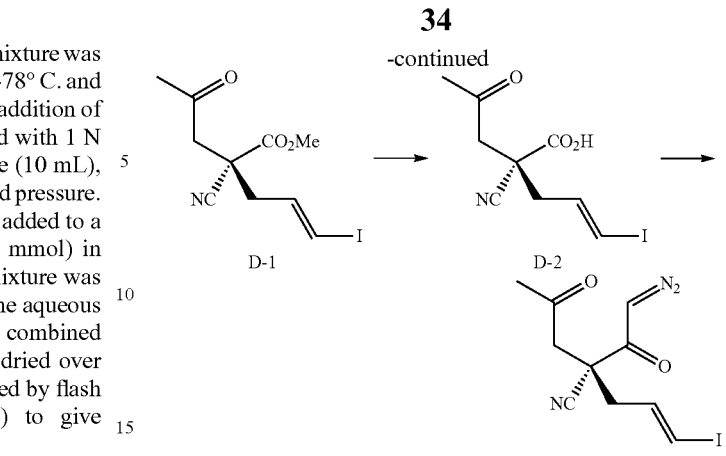

Preparation of Ester (D)

Ethyl cyanoacetate (1.0 mL, 9.4 mmol) was added to a solution of sodium methoxide prepared from absolute methanol (10 mL) and sodium (220 mg, 9.6 mmol) at 0° C. After 10 min stirring, chloroacetone (0.75 mL, 9.4 mmol) was added and the reaction mixture was stirred at r.t. for 3 h. After dilution with Et$_2$O (30 mL), the reaction mixture was cooled to 0° C. and treated with sat. NH$_4$Cl solution (30 mL). The aqueous phase was extracted with EtOAc (40 mL×2) and the combined organic extracts were washed with 1 N HCl solution (saturated with NaCl, 20 mL×2), dried over MgSO$_4$, filtered and concentrated. The residue was purified by flash column chromatography (hexanes-EtOAc, 2:1) to give ester (D) (1.3 g, 88%).

R$_f$ 0.21 (hexanes-EtOAc, 2:1). $^1$H NMR (500 MHz, CDCl$_3$): δ 3.97 (dd, J=7.1, 5.4 Hz, 1H), 3.84 (s, 3H), 3.22 and 3.02 (ABX, J$_{AB}$=18.4, J$_{AX}$=7.1, J$_{AX}$=5.4 Hz, 2H), 2.26 (s, 3H). $^{13}$C NMR (125 MHz, CDCl$_3$): δ 202.5, 165.9, 116.1, 54.0, 42.2, 31.4, 29.6. IR (neat): ν$_{max}$=3646, 2959, 2922, 2254, 1747, 1719, 1634, 1436, 1370, 1270, 1057, 826 cm$^{-1}$. MS m/z (CI, relative intensity): 156 (M$^{++}$1, 100), 155 (2), 152 (16), 139 (5), 124 (49), 75 (3). HRMS (CI): calcd. for C$_7$H$_{10}$O$_3$N (M$^+$+1) 156.0660, found 156.0659.

Preparation of Diazoketone (C)

Ester (D) (1.0 g, 6.4 mmol) was added to a solution of sodium hydride (60% dispersion in mineral oil, 280 mg, 7.1 mmol) in THF (30 mL) at 0° C. The mixture was stirred for 10 min before addition of (E)-iodoallyl iodide (2.3 g, 7.7 mmol) and warmed to r.t. After 2 h, the reaction was quenched by addition of sat. NH$_4$Cl solution (20 mL), and the reaction mixture was extracted with Et$_2$O (100 mL×2). The organic phase was washed with brine (50 mL), dried over MgSO$_4$, filtered and concentrated. Purification of the residue by flash column chromatography (hexanes-EtOAc, 3:1) gave methyl ester (D-1) (2.0 g, 97%.).

R$_f$ 0.35 (hexanes-EtOAc, 2:1). $^1$H NMR (500 MHz, CDCl$_3$): δ 6.51-6.58 (m, 1H), 6.40 (d, J=14.4 Hz, 1H), 3.85 (s, 3H), 3.15 and 3.00 (ABq, J=18.1 Hz, 2H), 2.61 and 2.57 (ABX, J$_{AB}$=14.0, J$_{AX}$=7.7, J$_{BX}$=7.6 Hz, 2H), 2.21 (s, 3H). $^{13}$C NMR (125 MHz, CDCl$_3$): δ 202.7, 168.5, 137.5, 118.2, 82.1, 54.1, 48.8, 44.1, 42.8, 29.6.

Methyl ester (D-1) (2.0 g, 6.2 mmol) was dissolved in MeOH (30 mL) and 1 N KOH solution (15 mL) was added to the solution at 0° C. The reaction mixture was stirred for 10 min at r.t. and treated slowly with 2 N HCl (8 mL) at 0° C.

After extraction with EtOAc (100 mL×2), the organic phase was dried over MgSO$_4$, filtered and concentrated. The residue was dissolved in toluene (10 mL) and evaporated to provide the crude acid (D-2) (1.9 g, quant.) which was used in the next step without further purification.

TEA (1.1 mL, 7.4 mmol) was added to the solution of the crude acid (D-2)(1.9 g, 6.2 mmol) in THF (60 mL) at −20° C. and the mixture was treated with isobutyl chloroformate (1.1 mL, 6.8 mmol). After 30 min, an ethereal solution of diazomethane, which was prepared by the reaction of Diazald (8.0 g, 38 mmol) with KOH (8.0 g, 143 mmol), was slowly added to the reaction mixture, and the mixture was allowed to warm to 0° C. After stirring the reaction mixture for 4 h, excess diazomethane was decomposed by careful addition of acetic acid. The reaction mixture was filtered through a short column of silicagel with the aid of Et$_2$O and concentrated. The residue was purified by flash column chromatography (hexanes-EtOAc, 4:1) to provide diazoketone (C)(1.8 g, 88%, two steps).

R$_f$ 0.45 (hexanes-EtOAc, 2:1). $^1$H NMR (500 MHz, CDCl$_3$): δ 6.49-6.57 (m, 1H), 6.41 (d, J=14.5 Hz, 1H), 6.07 (s, 1H), 3.27 and 2.89 (ABq, J=18.2 Hz, 2H), 2.57 and 2.44 (ABX, J$_{AB}$=13.9, J$_{AX}$=7.6, J$_{BX}$=7.9 Hz, 2H), 2.18 (s, 3H). $^{13}$C NMR (125 MHz, CDCl$_3$): δ 202.8, 187.8, 137.5, 119.7, 82.4, 56.3, 48.9, 46.7, 43.3, 29.5. IR (neat): ν$_{max}$=3427, 3113, 2924, 2240, 2118, 1714, 1633, 1361, 1159, 951 cm$^{-1}$. MS m/z (CI, relative intensity): 332 (M$^+$+1, 100), 322 (14), 304 (39), 277 (22), 276 (11), 195 (13), 178 (22), 177 (37), 176 (39), 167 (11), 149 (57). HRMS (CI): calcd. for C$_{10}$H$_{11}$O$_2$N$_3$I (M$^+$+1) 331.9896, found 331.9897.

Example 3

Preparation of Diazoketone (E)

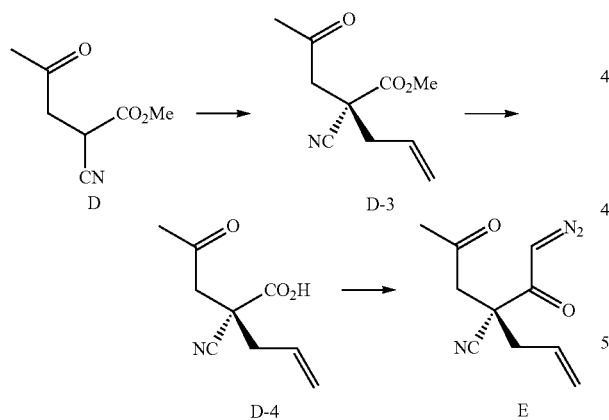

Ester (D)(1.0 g, 6.4 mmol) was added to a solution of sodium hydride (60% dispersion in mineral oil, 280 mg, 7.1 mmol) in THF (30 mL) at 0° C. The mixture was stirred for 10 min before the addition of allyl bromide (0.67 mL, 7.7 mmol) and warmed to r.t. After 2 h, the reaction was quenched by addition of sat. NH$_4$Cl solution (20 mL), and the reaction mixture was extracted with Et$_2$O (100 mL×2). The organic phase was washed with brine (50 mL), dried over MgSO$_4$, filtered and concentrated. Purification of the residue by flash column chromatography (hexanes-EtOAc, 3:1) gave methyl ester (D-3) (1.3 g, quant.).

R$_f$ 0.35 (hexanes-EtOAc, 2:1). $^1$H NMR (500 MHz, CDCl$_3$): δ 5.77-5.88 (m, 1H), 5.14-5.33 (m, 2H), 3.84 (s, 3H), 3.17 and 3.00 (ABq, J=22.0 Hz, 2H), 2.63 and 2.55 (ABX, J$_{AB}$=16.4, J$_{AX}$=8.8, J$_{BX}$=9.0 Hz, 2H), 2.20 (s, 3H). $^{13}$C NMR (125 MHz, CDCl$_3$): δ 203.0, 169.1, 130.2, 121.7, 118.6, 53.9, 49.1, 44.6, 41.3, 29.6.

Methyl ester (D-3) (1.0 g, 5.1 mmol) was dissolved in MeOH (30 mL) and 1N KOH solution (15 mL) was added to the solution at 0° C. The reaction mixture was stirred for 10 min at r.t. and treated slowly with 2 N HCl (8 mL) at 0° C. After extraction with EtOAc (100 mL×2), the organic phase was dried over MgSO$_4$, filtered and concentrated. The residue was dissolved in toluene (10 mL) and evaporated to provide the crude acid (D-4) (930 mg, quant.) which was used in the next step without further purification.

TEA (0.93 mL, 6.6 mmol) was added to the solution of the crude acid (D-4) (930 mg, 5.1 mmol) in Et$_2$O (51 mL) at 0° C. and the mixture was treated with isobutyl chloroformate (0.79 mL, 6.1 mmol). After 30 min, an ethereal solution of diazomethane, which was prepared by the reaction of Diazald (6.6 g, 31 mmol) with KOH (6.6 g, 118 mmol), was slowly added to the reaction mixture, and the mixture was allowed to warm to r.t. After stirring the reaction mixture for 4 h, the flask was cooled in an ice bath and excess diazomethane was decomposed by careful addition of acetic acid. The reaction mixture was filtered through a short column of silicagel with the aid of Et$_2$O and concentrated. The residue was purified by flash column chromatography (hexanes-EtOAc, 4:1) to provide diazoketone (E)(863 mg, 70%, two steps).

R$_f$ 0.45 (hexanes-EtOAc, 2:1). $^1$H NMR (500 MHz, CDCl$_3$): δ 6.07 (s, 1H), 5.75-5.86 (m, 1H), 5.19-5.35 (m, 2H), 3.30 and 2.91 (ABq, J=22.0 Hz, 2H), 2.59 and 2.43 (ABX, J$_{AB}$=16.3, J$_{AX}$=8.4, J$_{BX}$=9.3 Hz, 2H), 2.18 (s, 3H). $^{13}$C NMR (125 MHz, CDCl$_3$): δ 203.2, 188.5, 130.1, 122.0, 120.2, 56.1, 49.1, 47.2, 41.6, 29.6.

Example 4

Preparation of ketone (F)

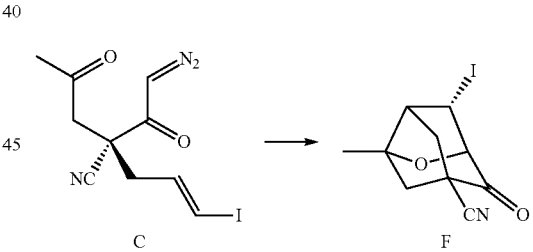

3 mol % Rh$_2$(OAc)$_4$ was added to a solution of a diazoketone (C) (300 mg) in CH$_2$Cl$_2$ (52 mL). After stirring for 10 h, the mixture was filtered through a short column of silica gel with the aid of hexanes-EtOAc (1:1) to remove the catalyst, and the filtrate was concentrated in vacuo. The residue was purified by flash column chromatography (hexanes-acetone-CH$_2$Cl$_2$, 4:1:1) to provide ketone (F) as a mixture of keto and hydrate forms (228 mg, 83%).

R$_f$ 0.20 (hexanes-acetone-CH$_2$Cl$_2$, 4:1:1). $^1$H NMR (500 MHz, CDCl$_3$): δ 4.43 (s, 1 H), 4.22 (s, 1H), 3.05 (d, J=7.1 Hz, 1H), 2.75 (dd, J=11.9, 3.1 Hz, 1H), 2.47 (dd, J=13.0, 7.1 Hz, 1H), 2.32 (d, J=12.0 Hz, 1H), 2.22 (dd, J=13.0, 3.2 Hz, 1H), 1.77 (s, 3H). $^{13}$C NMR (125 MHz, CDCl$_3$): δ 193.6, 115.9, 89.5, 87.5, 53.7, 53.5, 51.5, 46.8, 27.5, 23.1. IR (neat): ν$_{max}$=3390, 2978, 2874, 2247, 1740, 1632, 1444, 1383, 1243, 1113, 1026, 825, 612 cm$^{-1}$. MS m/z (FAB, relative intensity): 304 (M$^+$+1, 6), 289 (7), 273 (4), 219 (18), 194 (13), 176 (15), 154 (95), 136 (100), 107 (32), 90 (30), 77 (37). HRMS (FAB): calcd. for $C_{10}H_{11}O_2NI$ ($M^++1$) 303.9834, found 303.9824.

Example 5

Preparation of Ketone (H)

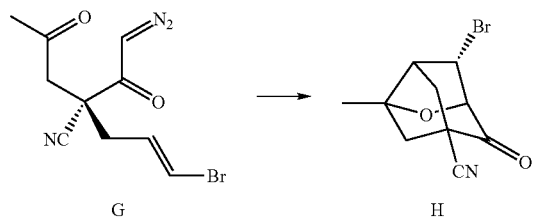

3 mol % $Rh_2(OAc)_4$ was added to a solution of a diazoketone (G) (74 mg) in $CH_2Cl_2$ (52 mL). After stirring for 10 h, the mixture was filtered through a short column of silica gel with the aid of hexanes-EtOAc (1:1) to remove the catalyst, and the filtrate was concentrated in vacuo. The residue was purified by flash column chromatography (hexanes-acetone-$CH_2Cl_2$, 4:1:1) to provide ketone (H) as a mixture of keto and hydrate forms (55 mg, 82%).

$R_f$ 0.20 (hexanes-acetone-$CH_2Cl_2$, 4:1:1). $^1$H NMR (500 MHz, $CDCl_3$): δ 4.47 (s, 1H), 4.22 (s, 1H), 3.03 (d, J=7.0 Hz, 1H), 2.77 (dd, J=11.7, 2.9 Hz, 1H), 2.55 (dd, J=12.8, 7.3 Hz, 1H), 2.31 (d, J=11.7 Hz, 1H), 2.17 (dd, J=12.8, 2.9 Hz, 1H), 1.73 (s, 3H). $^{13}$C NMR (125 MHz, $CDCl_3$): δ 194.2, 115.7, 88.4, 87.3, 53.7, 53.1, 52.6, 51.1, 44.4, 22.6. MS m/z (FAB, relative intensity): 256 ($M^++1$, 100), 231 (9), 230 (89), 229 (21), 228 (91), 227 (11), 176 (24), 148 (32), 118 (10), 106 (29), 59 (11). HRMS (CI): calcd. for $C_{10}H_{11}NO_2Br$ ($M^++1$) 255.9973, found 255.9971.

Example 6

Preparation of Cyclic enone (L)

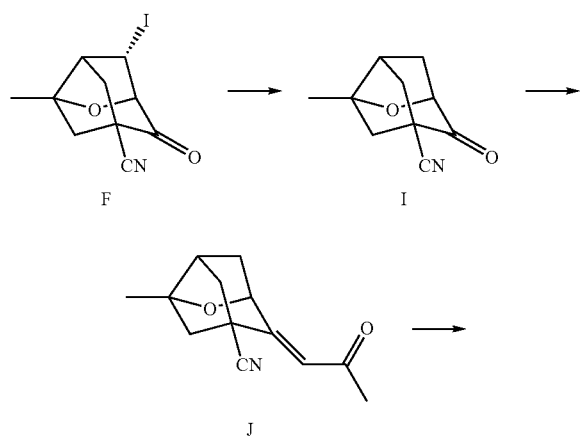

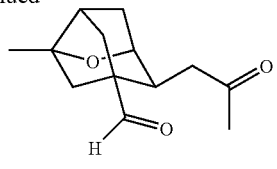

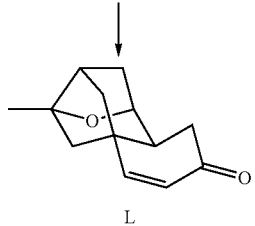

Preparation of Ketone (I)

To a solution of hypophosphorous acid (50% aq. solution, 1.05 g, 7.95 mmol) in MeOH (25 mL), 1-ethylpiperidine (1.09 mL, 7.95 mmol) was slowly added at 0° C. After 10 min, a solution of ketone (F) (481 mg, 1.59 mmol) in MeOH (5 mL) was added to the solution, followed by the addition of $Et_3B$ (1M in hexanes, 3.2 mL, 3.2 mmol). The reaction mixture was warmed to r.t. and stirred 20 min before dilution with EtOAc (150 mL). The organic phase was washed with brine (30 mL×2), dried over $MgSO_4$, filtered and concentrated. Flash column chromatography (hexanes-EtOAc, 1:1) provided ketone (I) (264 mg, 94%) as a mixture of keto and hydrate forms.

$R_f$ 0.19 (hexanes-EtOAc, 1:1). $^1$H NMR (500 MHz, $CDCl_3$) δ 4.40 (d, J=4.8 Hz, 1 H), 2.68-2.73 (m, 2H), 2.46-2.52 (m, 1H), 2.33 (d, J=11.7 Hz, 1H), 2.28-2.31 (m, 1H), 2.16 (dd, J=12.1, 2.9 Hz, 1H), 1.95 (d, J=12.5 Hz, 1H), 1.58 (s, 3H). $^{13}$C NMR (125 MHz, $CDCl_3$): δ 197.6, 116.4, 86.6, 83.5, 53.4, 52.4, 47.1, 44.1, 42.3, 22.0. IR (neat): $v_{max}$=3418, 2974, 2870, 2247, 1744, 1453, 1384, 1289, 1126, 1038, 833 $cm^{-1}$. MS m/z (FAB, relative intensity): 178 ($M^++1$, 19), 165 (10), 154 (24), 149 (14), 136 (38), 107 (32), 95 (40), 77 (42), 69 (64), 55 (100), 43 (83). HRMS (FAB): calcd. for $C_{10}H_{12}O_2N$ ($M^++1$) 178.0868, found 178.0874. $[α]^{25}_D$+7.2 (c 0.44, MeOH).

Preparation of Enone (J)

Dimethyl 2-oxopropylphosphonate (0.23 mL, 1.7 mmol) was added to a stirred suspension of anhydrous LiCl (126 mg, 2.98 mmol) and DIPEA (0.39 mL, 2.2 mmol) in anhydrous MeCN (15 mL) at 0° C. After 15 min, a solution of ketone (I) (264 mg, 1.49 mmol) in anhydrous MeCN (2 mL) was added to the mixture and the reaction mixture was stirred for 2 h at r.t. before dilution with $Et_2O$ (100 mL). The organic phase was washed with brine (20 mL×2), dried over $MgSO_4$, filtered and concentrated. The residue was purified by flash column chromatography (hexanes-EtOAc, 3:1) to give enone (J) (291 mg, 90%).

$R_f$ 0.75 (hexanes-EtOAc, 1:1). $^1$H NMR (500 MHz, $CDCl_3$): δ 6.44 (s, 1H), 5.82 (d, J=4.8 Hz, 1H), 2.56 (t, J=6.4 Hz, 1H), 2.43 (dd, J=11.2, 3.1 Hz, 1H), 2.36-2.41 (m, 1H), 2.29 (s, 3H), 2.18-2.25 (m, 1H), 2.15 (d, J=11.4 Hz, 1H), 2.02 (dd, J=11.4, 3.3 Hz, 1H), 1.82 (d, J=11.7 Hz, 1H), 1.47 (s, 3H). $^{13}$C NMR (125 MHz, $CDCl_3$): δ 198.4, 149.5, 121.5, 118.9, 86.2, 75.2, 53.5, 48.7, 46.0, 44.7, 43.0, 32.0, 22.4. IR (neat): $\nu_{max}$=3519, 2972, 2869, 2244, 1694, 1626, 1447, 1381, 1176, 1039, 960, 831 cm$^{-1}$. MS m/z (FAB, relative intensity): 218 (M$^+$+1, 16), 200 (7), 155 (25), 154 (100), 138 (30), 137 (59), 136 (75), 124 (10), 120 (13), 107 (23), 89 (21). HRMS (FAB): calcd. for C$_{13}$H$_{16}$O$_2$N (M$^+$+1) 218.1181, found 218.1183. $[\alpha]^{25}{}_D$ −1.0 (c 0.76, CHCl$_3$).

Preparation of Aldehyde (K)

Dimethylphenylsilane (0.062 mL, 0.40 mmol) was added to a solution of enone (J) (73 mg, 0.34 mmol) and (Ph$_3$P)$_3$RhCl (6.2 mg, 0.0067 mmol) in toluene (0.7 mL) at r.t. The reaction mixture was stirred for 1 h at 60° C. and cooled to 40° C. After slow addition of DIBAL (1M in toluene, 1 mL, 1 mmol), the reaction mixture was stirred for 1 h and carefully quenched by addition of AcOH—H$_2$O (1:1) solution (1.5 mL). The mixture was stirred vigorously at 0° C. for 1 h and diluted with EtOAc (15 mL). The mixture was washed with brine (5 mL×2), dried over Na$_2$SO$_4$, filtered and concentrated. This crude mixture was dissolved in THF (2 mL) before dropwise addition of 2 N HCl (0.1 mL) at 0° C. The mixture was stirred at 0° C. for 1 h and diluted with EtOAc (15 mL), washed with brine (5 mL), dried over Na$_2$SO$_4$, filtered and concentrated. The residue was purified by flash column chromatography (hexanes-acetone, 6:1) to give aldehyde (K) (45 mg, 59%).

R$_f$ 0.40 (hexanes-acetone, 3:1) $^1$H NMR (500 MHz, CDCl$_3$): δ 9.32 (s, 1H), 4.24 (br. s., 1H), 2.82 (br. s., 1H), 2.62 (dd, J=17.4, 4.9 Hz, 1H), 2.35 (t, J=6.6 Hz, 1H), 2.18 (d, J=7.8 Hz, 1H), 2.15 (s, 3H), 1.98 (dd, J=11.1, 3.3 Hz, 1H), 1.84-1.93 (m, 2H), 1.79 (d, J=11.7 Hz, 1H), 1.65-1.71 (m, 2H), 1.44 (s, 3H). $^{13}$C NMR (125 MHz, CDCl$_3$): δ 206.6, 202.8, 85.8, 79.0, 59.1, 48.0, 44.7, 42.7, 38.5, 37.8, 35.9, 30.4, 23.0. IR (neat): $\nu_{max}$=3411, 2964, 2715, 1714, 1452, 1379, 1168, 1099, 994, 935, 824, 687 cm$^{-1}$. $[\alpha]^{25}{}_D$ −27.6 (c 0.70, CHCl$_3$).

Preparation of Cyclic Enone (L)

p-TsOH monohydrate (10 mol %, 4 mg) was added to a solution of aldehyde (K) (49 mg, 0.22 mmol) in toluene (4 mL) and the mixture was heated under reflux for 2 h with concomitant removal of water (Dean-Stark trap). After cooling to r.t., the mixture was diluted with Et$_2$O (10 mL), washed with sat. NaHCO$_3$ solution (3 mL), dried over MgSO$_4$, filtered and concentrated. Flash column chromatography (hexanes-acetone, 6.5:1) provided cyclic enone (L) (43 mg, 96%).

R$_f$ 0.42 (hexanes-acetone, 3:1). $^1$H NMR (500 MHz, CDCl$_3$): δ 6.62 (d, J=10.3 Hz, 1 H), 5.94 (d, J=10.3 Hz, 1H), 4.16 (t, J=3.3 Hz, 1H), 2.27-2.44 (m, 4H), 1.92-1.97 (m, 2H), 1.89 (d, 1H), 1.75-1.78 (m, 2H), 1.66 (d, J=11.0 Hz, 1H), 1.45 (s, 3H). $^{13}$C NMR (125 MHz, CDCl$_3$): δ 199.1, 155.2, 128.9, 87.0, 79.0, 51.7, 46.2, 44.2, 42.7, 42.3, 37.9, 37.5, 23.1. IR (neat): $\nu_{max}$=3501, 2955, 2871, 1681, 1607, 1448, 1379, 1281, 1249, 1138, 1038, 821 cm$^{-1}$. MS m/z (CI, relative intensity): 205 (M$^+$+1, 55), 154 (100), 136 (82), 135 (20), 107 (46), 91 (31), 81 (31), 69 (45), 55 (62), 43 (50), 41 (37), 29 (11). HRMS (FAB): calcd. for C$_{13}$H$_{17}$O$_2$ (M$^+$+1) 205.1229, found 205.1231. $[\alpha]^{25}{}_D$ −22.8 (c 0.46, CHCl$_3$).

Example 7

Preparation of Ketone (M)

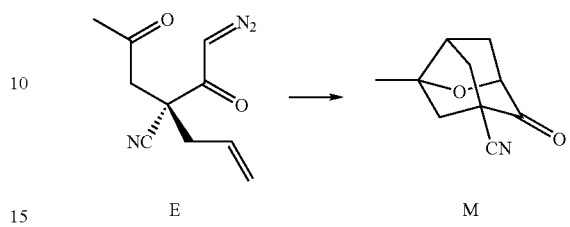

Rh$_2$(TFA)$_4$ (17 mg, 0.026 mmol) was added to a solution of diazoketone (E) (100 mg, 0.52 mmol) in CH$_2$Cl$_2$ (52 mL). After stirring for 10 h, the reaction mixture was filtered through a short column of silica gel with the aid of hexanes-EtOAc (1:1) to remove the catalyst, and the filtrate was concentrated in vacuo. The residue was purified by flash column chromatography (hexanes-acetone-CH$_2$Cl$_2$, 4:1:1) to provide ketone (M) (74 mg, 80%).

R$_f$ 0.20 (hexanes-acetone-CH$_2$Cl$_2$, 4:1:1). $^1$H NMR (500 MHz, CDCl$_3$) of the hydrate: δ 4.26 (s, 1H), 4.02 (d, J=5.5 Hz, 1H), 3.08 (s, 1H), 2.84 (q, J=6.2 Hz, 1H), 2.46-2.53 (m, 1H), 2.16 (dt, J=13.6, 2.4 Hz, 1H), 1.85 (d, J=13.6 Hz, 1H), 1.73-1.83 (m, 3H), 1.33 (s, 3H). $^{13}$C NMR (125 MHz, CDCl$_3$) of the hydrate: δ 119.7, 100.3, 82.3, 80.5, 46.3, 45.2, 41.3, 39.1, 37.7, 22.7. MS m/z (CI, relative intensity): 178 (M$^+$+1, 100), 150 (96), 149 (36), 123 (13), 118 (5), 105 (4), 93 (8), 83 (3). HRMS (CI): calcd. for C$_{10}$H$_{12}$O$_2$N (M$^+$+1) 178.0868, found 178.0867.

Example 8

Preparation of Cyclic Enone (P)

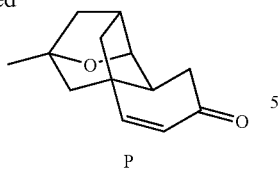

(m, 1H), 1.74-1.80 (m, 3H), 1.70 (dd, J=1.5, 12.5 Hz, 1H), 1.61-1.67 (m, 1H), 1.30 (s, 3H).

Preparation Example 1

Preparation of Platensimycin (1)

Preparation of Enone (N)

Dimethyl 2-oxopropylphosphonate (0.047 mL, 0.34 mmol) was added to a stirred suspension of anhydrous LiCl (26 mg, 0.62 mmol) and DIPEA (0.081 mL, 0.46 mmol) in anhydrous THF (3 mL) at 0° C. After 15 min, a solution of ketone (M) (55 mg, 0.31 mmol) in anhydrous THF (0.3 mL) was added to the mixture and the reaction mixture was stirred for 4 h at r.t. before dilution with Et₂O (20 mL). The organic phase was washed with brine (5 mL×2), dried over MgSO₄, filtered and concentrated. The residue was purified by flash column chromatography (hexanes-EtOAc, 3:1) to give enone (N) (28 mg, 41%).

R$_f$ 0.6 (hexanes-EtOAc, 1:1). ¹H NMR (500 MHz, CDCl₃): δ 6.30 (s, 1H), 5.72 (d, J=5.5 Hz, 1H), 2.93 (q, J=6.1 Hz, 1H), 2.30 (s, 3H), 2.16-2.21 (m, 1H), 2.11 (d, J=12.9 Hz, 1H), 2.07 (d, J=11.8 Hz, 1H), 1.92-1.98 (m, 1H), 1.87 (s, 1H), 1.81-1.86 (m, 1H), 1.30 (s, 3H). ¹³C NMR (125 MHz, CDCl₃): δ 197.9, 156.5, 118.9, 116.0, 80.4, 75.8, 47.6, 46.2, 43.3, 41.7, 39.2, 31.9, 22.7.

Preparation of Aldehyde (O)

Dimethylphenylsilane (0.087 mL, 0.56 mmol) was added to a solution of enone (N) (61 mg, 0.28 mmol) and (Ph₃P)₃RhCl (5.2 mg, 0.0056 mmol) in toluene (0.6 mL) at r.t. The reaction mixture was stirred for 1 h at 60° C. and cooled to −40° C. After slow addition of DIBAL (1M in toluene, 1.12 mL, 1.12 mmol), the reaction mixture was stirred for 2 h and carefully quenched by addition of AcOH—H₂O (1:1) solution (1.7 mL). The mixture was stirred vigorously at 0° C. for 1 h and diluted with EtOAc (15 mL). The mixture was washed with brine (5 mL×2), dried over Na₂SO₄, filtered and concentrated. This crude mixture was dissolved in THF (2 mL) before dropwise addition of 2 N HCl (0.1 mL) at 0° C. The mixture was stirred at 0° C. for 1 h and diluted with EtOAc (15 mL), washed with brine (5 mL), dried over Na₂SO₄, filtered and concentrated. The residue was purified by flash column chromatography (hexanes-acetone, 6:1) to give aldehyde (O) (21 mg, 34%).

R$_f$ 0.40 (hexanes-acetone, 3:1)

Preparation of Cyclic Enone (P)

p-TsOH monohydrate (10 mol %, 2 mg) was added to a solution of aldehyde (O) (21 mg, 0.095 mmol) in toluene (2 mL) and the mixture was heated under reflux for 2 h with concomitant removal of water (Dean-Stark trap). After cooling to r.t., the mixture was diluted with Et₂O (10 mL), washed with sat. NaHCO₃ solution (3 mL), dried over MgSO₄, filtered and concentrated. Flash column chromatography (hexanes-acetone, 6.5:1) provided cyclic enone (P) (14 mg, 72%).

R$_f$ 0.42 (hexanes-acetone, 3:1). ¹H NMR (500 MHz, CDCl₃): δ 6.70 (d, J=10.3 Hz, 1H), 5.85 (d, J=9.6 Hz, 1H), 4.34 (d, J=4.8 Hz, 1H), 2.90-2.96 (m, 1H), 2.55-2.62 (m, 1H), 2.47 (dd, J=6.1, 17.4 Hz, 1H), 2.18-2.29 (m, 1H), 2.04-2.11

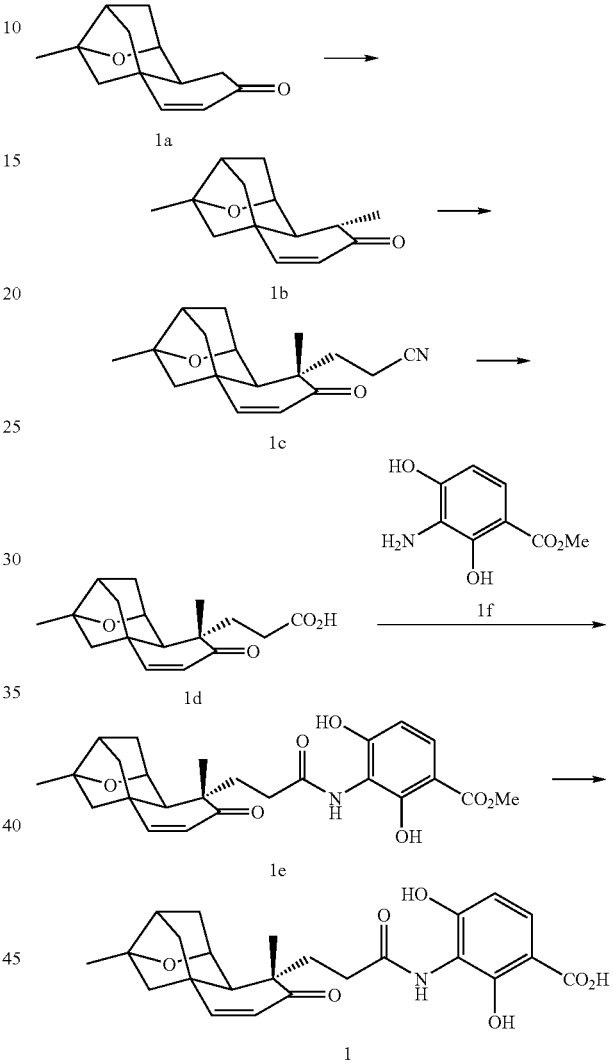

Preparation of Enone (1b)

KHMDS (0.5 M solution in toluene, 6.7 mL, 3.3 mmol) was added to a solution of enone (1a) (342 mg, 1.7 mmol) in THF (25 mL) and HMPA (5 mL) at −78° C. The reaction mixture was allowed to stir at −78° C. for 30 min, after which MeI (0.83 mL, 13.4 mmol) was added. The reaction mixture was stirred at −10° C. for 1 h. The reaction mixture was quenched with sat. NH₄Cl solution (10 mL) and extracted with ether (2×100 mL). The combined organic extracts were washed with brine (2×20 mL), dried over anhydrous Na₂SO₄, filtered and concentrated. The residue was purified by flash column chromatography (hexanes-acetone, 12:1) to give enone (1b) (315 mg, 86%).

R$_f$ 0.51 (hexanes-acetone, 3:1). ¹H NMR (500 MHz, CDCl₃): δ 6.54 (dd, J=5.6, 10.0 Hz, 1H), 5.92 (d, J=10.0 Hz, 1H), 4.35 (t, J=3.8 Hz, 1H), 2.41 2.31 (m, 2H), 2.10 2.05 (m, 1H), 1.98 1.93 (m, 1H), 1.91 (dd, J=3.5, 11.2 Hz, 1H), 1.87 (d, J=11.5 Hz, 1H), 1.81 (dd, J=3.4, 11.9 Hz, 1H), 1.77 1.71 (m, 1H), 1.62 (d, J=11.2 Hz, 1H), 1.44 (s, 3H), 1.13 (d, J=6.7 Hz, 3H). $^{13}$C NMR (125 MHz, CDCl$_3$): δ 201.4, 154.3, 128.4, 87.1, 77.9, 52.0, 48.8, 47.0, 44.6, 42.8, 41.4, 37.4, 23.3, 11.1.

Preparation of Enone (1c)

Enone (1b) (17 mg, 0.078 mmol) was dissolved in t-BuOH (0.8 mL) and 40% KOH solution (0.0013 mL, 0.016 mmol) was added to the solution. The reaction mixture was allowed to stir at 60° C. for 5 min, after which acrylonitrile (0.046 mL, 0.70 mmol) was slowly added over 2 h at 60° C. The reaction mixture was stirred at 60° C. for 12 h. The reaction mixture was quenched with sat. NH$_4$Cl solution (2 mL) and extracted with EtOAc (2×20 mL). The combined organic extracts were washed with brine (2×5 mL), dried over anhydrous Na$_2$SO$_4$, filtered and concentrated. The residue was purified by flash column chromatography (hexanes-acetone, 7:1) to give enone (1c) (15 mg, 71%).

R$_f$ 0.21 (hexanes-acetone, 3:1). $^1$H NMR (500 MHz, CDCl$_3$): δ 6.48 (d, J=10.1 Hz, 1H), 5.88 (d, J=10.1 Hz, 1H), 4.41 4.29 (m, 1H), 2.42 (t, J=6.6 Hz, 1H), 2.39 2.24 (m, 5H), 2.14 2.07 (m, 1H), 2.02 (dd, J=3.7, 12.0 Hz, 1H), 1.99 (d, J=12.3 Hz, 1H), 1.86 (dd, J=3.7, 11.2 Hz, 1H), 1.81 1.73 (m, 2H), 1.62 (d, J=14.3 Hz, 1H), 1.44 (s, 3H), 1.23 (s, 3H). $^{13}$C NMR (125 MHz, CDCl$_3$): δ 202.6, 154.1, 127.1, 119.7, 87.3, 76.5, 55.1, 46.5, 46.3, 46.2, 44.8, 43.4, 40.8, 31.8, 24.1, 23.2, 12.8.

Preparation of Carboxylic Acid (1d)

Enone (1c) (19 mg, 0.070 mmol) was dissolved in MeOH (0.6 mL) and 20% KOH solution (3.5 mL) was added to the solution. The reaction mixture was heated under reflux for 2 h. After cooling to r.t., the reaction mixture was treated with 2 N HCl (10 mL) and extracted with (30 mL×2). The combined organic extracts were washed with brine (2×10 mL), dried over anhydrous Na$_2$SO$_4$, filtered and concentrated. The residue was purified by flash column chromatography (CHCl$_3$-MeOH, 20:1) to give acid (1d) (20 mg, 98%).

R$_f$ 0.40 (CHCl$_3$-MeOH, 10:1). $^1$H NMR (500 MHz, CDCl$_3$): δ 6.48 (d, J=10.1 Hz, 1H), 5.88 (d, J=10.1 Hz, 1H), 4.36 4.33 (m, 1H), 2.42 (t, J=6.6 Hz, 1H), 2.39 2.24 (m, 4H), 2.14 2.07 (m, 1H), 2.02 (dd, J=3.7, 12.0 Hz, 1H), 2.00 (d, J=11.7 Hz, 1H), 1.86 (dd, J=3.7, 11.2 Hz, 1H), 1.81 1.73 (m, 2H), 1.61 (d, J=11.2 Hz, 1H), 1.44 (s, 3H), 1.23 (s, 3H). $^{13}$C NMR (125 MHz, CDCl$_3$): δ 203.3, 177.8, 153.6, 127.3, 87.2, 76.5, 54.9, 46.3, 46.0, 46.0, 44.7, 43.2, 40.5, 30.6, 29.0, 24.5, 23.0.

Preparation of Platensimycin Methyl Ester (1e)

TEA (0.11 mL, 0.79 mmol) and HATU (226 mg, 0.58 mmol) were added to a solution of carboxylic acid (1d) (53 mg, 0.18 mmol) and aniline (1f) (106 mg, 0.58 mmol) in DMF (1 mL) at room temperature. The reaction mixture was stirred at 24° C. for 15 h, after which brine (2 mL) was added. The resulting mixture was extracted with ether (3×20 mL), and the combined organic portions dried over Na$_2$SO$_4$, filtered and concentrated. The residue was purified by flash column chromatography (hexanes-acetone, 8:1) to give methyl ester (1e) (65 mg, 78%).

R$_f$ 0.41 (hexanes-acetone, 3:1). $^1$H NMR (500 MHz, CDCl$_3$): δ 11.64 (s, 1H), 11.07 (s, 1H), 8.09 (s, 1H), 7.56 (d, J=9.0 Hz, 1H), 6.51 (d, J=8.8 Hz, 1H), 6.50 (d, J=10.1 Hz, 1H), 5.93 (d, J=10.1 Hz, 1H), 4.44 (s, 1H), 3.92 (s, 3H), 2.53 (ddd, J=5.5, 12.2, 14.8 Hz, 1H), 2.46 2.32 (m, 5H), 2.15 2.08 (m, 1H), 2.06 (dd, J=3.6, 12.0 Hz, 1H), 2.02 (d, J=11.6 Hz, 1H), 1.94 1.84 (m, 2H), 1.79 (dd, J=6.8, 11.9 Hz, 1H), 1.63 (d, J=11.1 Hz, 1H), 1.45 (s, 4H), 1.28 (s, 1H). $^{13}$C NMR (125 MHz, CDCl$_3$): δ 203.9, 173.8, 170.9, 155.1, 154.1, 154.0, 127.6, 127.4, 114.6, 111.5, 104.3, 87.3, 76.6, 55.1, 52.5, 52.4, 46.9, 46.4, 46.3, 44.9, 43.4, 40.8, 32.4, 31.8, 24.5, 23.2.

Preparation of Platensimycin (1)

Platensimycin methyl ester (1e) (13 mg, 0.029 mmol) was dissolved in 1,4-dioxane (0.3 mL) and 2 N KOH (0.2 mL) was added to the solution, and the mixture was heated at 35° C. for 12 h. The reaction mixture was treated with 2 N HCl (0.3 mL) and extracted with CHCl$_3$ (5 mL×5). The combined organic portions dried over Na$_2$SO$_4$, filtered and concentrated. The residue was purified by flash column chromatography (EtOAc:hexanes:MeOH:H$_2$O:AcOH, 60:40:0.6:0.3:0.3) to give platensimycin (1) (8.0 mg, 63% yield).

R$_f$ 0.30 (EtOAc:hexanes:MeOH:H$_2$O:AcOH, 80:20:1:0.5:0.5). $^1$H NMR (500 MHz, pyridine): δ 10.42 (s, 1H), 8.00 (d, J=8.8 Hz, 1H), 6.76 (d, J=8.8 Hz, 1H), 6.25 (d, J=10.1 Hz, 1H), 5.82 (d, J=10.0 Hz, 1H), 4.37 (s, 1H), 2.78 2.52 (m, 3H), 2.33 (s, 1H), 2.08 (s, 1H), 1.93 (s, 1H), 1.78 (s, 1H), 1.69 (d, J=11.6 Hz, 2H), 1.61 (d, J=10.9 Hz, 1H), 1.45 (s, 1H), 1.36 (d, J=10.8 Hz, 1H), 1.28 (s, 3H), 1.02 (s, 3H). $^{13}$C NMR (125 MHz, pyridine): δ 203.5, 175.1, 174.7, 158.7, 158.4, 154.3, 129.7, 127.5, 115.6, 110.3, 107.4, 87.1, 76.8, 55.3, 47.0, 46.9, 46.4, 45.3, 43.3, 41.1, 32.4, 32.1, 24.8, 23.6.

EXAMPLE 9 TO 16

Preparation of Platensimycin Derinatives

Example 9

Preparation of (11S)-methylplatensimycin (2)

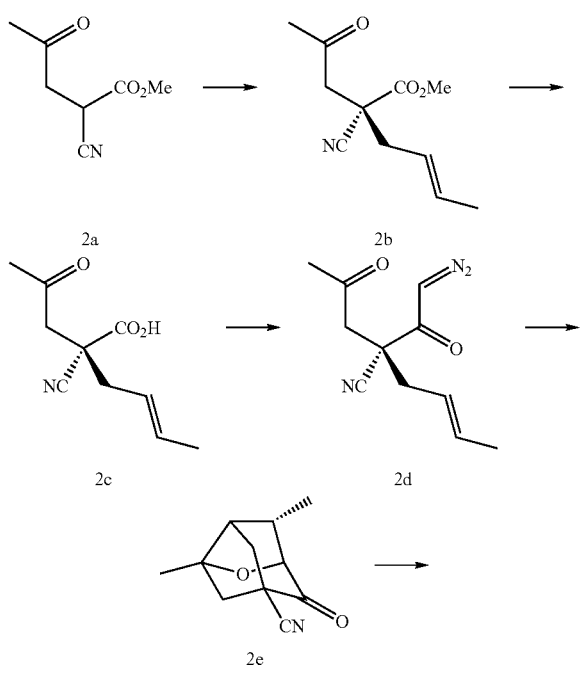

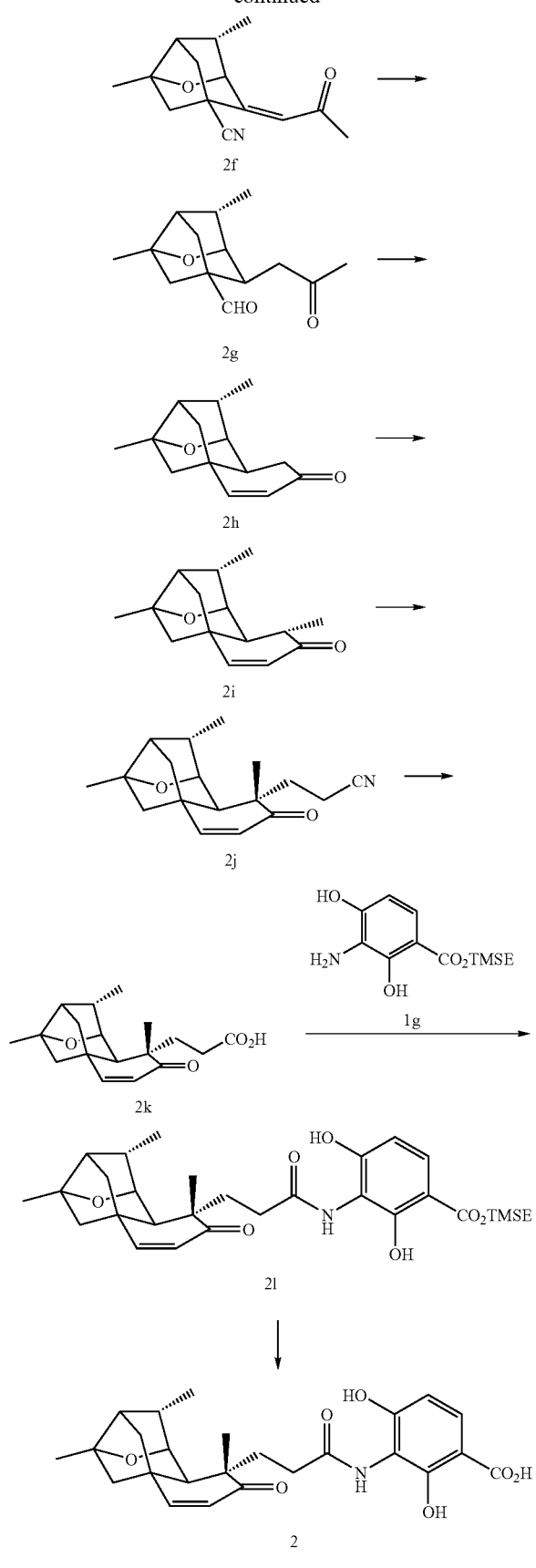

Preparation of Diazoketone (2d)

Ester (2a) (570 mg, 3.7 mmol) was added to a solution of sodium hydride (60% dispersion in mineral oil, 162 mg, 4.1 mmol) in THF (20 mL) at 0° C. The mixture was stirred for 10 min before the addition of crotyl bromide (85%, 0.53 mL, 4.4 mmol, E:Z=5:1) and warmed to r.t. After 2 h, the reaction was quenched by addition of sat. $NH_4Cl$ solution (20 mL), and the reaction mixture was extracted with $Et_2O$ (100 mL×2). The organic phase was washed with brine (50 mL), dried over $MgSO_4$, filtered and concentrated. Purification of the residue by flash column chromatography (hexanes-EtOAc, 3:1) gave methyl ester (2b) (613 mg, 80%, E:Z=5:1).

$R_f$ 0.37 (hexanes-EtOAc, 2:1). $^1H$ NMR (500 MHz, $CDCl_3$): δ 5.72 5.60 (m, 1H), 5.50 5.39 (m, 1H), 3.83 (s, 3H), 3.14 and 2.97 (ABq, J=18.3 Hz, 2H), 2.56 and 2.47 (ABX, $J_{AB}$=16.5, $J_{AX}$=7.3, $J_{BX}$=7.5 Hz, 2H), 2.19 (s, 3H), 1.72 (dd, J=0.8, 6.5 Hz, 3H). $^{13}C$ NMR (125 MHz, $CDCl_3$): δ 203.3, 169.2, 132.6, 130.6, 122.6, 121.7, 118.8, 53.8, 53.7, 49.0, 48.9, 45.1, 44.7, 40.3, 34.3, 29.5, 18.1, 13.2.

Methyl ester (2b) (613 mg, 2.9 mmol) was dissolved in MeOH (20 mL) and 1 N KOH solution (10 mL) was added to the solution at 0° C. The reaction mixture was stirred for 10 min at r.t. and treated slowly with 2 N HCl (10 mL) at 0° C. After extraction with EtOAc (100 mL×2), the organic phase was dried over $MgSO_4$, filtered and concentrated. The residue was dissolved in toluene (10 mL) and evaporated to provide the crude acid (2c) (570 mg, quant.) which was used in the next step without further purification.

TEA (0.61 mL, 4.4 mmol) was added to the solution of the crude acid (2c) (570 mg, 2.9 mmol) in THF (15 mL) at −20° C. and the mixture was treated with isobutyl chloroformate (0.53 mL, 4.1 mmol). After 30 min, an ethereal solution of diazomethane, which was prepared by the reaction of Diazald (3.8 g, 17 mmol) with KOH (3.8 g, 68 mmol), was slowly added to the reaction mixture, and the mixture was allowed to warm to 0° C. After stirring the reaction mixture at 0° C. for 2 h, excess diazomethane was decomposed by careful addition of acetic acid. The reaction mixture was filtered through a short column of silica gel with the aid of $Et_2O$ and concentrated. The residue was purified by flash column chromatography (hexanes-EtOAc, 4:1) to provide diazoketone (2d) (563 mg, 89%, two steps, E:Z=5:1). $R_f$ 0.38 (hexanes-EtOAc, 2:1).

Preparation of Enone (2f)

$Rh_2(OAc)_4$ (34 mg, 0.077 mmol) was added to a solution of diazoketone (2d) (560 mg, 2.6 mmol) in $CH_2Cl_2$ (250 mL). After stirring for 10 h, the reaction mixture was filtered through a short column of silica gel with the aid of hexanes-EtOAc (1:1) to remove the catalyst, and the filtrate was concentrated in vacuo. The residue was purified by flash column chromatography (hexanes-acetone-$CH_2Cl_2$, 4:1:1) to provide ketone (2e) (270 mg, 55%). $R_f$ 0.21 (hexanes-acetone-$CH_2Cl_2$, 4:1:1).

Dimethyl 2-oxopropylphosphonate (0.21 mL, 1.5 mmol) was added to a stirred suspension of anhydrous LiCl (119 mg, 2.8 mmol) and DIPEA (0.37 mL, 2.1 mmol) in anhydrous MeCN (15 mL) at 0° C. After 15 min, a solution of (2e) (270 mg, 1.4 mmol) in anhydrous MeCN (2 mL) was added to the mixture and the reaction mixture was stirred for 2 h at r.t. before dilution with $Et_2O$ (100 mL). The organic phase was washed with brine (20 mL×2), dried over $MgSO_4$, filtered and concentrated. The residue was purified by flash column chromatography (hexanes-EtOAc, 5:1) to give enone (2f) (160 mg, 49%).

$R_f$ 0.61 (hexanes-EtOAc, 2:1). $^1$H NMR (500 MHz, CDCl$_3$): δ 6.43 (s, 1H), 5.47 (s, 1H), 2.46 2.32 (m, 2H), 2.28 (s, 3H), 2.22 (dd, J=0.8, 6.6 Hz, 1H), 2.11 1.99 (m, 3H), 1.49 (s, 3H), 1.09 (d, J=6.9 Hz, 3H). $^{13}$C NMR (125 MHz, CDCl$_3$): δ 198.3, 150.0, 121.4, 118.9, 85.9, 79.7, 53.3, 50.8, 49.9, 48.4, 45.4, 32.0, 23.4, 17.9.

Preparation of Aldehyde (2g)

Dimethylphenylsilane (0.21 mL, 1.4 mmol) was added to a solution of enone (2f) (160 mg, 0.69 mmol) and (Ph$_3$P)$_3$RhCl (13 mg, 0.014 mmol) in toluene (1.4 mL) at r.t. The reaction mixture was stirred for 1 h at 60° C. and cooled to −40° C. After slow addition of DIBAL (1M in toluene, 2.8 mL, 2.8 mmol), the reaction mixture was stirred for 1 h and carefully quenched by addition of AcOH—H$_2$O (1:1) solution (4 mL). The mixture was stirred vigorously at 0° C. for 1 h and diluted with EtOAc (30 mL). The mixture was washed with brine (5 mL×2), dried over Na$_2$SO$_4$, filtered and concentrated. This crude mixture was dissolved in THF (7 mL) before dropwise addition of 2 N HCl (0.1 mL) at 0° C. The mixture was stirred at 0° C. for 1 h and diluted with EtOAc (30 mL), washed with brine (5 mL), dried over Na$_2$SO$_4$, filtered and concentrated. The residue was purified by flash column chromatography (hexanes-acetone, 6:1) to give aldehyde (2g) (86 mg, 53%).

$R_f$ 0.41 (hexanes-acetone, 3:1). $^1$H NMR (500 MHz, CDCl$_3$): δ 9.34 (s, 1H), 3.88 (d, J=3.1 Hz, 1H), 2.89 2.82 (m, 1H), 2.60 (dd, J=5.2, 17.3 Hz, 1H), 2.18 (dd, J=5.6, 15.5 Hz, 1H), 2.16 (s, 3H), 2.06 2.00 (m, 2H), 1.95 (dd, J=3.5, 11.1 Hz, 1H), 1.88 (ddd, J=1.8, 6.9, 12.0 Hz, 1H), 1.72 (dd, J=3.6, 12.1 Hz, 1H), 1.61 (d, J=11.1 Hz, 1H), 1.46 (s, 3H), 0.99 (d, J=6.8 Hz, 3H). $^{13}$C NMR (125 MHz, CDCl$_3$): δ 206.6, 202.7, 85.6, 83.5, 58.6, 50.9, 48.0, 44.8, 42.4, 38.2, 36.4, 30.4, 24.1, 18.4.

Preparation of Cyclic Enone (2h)

p-TsOH monohydrate (10 mol %, 7 mg) was added to a solution of aldehyde (2g) (86 mg, 0.36 mmol) in toluene (7 mL) and the mixture was heated under reflux for 2 h with concomitant removal of water (Dean-Stark trap). After cooling to r.t., the mixture was diluted with Et$_2$O (20 mL), washed with sat. NaHCO$_3$ solution (3 mL), dried over MgSO$_4$, filtered and concentrated. Flash column chromatography (hexanes-acetone, 8:1) provided cyclic enone (2h) (66 mg, 83%).

$R_f$ 0.46 (hexanes-acetone, 3:1). $^1$H NMR (500 MHz, CDCl$_3$): δ 6.60 (d, J=10.0 Hz, 1H), 5.93 (d, J=10.0 Hz, 1H), 3.80 (d, J=2.5 Hz, 1H), 2.50 2.37 (m, 1H), 2.36 2.32 (m, 2H), 2.15 (d, J=6.9 Hz, 1H), 1.99 (d, J=6.4 Hz, 1H), 1.90 (dd, J=3.3, 11.1 Hz, 1H), 1.83 1.71 (m, 2H), 1.60 (d, J=11.2 Hz, 1H), 1.56 (s, 3H), 1.46 (s, 3H), 1.03 (d, J=6.9 Hz, 3H). $^{13}$C NMR (125 MHz, CDCl$_3$): δ 199.1, 155.0, 128.8, 86.8, 83.6, 51.8, 50.6, 45.7, 43.8, 43.5, 42.7, 37.7, 24.1, 18.1.

Preparation of Enone (2i)

KHMDS (0.5 M solution in toluene, 1.1 mL, 0.55 mmol) was added to a solution of enone (2h) (61 mg, 0.28 mmol) in THF (6 mL) and HMPA (1.2 mL) at −78° C. The reaction mixture was allowed to stir at −78° C. for 30 min, after which MeI (0.15 mL, 2.2 mmol) was added. The reaction mixture was stirred at −10° C. for 1 h. The reaction mixture was quenched with sat. NH$_4$Cl solution (5 mL) and extracted with ether (2×30 mL). The combined organic extracts were washed with brine (2×5 mL), dried over anhydrous Na$_2$SO$_4$, filtered and concentrated. The residue was purified by flash column chromatography (hexanes-acetone, 14:1) to give enone (2i) (56 mg, 86%).

$R_f$ 0.63 (hexanes-acetone, 3:1). $^1$H NMR (500 MHz, CDCl$_3$): δ 6.53 (d, J=10.0 Hz, 1H), 5.91 (d, J=10.0 Hz, 1H), 4.00 (d, J=2.6 Hz, 1H), 2.39 (dq, J=6.7, 13.4 Hz, 1H), 2.17 2.08 (m, 2H), 2.04 1.97 (m, 1H), 1.90 1.82 (m, 2H), 1.74 (ddd, J=1.5, 6.8, 11.7 Hz, 1H), 1.56 (d, J=10.8 Hz, 1H), 1.46 (s, 3H), 1.12 (d, J=6.7 Hz, 3H), 1.06 (d, J=6.9 Hz, 3H). $^{13}$C NMR (125 MHz, CDCl$_3$): δ 201.5, 154.2, 128.3, 86.8, 82.5, 52.1, 51.0, 49.5, 46.5, 43.7, 43.2, 41.1, 24.3, 18.4, 11.2.

Preparation of Enone (2j)

Enone (2i) (14 mg, 0.060 mmol) was dissolved in t-BuOH (0.6 mL) and 40% KOH solution (0.0010 mL, 0.012 mmol) was added to the solution. The reaction mixture was allowed to stir at 60° C. for 5 min, after which acrylonitrile (0.03 mL, 0.91 mmol) was slowly added over 2 h at 60° C. The reaction mixture was stirred at 60° C. for 12 h. The reaction mixture was quenched with sat. NH$_4$Cl solution (2 mL) and extracted with ether (2×5 mL). The combined organic extracts were washed with brine (2×2 mL), dried over anhydrous Na$_2$SO$_4$, filtered and concentrated. The residue was purified by flash column chromatography (hexanes-acetone, 7:1) to give enone (2j) (13 mg, 76%).

$R_f$ 0.37 (hexanes-acetone, 3:1). $^1$H NMR (500 MHz, CDCl$_3$): δ 6.49 (d, J=10.1 Hz, 1H), 5.88 (d, J=10.1 Hz, 1H), 4.00 (s, 1H), 2.40 2.23 (m, 5H), 2.14 2.04 (m, 2H), 1.85 1.74 (m, 3H), 1.57 (d, J=11.2 Hz, 1H), 1.45 (s, 3H), 1.23 (s, 3H), 1.07 (d, J=6.8 Hz, 3H). $^{13}$C NMR (125 MHz, CDCl$_3$): δ 202.7, 154.0, 127.1, 119.8, 87.1, 81.3, 55.1, 51.2, 47.2, 47.0, 46.5, 45.8, 43.9, 31.8, 24.3, 24.2, 18.7, 12.9.

Preparation of Carboxylic Acid (2k)

Enone (2j) (21 mg, 0.073 mmol) was dissolved in MeOH (0.6 mL) and 20% KOH solution (3.5 mL) was added to the solution. The reaction mixture was heated under reflux for 2 h. After cooling to r.t., the reaction mixture was treated with 2 N HCl (10 mL) and extracted with EtOAc (30 mL×2). The combined organic extracts were washed with brine (2×10 mL), dried over anhydrous Na$_2$SO$_4$, filtered and concentrated. The residue was purified by flash column chromatography (CHCl$_3$-MeOH, 20:1) to give carboxylic acid (2k) (22 mg, 98%).

$R_f$ 0.42 (CHCl$_3$-MeOH, 3:1). $^1$H NMR (500 MHz, CDCl$_3$): δ 6.46 (d, J=10.1 Hz, 1H), 5.88 (d, J=10.1 Hz, 1H), 4.09 (s, 1H), 2.41 2.21 (m, 5H), 2.11 2.02 (m, 2H), 1.86 1.69 (m, 3H), 1.55 (d, J=11.1 Hz, 1H), 1.46 (s, 3H), 1.23 (s, 3H), 1.05 (d, J=6.8 Hz, 3H). $^{13}$C NMR (125 MHz, CDCl$_3$): δ 203.6, 178.1, 153.7, 127.4, 87.1, 81.5, 55.2, 51.3, 47.1, 46.9, 46.6, 45.8, 44.0, 30.8, 29.3, 24.9, 24.2, 18.6.

Preparation of (11S)-methylplatensimycin TMSE ester (2l)

TEA (0.032 mL, 0.23 mmol) and HATU (68 mg, 0.17 mmol) were added to a solution of carboxylic acid (2k) (17 mg, 0.056 mmol) and aniline (1g) (47 mg, 0.17 mmol) in DMF (0.2 mL) at room temperature. The reaction mixture was stirred at 24° C. for 15 h, after which brine (0.2 mL) was added. The resulting mixture was extracted with ether (4×5 mL), and the combined organic portions dried over Na$_2$SO$_4$. Concentration followed by flash column chromatography (hexanes-acetone, 8:1) afforded (11S)-methylplatensimycin TMSE ester (2l) (14 mg, 44%).

$R_f$ 0.34 (hexanes-acetone, 3:1). $^1$H NMR (500 MHz, CDCl$_3$): δ 11.81 (s, 1H), 11.05 (s, 1H), 8.09 (s, 1H), 7.56 (d, J=8.9 Hz, 1H), 6.50 (d, J=8.9 Hz, 1H), 6.50 (d, J=10.1 Hz, 1H), 5.92 (d, J=10.1 Hz, 1H), 4.48 4.34 (m, 2H), 4.10 (s, 0H), 2.53 (ddd, J=5.5, 12.2, 14.8 Hz, 1H), 2.44 2.25 (m, 5H), 2.14 2.07 (m, 2H), 1.95 1.76 (m, 4H), 1.58 (d, J=11.1 Hz, 2H), 1.47 (s, 3H), 1.27 (s, 3H), 1.16 1.10 (m, 2H), 1.07 (d, J=6.8 Hz, 3H), 0.9 (s, 9H). $^{13}$C NMR (125 MHz, CDCl$_3$): δ 203.7, 173.6, 170.5, 154.6, 153.9, 153.7, 127.3, 127.1, 114.3, 111.1, 104.4, 86.8, 81.2, 63.7, 55.0, 51.1, 47.0, 46.9, 46.7, 45.7, 43.7, 32.1, 31.6, 24.5, 24.0, 18.4, 17.4, −1.5.

Preparation of (11S)-methylplatensimycin (2)

Tris(dimethylamino)sulfonium difluorotrimethylsilicate (12 mg, 0.043 mmol) was added to a stirred solution of (11S)-methylplatensimycin TMSE ester (2l) (12.5 mg, 0.022 mmol) in DMF (0.3 mL), and the mixture was heated at 40° C. for 50 min. The solution was then cooled to r.t. and brine (0.5 mL) added. The mixture was extracted with CHCl$_3$ (5×5 mL) and the combined organic portions dried over Na$_2$SO$_4$. Concentration followed by flash column chromatography (EtOAc:hexanes:MeOH:H$_2$O:AcOH, 60:40:0.6:0.3:0.3) afforded synthetic (11S)-methylplatensimycin (2) (8.9 mg, 93% yield).

R$_f$ 0.31 (EtOAc:hexanes:MeOH:H$_2$O:AcOH, 80:20:1:0.5: 0.5). $^1$H NMR (500 MHz, CDCl$_3$): δ 11.77 (s, 1H), 11.14 (s, 1H), 8.10 (s, 1H), 7.69 (d, J=8.9 Hz, 1H), 6.54 (d, J=10.1 Hz, 1H), 6.50 (d, J=8.9 Hz, 1H), 5.95 (d, J=10.1 Hz, 1H), 4.34 (s, 1H), 2.74 2.62 (m, 1H), 2.56 2.44 (m, 3H), 2.36 (q, J=6.8 Hz, 1H), 2.21 2.11 (m, 2H), 1.95 1.78 (m, 3H), 1.63 (d, J=11.4 Hz, 1H), 1.54 (s, 3H), 1.30 (s, 3H), 1.10 (d, J=6.8 Hz, 3H). $^{13}$C NMR (125 MHz, CDCl$_3$): δ 203.7, 173.4, 172.2, 155.0, 154.1, 153.7, 128.2, 127.2, 114.3, 111.1, 103.8, 88.0, 81.5, 54.8, 51.2, 46.8, 46.6, 46.6, 45.7, 43.5, 31.3, 31.1, 24.7, 23.7, 18.3.

Example 10

Preparation of (11S)-bromoplatensimycin (3)

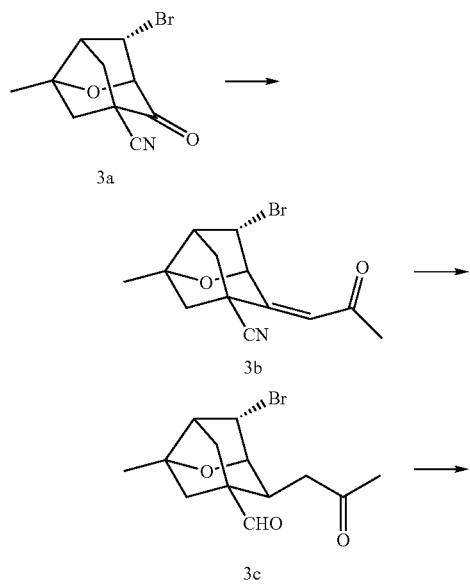

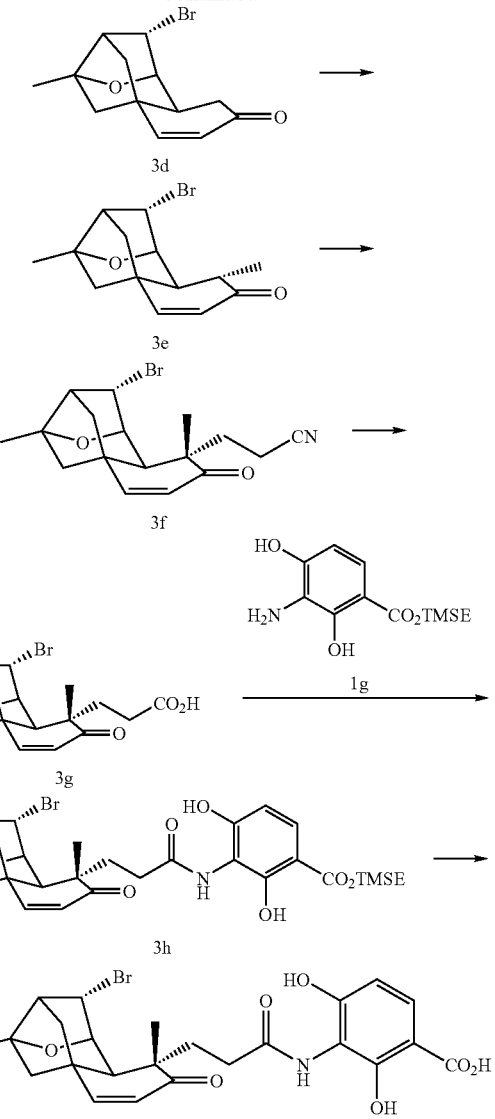

Preparation of Enone (3b)

Dimethyl 2-oxopropylphosphonate (0.59 mL, 4.3 mmol) was added to a stirred suspension of anhydrous LiCl (330 mg, 7.8 mmol) and DIPEA (1.0 mL, 0.57 mmol) in anhydrous MeCN (35 mL) at 0° C. After 15 min, a solution of (3a) (1.0 g, 3.9 mmol) in anhydrous MeCN (4 mL) was added to the mixture and the reaction mixture was stirred for 2 h at r.t. before dilution with Et$_2$O (200 mL). The organic phase was washed with brine (30 mL×2), dried over MgSO$_4$, filtered and concentrated. The residue was purified by flash column chromatography (hexanes-EtOAc, 3:1) to give enone (3b) (840 mg, 73%).

R$_f$ 0.49 (hexanes-EtOAc, 2:1). $^1$H NMR (500 MHz, CDCl$_3$): δ 6.50 (s, 1H), 5.79 (s, 1H), 4.18 (s, 1H), 2.87 (dd, J=1.5 Hz, 7.2, 1H), 2.51 2.42 (m, 2H), 2.31 (s, 3H), 2.14 2.05 (m, 2H), 1.62 (s, 3H). $^{13}$C NMR (125 MHz, CDCl$_3$): δ 197.7, 146.4, 123.5, 118.1, 86.7, 80.2, 56.6, 53.5, 52.9, 47.8, 44.8, 31.9, 23.1.

Preparation of Aldehyde (3c)

Dimethylphenylsilane (0.58 mL, 3.8 mmol) was added to a solution of enone (3b) (560 mg, 1.9 mmol) and (Ph$_3$P)$_3$RhCl (35 mg, 0.038 mmol) in toluene (3.8 mL) at r.t. The reaction mixture was stirred for 1 h at 60° C. and cooled to −40° C. After slow addition of DIBAL (1M in toluene, 7.6 mL, 7.6 mmol), the reaction mixture was stirred for 1 h and carefully quenched by addition of AcOH—H$_2$O (1:1) solution (10 mL). The mixture was stirred vigorously at 0° C. for 1 h and diluted with EtOAc (50 mL). The mixture was washed with brine (10 mL×2), dried over Na$_2$SO$_4$, filtered and concentrated. This crude mixture was dissolved in THF (10 mL) before dropwise addition of 2 N HCl (0.25 mL) at 0° C. The mixture was stirred at 0° C. for 1 h and diluted with EtOAc (50 mL), washed with brine (10 mL), dried over Na$_2$SO$_4$, filtered and concentrated. The residue was purified by flash column chromatography (hexanes-acetone, 6:1) to give aldehyde (3c) (250 mg, 44%).

R$_f$ 0.29 (hexanes-acetone, 3:1).

Preparation of Cyclic Enone (3d)

p-TsOH monohydrate (10 mol %, 2 mg) was added to a solution of aldehyde (3c) (31 mg, 0.10 mmol) in toluene (2 mL) and the mixture was heated under reflux for 2 h with concomitant removal of water (Dean-Stark trap). After cooling to r.t., the mixture was diluted with Et$_2$O (10 mL), washed with sat. NaHCO$_3$ solution (3 mL), dried over MgSO$_4$, filtered and concentrated. Flash column chromatography (hexanes-acetone, 7:1) provided cyclic enone (3d) (27 mg, 93%).

R$_f$ 0.36 (hexanes-acetone, 3:1). $^1$H NMR (500 MHz, CDCl$_3$): δ 6.58 (d, J=10.0 Hz, 1H), 5.96 (dd, J=0.7, 10.0 Hz, 1H), 4.41 (s, 1H), 4.22 (s, 1H), 2.68 (dd, J=1.5, 7.2 Hz, 1H), 2.64 2.56 (m, 1H), 2.45 (dd, J=4.2, 16.6 Hz, 1H), 2.31 (dd, J=15.2, 16.6 Hz, 1H), 2.01 (dd, J=3.5, 11.4 Hz, 1H), 1.94 (dd, J=3.5, 12.7 Hz, 1H), 1.87 (ddd, J=2.1, 7.3, 12.8 Hz, 1H), 1.68 (d, J=11.4 Hz, 1H), 1.60 (s, 3H). $^{13}$C NMR (125 MHz, CDCl$_3$): δ 197.7, 153.7, 129.5, 87.7, 84.1, 56.2, 53.7, 51.6, 45.3, 44.5, 43.1, 37.5, 30.6, 23.9.

Preparation of Enone (3e)

KHMDS (0.5 M solution in toluene, 1.36 mL, 0.68 mmol) was added to a solution of enone (3d) (107 mg, 0.38 mmol) in THF (8.0 mL) and HMPA (1.6 mL) at −78° C. The reaction mixture was allowed to stir at −78° C. for 30 min, after which MeI (0.19 mL, 3.0 mmol) was added. The reaction mixture was stirred at −10° C. for 1 h. The reaction mixture was quenched with sat. NH$_4$Cl solution (5 mL) and extracted with ether (2×20 mL). The combined organic extracts were washed with brine (2×5 mL), dried over anhydrous Na$_2$SO$_4$, filtered and concentrated. The residue was purified by flash column chromatography (hexanes-acetone, 12:1) to give enone (3e) (77 mg, 69%).

R$_f$ 0.43 (hexanes-acetone, 3:1).

Preparation of Enone (3f)

Enone (3e) (58 mg, 0.20 mmol) was dissolved in t-BuOH (2.5 mL) and 40% KOH solution (0.0029 mL, 0.040 mmol) was added to the solution. The reaction mixture was allowed to stir at 60° C. for 5 min, after which acrylonitrile (0.065 mL, 1.0 mmol) was slowly added over 2 h at 60° C. The reaction mixture was stirred at 60° C. for 12 h. The reaction mixture was quenched with sat. NH$_4$Cl solution (2 mL) and extracted with ether (2×15 mL). The combined organic extracts were washed with brine (2×5 mL), dried over anhydrous Na$_2$SO$_4$, filtered and concentrated. The residue was purified by flash column chromatography (hexanes-acetone, 7:1) to give enone (3f) (53 mg, 78%).

R$_f$ 0.21 (hexanes-acetone, 3:1). $^1$H NMR (500 MHz, CDCl$_3$): δ 6.48 (d, J=10.1 Hz, 1H), 5.93 (d, J=10.1 Hz, 1H), 4.54 (s, 1H), 4.37 (s, 1H), 2.78 (d, J=7.4 Hz, 1H), 2.49 (s, 1H), 2.44 2.22 (m, 3H), 2.17 (dd, J=3.7, 12.8 Hz, 1H), 1.97 1.87 (m, 2H), 1.83 1.78 (m, 1H), 1.65 (d, J=11.4 Hz, 1H), 1.61 (s, 3H), 1.25 (s, 3H). $^{13}$C NMR (125 MHz, CDCl$_3$): δ 201.4, 152.5, 127.6, 119.4, 87.9, 81.7, 57.8, 57.8, 54.6, 53.9, 48.6, 46.3, 45.1, 44.3, 31.8, 24.5, 23.8, 12.9.

Preparation of Carboxylic Acid (3g)

Enone (3f) (53 mg, 0.15 mmol) was dissolved in MeOH (1.3 mL) and 20% KOH solution (7.6 mL) was added to the solution. The reaction mixture was heated under reflux for 2 h. After cooling to r.t., the reaction mixture was treated with 2 N HCl (8 mL) and extracted with EtOAc (30 mL×2). The combined organic extracts were washed with brine (2×10 mL), dried over anhydrous Na$_2$SO$_4$, filtered and concentrated. The residue was purified by flash column chromatography (CHCl$_3$-MeOH, 20:1) to give acid (3g) (44 mg, 79%).

R$_f$ 0.37 (CHCl$_3$-MeOH, 5:1). $^1$H NMR (500 MHz, CDCl$_3$): δ 6.45 (d, J=10.1 Hz, 1H), 5.92 (d, J=10.1 Hz, 1H), 4.56 (s, 1H), 4.42 (s, 1H), 2.76 (d, J=6.4 Hz, 1H), 2.57 (s, 1H), 2.38 2.21 (m, 3H), 2.17 (dd, J=3.0, 12.1 Hz, 1H), 1.94 (dd, J=3.6, 11.4 Hz, 1H), 1.87 (ddd, J=1.9, 7.4, 12.6 Hz, 1H), 1.75 (d, J=13.3 Hz, 1H), 1.63 (d, J=11.4 Hz, 1H), 1.60 (s, 3H), 1.24 (s, 3H). $^{13}$C NMR (125 MHz, CDCl$_3$): δ 202.3, 177.9, 152.2, 127.9, 87.8, 81.9, 58.1, 54.7, 54.0, 48.6, 46.3, 45.1, 44.4, 30.9, 29.2, 25.1, 23.8.

Preparation of (11S)-bromoplatensimycin TMSE ester (3h)

TEA (0.026 mL, 0.19 mmol) and HATU (57 mg, 0.14 mmol) were added to a solution of carboxylic acid (3g) (17 mg, 0.046 mmol) and aniline (1g) (39 mg, 0.14 mmol) in DMF (0.20 mL) at r.t. The reaction mixture was stirred at 24° C. for 15 h, after which brine (0.5 mL) was added. The resulting mixture was extracted with ether (4×5.0 mL), and the combined organic portions dried over Na$_2$SO$_4$. Concentration followed by flash column chromatography (hexanes-acetone, 8:1) afforded (11S)-bromoplatensimycin TMSE ester (3h) (12 mg, 42%).

R$_f$ 0.40 (hexanes-acetone, 3:1). $^1$H NMR (500 MHz, CDCl$_3$): δ 11.82 (s, 1H), 10.97 (s, 1H), 8.04 (s, 1H), 7.56 (d, J=8.9 Hz, 1H), 6.51 (d, J=9.0 Hz, 1H), 6.48 (d, J=10.1 Hz, 1H), 5.95 (d, J=10.1 Hz, 1H), 4.56 (s, 1H), 4.47 (s, 1H), 4.44 4.40 (m, 2H), 2.78 (dd, J=1.4, 7.4 Hz, 1H), 2.59 (t, J=2.2 Hz, 1H), 2.53 2.46 (m, 1H), 2.43 2.34 (m, 2H), 2.20 (dd, J=3.7, 12.8 Hz, 1H), 1.97 1.86 (m, 3H), 1.65 (d, J=11.4 Hz, 1H), 1.61 (s, 3H), 1.28 (s, 3H), 1.16 1.11 (m, 2H), 0.09 (s, 9H). $^{13}$C NMR (125 MHz, CDCl$_3$): δ 202.4, 173.1, 170.5, 154.6, 153.9, 152.2, 127.6, 127.4, 114.3, 111.2, 104.5, 87.6, 81.6, 63.8, 57.8, 54.5, 53.8, 48.6, 46.4, 45.0, 44.1, 32.1, 31.7, 24.7, 23.6, 17.4, −1.5.

Preparation of (11S)-bromoplatensimycin (3)

Tris(dimethylamino)sulfonium difluorotrimethylsilicate (5.2 mg, 0.019 mmol) was added to a stirred solution of (11S)-bromoplatensimycin TMSE ester (3h) (5.8 mg, 0.0094 mmol) in DMF (0.1 mL), and the mixture was heated at 40° C. for 50 min. The solution was then cooled to r.t. and brine (0.2 mL) added. The mixture was extracted with CHCl₃ (5×3 mL) and the combined organic portions dried over Na₂SO₄. Concentration followed by flash column chromatography (EtOAc:hexanes:MeOH:H₂O:AcOH, 60:40:0.6:0.3:0.3) afforded synthetic (11S)-bromoplatensimycin (3) (4.6 mg, 95% yield).

$R_f$ 0.21 (EtOAc:hexanes:MeOH:H₂O:AcOH, 80:20:1:0.5:0.5). ¹H NMR (500 MHz, CDCl₃): δ 11.71 (s, 1H), 8.13 (s, 1H), 7.62 (d, J=8.9 Hz, 1H), 6.53 (d, J=10.6 Hz, 1H), 6.51 (d, J=9.6 Hz, 1H), 5.99 (d, J=10.1 Hz, 1H), 4.59 (s, 1H), 4.58 (s, 1H), 2.82 (d, J=6.8 Hz, 1H), 2.66 (s, 1H), 2.62 2.52 (m, 1H), 2.52 2.42 (m, 2H), 2.23 (dd, J=3.3, 12.8 Hz, 1H), 2.03 1.97 (m, 1H), 1.96 1.86 (m, 2H), 1.69 (d, J=11.6 Hz, 1H), 1.65 (s, 3H), 1.31 (s, 3H). ¹³C NMR (125 MHz, CDCl₃): δ 203.1, 173.1, 172.5, 155.2, 154.2, 152.8, 128.3, 127.6, 114.2, 111.2, 103.6, 88.2, 81.6, 57.3, 54.4, 53.8, 48.3, 46.4, 45.0, 44.0, 31.6, 31.5, 24.8, 23.4.

Example 11

Preparation of (11S)-chloroplatensimycin (4)

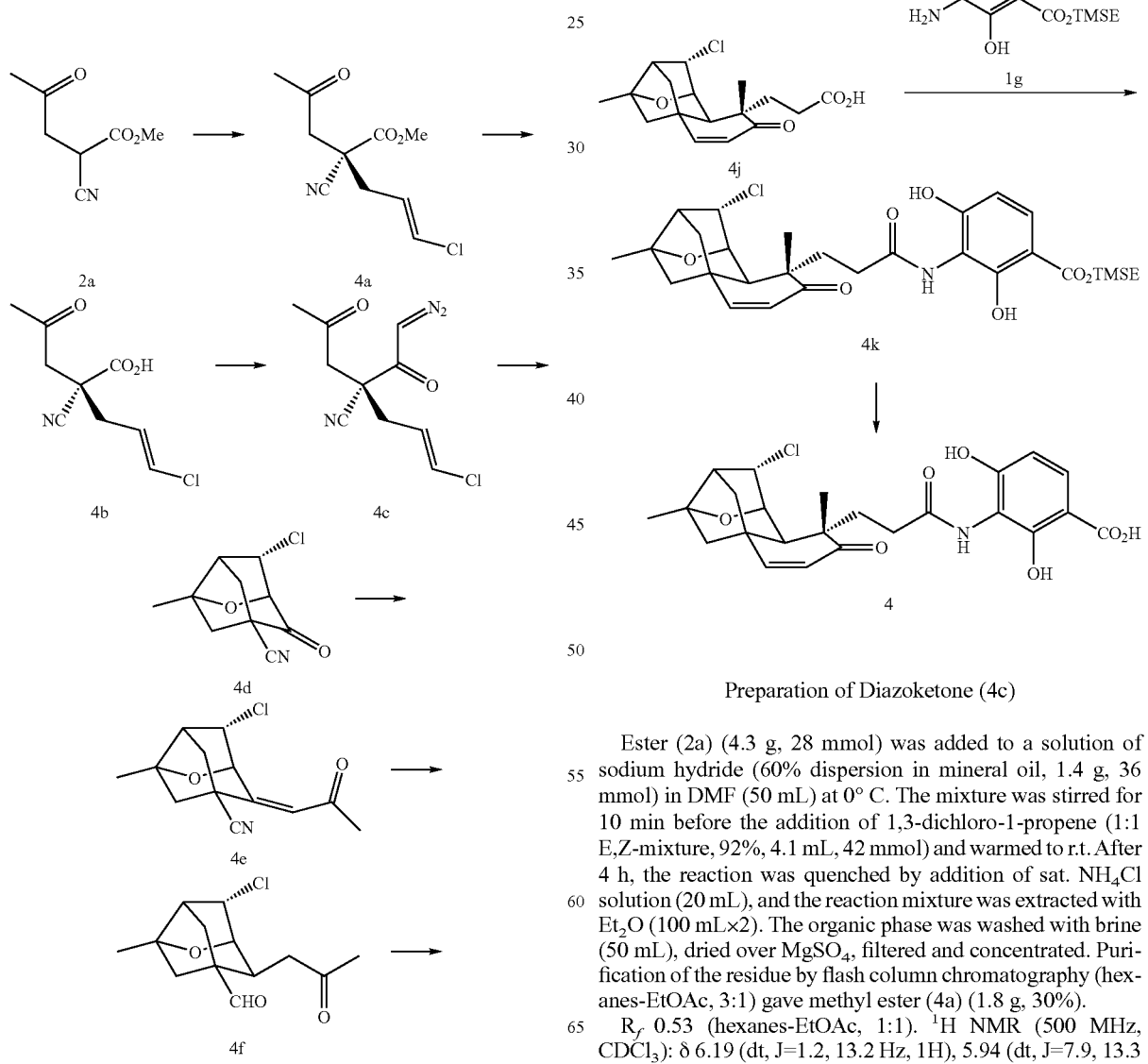

Preparation of Diazoketone (4c)

Ester (2a) (4.3 g, 28 mmol) was added to a solution of sodium hydride (60% dispersion in mineral oil, 1.4 g, 36 mmol) in DMF (50 mL) at 0° C. The mixture was stirred for 10 min before the addition of 1,3-dichloro-1-propene (1:1 E,Z-mixture, 92%, 4.1 mL, 42 mmol) and warmed to r.t. After 4 h, the reaction was quenched by addition of sat. NH₄Cl solution (20 mL), and the reaction mixture was extracted with Et₂O (100 mL×2). The organic phase was washed with brine (50 mL), dried over MgSO₄, filtered and concentrated. Purification of the residue by flash column chromatography (hexanes-EtOAc, 3:1) gave methyl ester (4a) (1.8 g, 30%).

$R_f$ 0.53 (hexanes-EtOAc, 1:1). ¹H NMR (500 MHz, CDCl₃): δ 6.19 (dt, J=1.2, 13.2 Hz, 1H), 5.94 (dt, J=7.9, 13.3 Hz, 1H), 3.85 (s, 3H), 3.16 and 3.02 (ABq, J=18.2 Hz, 2H), 2.67 2.56 (m, 2H), 2.21 (s, 3H). $^{13}$C NMR (125 MHz, CDCl$_3$): δ 202.7, 168.6, 125.5, 123.7, 118.2, 54.1, 48.9, 44.6, 38.1, 29.6.

Methyl ester (4a) (1.1 g, 5.1 mmol) was dissolved in MeOH (30 mL) and 1 N KOH solution (15 mL) was added to the solution at 0° C. The reaction mixture was stirred for 10 min at r.t. and treated slowly with 2 N HCl (8 mL) at 0° C. After extraction with EtOAc (100 mL×2), the organic phase was dried over MgSO$_4$, filtered and concentrated. The residue was dissolved in toluene (10 mL) and evaporated to provide the crude acid (4b) (1.0 g, quant.) which was used in the next step without further purification.

TEA (1.1 mL, 7.7 mmol) was added to the solution of the crude acid (4b) (1.0 g, 5.1 mmol) in THF (25 mL) at −20° C. and the mixture was treated with isobutyl chloroformate (0.98 mL, 7.7 mmol). After 30 min, an ethereal solution of diazomethane, which was prepared by the reaction of Diazald (6.6 g, 31 mmol) with KOH (6.6 g, 118 mmol), was slowly added to the reaction mixture, and the mixture was allowed to warm to 0° C. After stirring the reaction mixture for 1 h, excess diazomethane was decomposed by careful addition of acetic acid at 0° C. The reaction mixture was filtered through a short column of silica gel with the aid of Et$_2$O and concentrated. The residue was purified by flash column chromatography (hexanes-EtOAc, 4:1) to provide diazoketone (4c) (770 mg, 69%, two steps).

R$_f$ 0.31 (hexanes-EtOAc, 2:1). $^1$H NMR (500 MHz, CDCl$_3$): δ 6.20 (dt, J=1.2, 13.3 Hz, 1H), 6.08 (s, 1H), 5.92 (dt, J=8.0, 13.3 Hz, 1H), 3.27 and 2.89 (ABq, J=18.2 Hz, 2H), 2.62 2.43 (m, 2H), 2.18 (d, J=3.1 Hz, 3H). $^{13}$C NMR (125 MHz, CDCl$_3$): δ 202.8, 187.8, 125.5, 123.8, 119.7, 56.3, 49.0, 47.2, 38.5, 29.5.

Preparation of Enone (4e)

Rh$_2$(OAc)$_4$ (46 mg, 0.10 mmol) was added to a solution of diazoketone (4c) (770 mg, 3.4 mmol) in CH$_2$Cl$_2$ (350 mL). After stirring for 10 h, the reaction mixture was filtered through a short column of silica gel with the aid of hexanes-EtOAc (1:1) to remove the catalyst, and the filtrate was concentrated in vacuo. The residue was purified by flash column chromatography (hexanes-acetone-CH$_2$Cl$_2$, 4:1:1) to provide ketone (4d) (610 mg, 90%).

R$_f$ 0.16 (hexanes-acetone-CH$_2$Cl$_2$, 4:1:1).

Dimethyl 2-oxopropylphosphonate (0.17 mL, 1.2 mmol) was added to a stirred suspension of anhydrous LiCl (94 mg, 2.2 mmol) and DIPEA (0.29 mL, 1.7 mmol) in anhydrous MeCN (11 mL) at 0° C. After 15 min, a solution of ketone (4d) (220 mg, 1.1 mmol) in anhydrous MeCN (2 mL) was added to the mixture and the reaction mixture was stirred for 4 h at r.t. before dilution with Et$_2$O (100 mL). The organic phase was washed with brine (20 mL×2), dried over MgSO$_4$, filtered and concentrated. The residue was purified by flash column chromatography (hexanes-EtOAc, 3:1) to give enone (4e) (210 mg, 80%).

R$_f$ 0.50 (hexanes-EtOAc, 2:1). $^1$H NMR (500 MHz, CDCl$_3$): δ 6.52 (s, 1H), 5.76 (s, 1H), 4.13 (s, 1H), 2.76 (dd, J=1.5, 7.2 Hz, 1H), 2.48 (dd, J=3.4, 11.5 Hz, 1H), 2.44 (dd, J=7.3, 12.3 Hz, 1H), 2.31 (s, 3H), 2.11 (d, J=11.5 Hz, 1H), 2.03 (dd, J=3.3, 12.4 Hz, 1H), 1.59 (s, 3H). $^{13}$C NMR (125 MHz, CDCl$_3$): δ 197.7, 146.3, 123.7, 118.1, 86.6, 80.0, 67.0, 53.2, 52.6, 46.4, 44.7, 31.9, 22.9.

Preparation of Aldehyde (4f)

Dimethylphenylsilane (0.062 mL, 0.40 mmol) was added to a solution of enone (4e) (150 mg, 0.63 mmol) and (Ph$_3$P)$_3$RhCl (12 mg, 0.013 mmol) in toluene (1.3 mL) at r.t. The reaction mixture was stirred for 1 h at 60° C. and cooled to −40° C. After slow addition of DIBAL (1M in toluene, 2.5 mL, 2.5 mmol), the reaction mixture was stirred for 1 h and carefully quenched by addition of AcOH—H$_2$O (1:1) solution (4 mL). The mixture was stirred vigorously at 0° C. for 1 h and diluted with EtOAc (20 mL). The mixture was washed with brine (5 mL×2), dried over Na$_2$SO$_4$, filtered and concentrated. This crude mixture was dissolved in THF (3 mL) before dropwise addition of 2 N HCl (0.1 mL) at 0° C. The mixture was stirred at 0° C. for 1 h and diluted with EtOAc (20 mL), washed with brine (5 mL), dried over Na$_2$SO$_4$, filtered and concentrated. The residue was purified by flash column chromatography (hexanes-acetone, 5:1) to give aldehyde (40 (98 mg, 64%).

R$_f$ 0.19 (hexanes-acetone, 3:1). $^1$H NMR (500 MHz, CDCl$_3$): δ 9.36 (s, 1H), 7.26 (s, 1H), 4.23 (dd, J=1.8, 3.7 Hz, 1H), 4.17 (s, 1H), 3.04 2.99 (m, 1H), 2.62 2.55 (m, 2H), 2.20 (dd, J=6.9, 17.9 Hz, 1H), 2.17 (s, 3H), 2.07 (dd, J=3.6, 11.4 Hz, 1H), 2.02 1.96 (m, 1H), 1.80 (dd, J=3.6, 12.9 Hz, 1H), 1.66 (d, J=11.4 Hz, 1H), 1.56 (s, 3H). $^{13}$C NMR (125 MHz, CDCl$_3$): δ 205.4, 201.4, 86.2, 83.8, 66.1, 57.9, 53.5, 47.3, 41.7, 37.7, 36.8, 30.4, 23.5.

Preparation of Cyclic Enone (4g)

p-TsOH monohydrate (10 mol %, 8 mg) was added to a solution of aldehyde (40 (98 mg, 0.40 mmol) in toluene (8 mL) and the mixture was heated under reflux for 2 h with concomitant removal of water (Dean-Stark trap). After cooling to r.t., the mixture was diluted with Et$_2$O (20 mL), washed with sat. NaHCO$_3$ solution (3 mL), dried over MgSO$_4$, filtered and concentrated. Flash column chromatography (hexanes-acetone, 6:1) provided cyclic enone (4g) (68 mg, 76%).

R$_f$ 0.28 (hexanes-acetone, 3:1). $^1$H NMR (500 MHz, CDCl$_3$): δ 6.60 (d, J=10.0 Hz, 1H), 5.95 (dd, J=0.8, 10.0 Hz, 1H), 4.33 (s, 1H), 4.16 (dd, J=1.8, 3.0 Hz, 1H), 2.62 2.55 (m, 2H), 2.45 (dd, J=4.2, 16.6 Hz, 1H), 2.30 (dd, J=15.2, 16.6 Hz, 1H), 2.00 (dd, J=3.1, 11.4 Hz, 1H), 1.94 1.85 (m, 2H), 1.67 (d, J=11.4 Hz, 1H), 1.57 (s, 3H). $^{13}$C NMR (125 MHz, CDCl$_3$): δ 197.7, 153.7, 129.5, 87.6, 83.8, 65.7, 53.4, 51.3, 45.2, 44.3, 42.1, 37.4, 23.7.

Preparation of Enone (4h)

KHMDS (0.5 M solution in toluene, 0.68 mL, 0.34 mmol) was added to a solution of enone (4g) (38 mg, 0.17 mmol) in THF (3.5 mL) and HMPA (0.7 mL) at −78° C. The reaction mixture was allowed to stir at −78° C. for 30 min, after which MeI (0.08 mL, 1.4 mmol) was added. The reaction mixture was stirred at −10° C. for 1 h. The reaction mixture was quenched with sat. NH$_4$Cl solution (3 mL) and extracted with ether (2×10 mL). The combined organic extracts were washed with brine (2×5 mL), dried over anhydrous Na$_2$SO$_4$, filtered and concentrated. The residue was purified by flash column chromatography (hexanes-acetone, 10:1) to give enone (4h) (17 mg, 42%).

R$_f$ 0.39 (hexanes-acetone, 3:1).

Preparation of Enone (4i)

Enone (4h) (22 mg, 0.117 mmol) was dissolved in t-BuOH (0.5 mL) and 40% KOH solution (0.26 mL, 0.13 mmol) was added to the solution. The reaction mixture was allowed to stir at 60° C. for 5 min, after which acrylonitrile (0.06 mL, 0.935 mmol) was slowly added over 2 h at 60° C. The reaction mixture was stirred at 60° C. for 12 h. The reaction mixture was quenched with sat. NH₄Cl solution (2 mL) and extracted with ether (2×5 mL). The combined organic extracts were washed with brine (2×2 mL), dried over anhydrous Na₂SO₄, filtered and concentrated. The residue was purified by flash column chromatography (hexanes-acetone, 6:1) to give enone (4i) (16 mg, 68%).

$R_f$ 0.21 (hexanes-acetone, 3:1). ¹H NMR (500 MHz, CDCl₃): δ 6.49 (d, J=10.1 Hz, 1H), 5.93 (d, J=10.1 Hz, 1H), 4.46 (s, 1H), 4.32 (s, 1H), 2.66 (d, J=7.4 Hz, 1H), 2.47 (s, 1H), 2.43 2.24 (m, 3H), 2.14 (dd, J=3.6, 12.8 Hz, 1H), 1.96 1.88 (m, 2H), 1.85 1.76 (m, 1H), 1.67 (d, J=11.4 Hz, 1H), 1.58 (s, 3H), 1.25 (s, 3H). ¹³C NMR (125 MHz, CDCl₃): δ 201.5, 152.4, 127.6, 119.3, 87.7, 81.5, 67.4, 54.4, 53.6, 48.4, 46.2, 45.1, 43.4, 31.8, 24.5, 23.6, 12.9.

Preparation of Carboxylic Acid (4j)

Enone (4i) (14 mg, 0.046 mmol) was dissolved in MeOH (0.5 mL) and 20% KOH solution (2.3 mL) was added to the solution. The reaction mixture was heated under reflux for 2 h. After cooling to r.t., the reaction mixture was treated with 2 N HCl (8 mL) and extracted with EtOAc (20 mL×2). The combined organic extracts were washed with brine (2×5 mL), dried over anhydrous Na₂SO₄, filtered and concentrated. The residue was purified by flash column chromatography (CHCl₃-MeOH, 20:1) to give acid (4j) (12 mg, 81%).

$R_f$ 0.33 (CHCl₃-MeOH, 10:1). ¹H NMR (500 MHz, CDCl₃): δ 6.47 (d, J=10.1 Hz, 1H), 5.92 (d, J=10.1 Hz, 1H), 4.48 (s, 1H), 4.39 (s, 1H), 2.63 (d, J=6.4 Hz, 1H), 2.56 (s, 1H), 2.35 2.20 (m, 3H), 2.13 (dd, J=3.5, 12.7 Hz, 1H), 1.94 (dd, J=3.4, 11.4 Hz, 1H), 1.91 1.85 (m, 1H), 1.78 (t, J=9.6 Hz, 1H), 1.62 (d, J=11.4 Hz, 1H), 1.57 (s, 3H), 1.23 (s, 3H). ¹³C NMR (125 MHz, CDCl₃): δ 202.3, 177.8, 151.9, 127.8, 87.4, 81.5, 67.5, 54.2, 53.5, 48.1, 46.2, 44.8, 43.2, 30.8, 29.4, 25.0, 23.5.

Preparation of (11S)-chloroplatensimycin TMSE ester (4k)

TEA (0.022 mL, 0.16 mmol) and HATU (47 mg, 0.12 mmol) were added to a solution of carboxylic acid (4j) (12 mg, 0.037 mmol) and aniline (1g) (32 mg, 0.12 mmol) in DMF (0.2 mL) at room temperature. The reaction mixture was stirred at 24° C. for 15 h, after which brine (0.2 mL) was added. The resulting mixture was extracted with ether (4×5 mL), and the combined organic portions dried over Na₂SO₄. Concentration followed by flash column chromatography (hexanes-acetone, 8:1) afforded (11S)-chloroplatensimycin TMSE ester (4k) (8.0 mg, 38%).

$R_f$ 0.41 (hexanes-acetone, 3:1). ¹H NMR (500 MHz, CDCl₃): δ 11.82 (s, 1H), 10.97 (s, 1H), 8.05 (s, 1H), 7.56 (d, J=8.9 Hz, 1H), 6.51 (d, J=9.0 Hz, 1H), 6.50 (d, J=10.1 Hz, 1H), 5.95 (d, J=10.1 Hz, 1H), 4.48 (s, 1H), 4.46 4.38 (m, 3H), 2.66 (dd, J=1.4, 7.4 Hz, 1H), 2.57 (s, 1H), 2.51 (ddd, J=5.3, 11.7, 13.1 Hz, 1H), 2.44 2.34 (m, 2H), 2.17 (dd, J=3.6, 12.8 Hz, 1H), 1.97 1.88 (m, 3H), 1.65 (d, J=11.4 Hz, 1H), 1.58 (s, 3H), 1.27 (s, 3H), 1.15 1.10 (m, 2H), 0.09 (s, 9H). ¹³C NMR (125 MHz, CDCl₃): δ 202.4, 173.1, 170.5, 154.6, 153.9, 152.1, 127.7, 127.4, 114.3, 111.2, 104.5, 87.4, 81.4, 67.4, 63.8, 54.3, 53.5, 48.4, 46.4, 45.0, 43.2, 32.0, 31.7, 24.7, 23.5, 17.4, −0.0, −1.5.

Preparation of (11S)-chloroplatensimycin (4)

Tris(dimethylamino)sulfonium difluorotrimethylsilicate (6.7 mg, 0.024 mmol) was added to a stirred solution of (11S)-chloroplatensimycin TMSE ester (4k) (7.0 mg, 0.012 mmol) in DMF (0.2 mL), and the mixture was heated at 40° C. for 50 min. The solution was then cooled to r.t. and brine (0.2 mL) added. The mixture was extracted with CHCl₃ (5×3 mL) and the combined organic portions dried over Na₂SO₄. Concentration followed by flash column chromatography (EtOAc:hexanes:MeOH:H₂O:AcOH, 60:40:0.6:0.3:0.3) afforded synthetic (11S)-chloroplatensimycin (4) (5.4 mg, 93% yield).

$R_f$ 0.24 (EtOAc:hexanes:MeOH:H₂O:AcOH, 80:20:1:0.5:0.5). ¹H NMR (500 MHz, CDCl₃): δ 11.68 (s, 1H), 11.11 (s, 1H), 8.12 (s, 1H), 7.62 (d, J=8.9 Hz, 1H), 6.54 (d, J=10.1 Hz, 1H), 6.52 (d, J=9.0 Hz, 1H), 5.99 (d, J=10.1 Hz, 1H), 4.54 (s, 1H), 4.51 (s, 1H), 2.70 (d, J=6.0 Hz, 1H), 2.64 (s, 1H), 2.62 2.54 (m, 1H), 2.52 2.43 (m, 2H), 2.20 (dd, J=3.6, 12.8 Hz, 1H), 1.99 (dd, J=3.5, 11.6 Hz, 1H), 1.97 1.88 (m, 2H), 1.68 (d, J=11.5 Hz, 1H), 1.62 (s, 3H), 1.31 (s, 3H). ¹³C NMR (125 MHz, CDCl₃): δ 203.0, 173.1, 172.2, 155.3, 154.2, 152.6, 128.3, 127.7, 114.3, 111.3, 103.4, 88.0, 81.4, 67.1, 54.2, 53.5, 48.2, 46.4, 45.0, 43.1, 31.7, 31.6, 24.9, 23.3.

Example 12

Preparation of 7-methylplatensimycin (5)

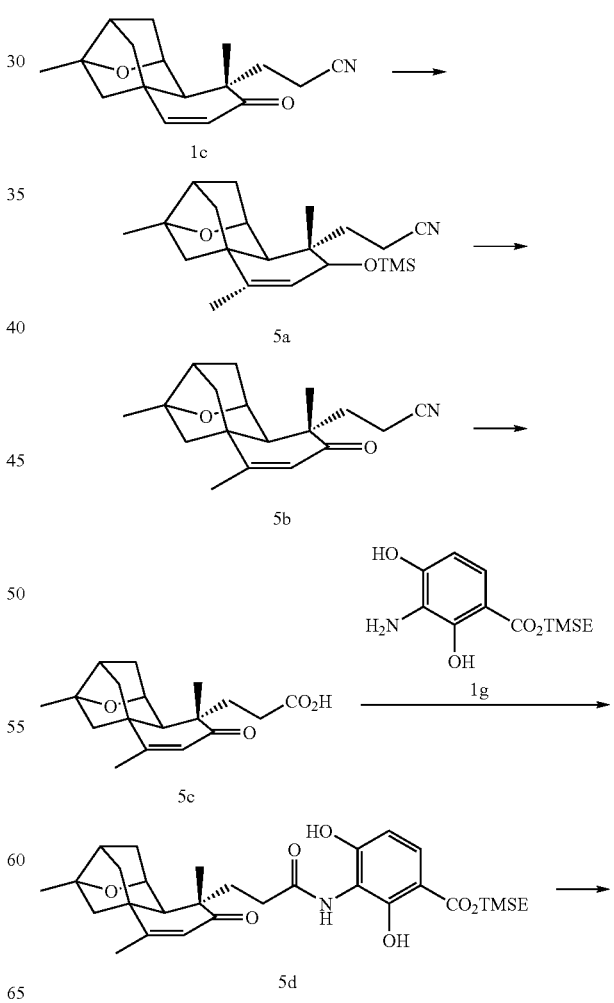

-continued

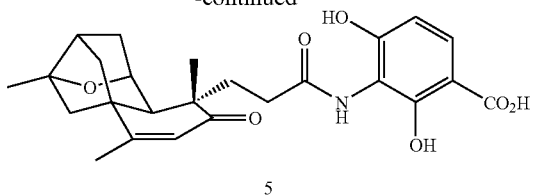

5

Preparation of Enone (5b)

To a lithium dimethylcuprate solution, separately prepared by the addition of methyllithium (2.4 M in diethoxymethane, 0.62 mL, 1.54 mmol) to a suspension of cuprous iodide (144 mg, 0.76 mmol) in diethylether (2.5 mL) at 0° C., trimethylsilyl chloride (0.089 mL, 0.73 mmol) and a solution of enone (1c) (21 mg, 0.077 mmol) in THF (0.5 mL) were slowly added over 20 min at −78° C. and the mixture was stirred −78° C. for 1 h. The reaction was quenched with TEA (0.12 mL) and sat. NH$_4$Cl solution (2 mL). The reaction mixture was extracted with diethyl ether (10 mL×2), washed with brine (2×5 mL), dried over anhydrous Na$_2$SO$_4$, filtered and concentrated. The residue was purified by flash column chromatography (hexanes-acetone, 20:1) to give silyl ether (5a) (26 mg, 94%).

R$_f$ 0.56 (hexanes-acetone, 3:1). $^1$H NMR (500 MHz, CDCl$_3$): δ 4.82 (d, J=6.0 Hz, 1H), 4.27 (t, J=3.4 Hz, 1H), 2.34 2.15 (m, 4H), 1.98 1.91 (m, 2H), 1.84 1.74 (m, 4H), 1.70 (ddd, J=5.4, 11.5, 13.4 Hz, 1H), 1.37 (s, 3H), 1.36 (d, J=19.6 Hz, 1H), 1.11 (s, 3H), 0.86 (d, J=7.0 Hz, 3H), 0.19 (s, 9H). $^{13}$C NMR (125 MHz, CDCl$_3$): δ 150.0, 120.3, 109.5, 85.8, 77.5, 51.9, 45.8, 45.1, 44.7, 42.9, 41.1, 38.8, 36.9, 35.9, 25.6, 23.2, 20.7, 13.2, 0.3.

To a stirred solution of DDQ (78 mg, 0.34 mmol) and HMDS (0.073 mL, 0.34 mmol) in dry benzene (1 mL), a solution of silyl ether (5a) (4.6 mg, 0.013 mmol) in dry benzene (0.5 mL) was added, and the resulting mixture was heated under reflux with stirring for 2 h. The reaction was quenched by the addition of saturated aqueous sodium hydrogen carbonate solution and the mixture was extracted with EtOAc (30 mL×2). The organic layer was washed with brine (2×10 mL), dried over anhydrous Na$_2$SO$_4$, filtered and concentrated. The residue was purified by flash column chromatography (hexanes-acetone, 6:1) to give enone (5b) (2.0 mg, 54%).

R$_f$ 0.29 (hexanes-acetone, 3:1). $^1$H NMR (500 MHz, CDCl$_3$): δ 5.83 (d, J=1.2 Hz, 1H), 4.34 (s, 1H), 2.45 2.41 (m, 1H), 2.39 2.28 (m, 2H), 2.28 2.25 (m, 1H), 2.24 2.22 (m, 1H), 2.14 2.07 (m, 1H), 2.06 (d, J=11.6 Hz, 1H), 1.98 1.95 (m, 2H), 1.88 (s, 1H), 1.85 (d, J=1.3 Hz, 3H), 1.81 1.71 (m, 2H), 1.47 (s, 3H), 1.23 (s, 3H). $^{13}$C NMR (125 MHz, CDCl$_3$): δ 201.3, 162.9, 126.6, 119.8, 86.8, 76.5, 52.5, 48.6, 46.6, 46.1, 44.8, 42.3, 41.1, 31.9, 24.3, 23.4, 17.7, 12.9.

Preparation of Carboxylic Acid (5c)

To a stirred solution of enone (5b) (12 mg, 0.042 mmol) in MeOH (0.4 mL) and THF (0.4 mL) was added 20% KOH solution (2 mL). The reaction mixture was heated under reflux for 2 h. After cooling to r.t., the reaction mixture was treated with 2 N HCl (6 mL) and extracted with EtOAc (20 mL×2). The combined organic extracts were washed with brine (2×5 mL), dried over anhydrous Na$_2$SO$_4$, filtered and concentrated. The residue was purified by flash column chromatography (CHCl$_3$-MeOH, 20:1) to give acid (5c) (12 mg, 94%).

R$_f$ 0.43 (CHCl$_3$-MeOH, 10:1). $^1$H NMR (500 MHz, CDCl$_3$): δ 5.83 (s, 1H), 4.40 (s, 1H), 2.41 (t, J=5.6 Hz, 1H), 2.36 2.20 (m, 4H), 2.12 2.02 (m, 2H), 1.99 1.91 (m, 2H), 1.87 (d, J=11.2 Hz, 1H), 1.84 (d, J=1.1 Hz, 3H), 1.79 1.69 (m, 2H), 1.46 (s, 3H), 1.22 (s, 3H). $^{13}$C NMR (125 MHz, CDCl$_3$): δ 202.3, 177.9, 162.5, 126.9, 86.8, 76.8, 52.5, 48.6, 46.5, 46.2, 44.9, 42.3, 41.0, 30.9, 29.3, 24.9, 23.4, 17.7.

Preparation of 7-methylplatensimycin TMSE ester (5d)

TEA (0.033 mL, 0.24 mmol) and HATU (70 mg, 0.18 mmol) were added to a solution of carboxylic acid (5c) (17 mg, 0.056 mmol) and aniline (1g) (48 mg, 0.18 mmol) in DMF (0.3 mL) at room temperature. The reaction mixture was stirred at 24° C. for 15 h, after which brine (0.3 mL) was added. The resulting mixture was extracted with ether (4×5 mL), and the combined organic portions dried over Na$_2$SO$_4$. Concentration followed by flash column chromatography (hexanes-acetone, 8:1) afforded 7-methylplatensimycin TMSE ester (5d) (15 mg, 47%).

R$_f$ 0.33 (hexanes-acetone, 3:1). $^1$H NMR (500 MHz, CDCl$_3$): δ 11.80 (s, 1H), 11.04 (s, 1H), 8.11 (s, 1H), 7.55 (d, J=8.9 Hz, 1H), 6.50 (d, J=8.9 Hz, 1H), 5.87 (d, J=1.2 Hz, 1H), 4.46 4.39 (m, 3H), 2.50 (ddd, J=5.5, 12.2, J=15.2 Hz, 1H), 2.43 (t, J=6.2 Hz, 1H), 2.40 2.30 (m, 3H), 2.14 2.08 (m, 1H), 2.06 (d, J=11.4 Hz, 1H), 2.01 (dd, J=3.3, 11.9 Hz, 1H), 1.99 1.87 (m, 3H), 1.86 (d, J=1.2 Hz, 3H), 1.77 (dd, J=3.2, 11.2 Hz, 1H), 1.47 (s, 3H), 1.26 (s, 3H), 1.16 1.10 (m, 2H), 0.08 (s, 9H). $^{13}$C NMR (125 MHz, CDCl$_3$): δ 202.3, 173.7, 170.5, 162.6, 154.7, 153.9, 127.3, 126.6, 114.4, 111.1, 104.4, 86.5, 76.5, 63.7, 52.3, 48.5, 46.6, 46.3, 44.7, 42.0, 40.8, 32.2, 31.7, 24.4, 23.2, 17.5, 17.4, −1.5.

Preparation of 7-methylplatensimycin (5)

Tris(dimethylamino)sulfonium difluorotrimethylsilicate (12 mg, 0.044 mmol) was added to a stirred solution of 7-methylplatensimycin TMSE ester (5d) (12.5 mg, 0.022 mmol) in DMF (0.3 mL), and the mixture was heated at 40° C. for 50 min. The solution was then cooled to r.t. and brine (0.3 mL) added. The mixture was extracted with CHCl$_3$ (5×5 mL) and the combined organic portions dried over Na$_2$SO$_4$. Concentration followed by flash column chromatography (EtOAc:hexanes:MeOH:H$_2$O:AcOH, 60:40:0.6:0.3:0.3) afforded synthetic 7-methylplatensimycin (5) (8.9 mg, 93% yield).

R$_f$ 0.31 (EtOAc:hexanes:MeOH:H$_2$O:AcOH, 80:20:1:0.5: 0.5). $^1$H NMR (500 MHz, CDCl$_3$): δ 11.83 (s, 1H), 11.16 (s, 1H), 8.14 (s, 1H), 7.60 (d, J=8.9 Hz, 1H), 6.49 (d, J=8.9 Hz, 1H), 5.91 (d, J=1.1 Hz, 1H), 4.62 (s, 1H), 2.66 2.57 (m, 1H), 2.53 2.42 (m, 4H), 2.14 (dt, J=7.1, 23.9 Hz, 2H), 2.05 (dd, J=3.1, 12.0 Hz, 1H), 2.02 1.96 (m, 1H), 1.94 (d, J=11.4 Hz, 1H), 1.88 (d, J=1.1 Hz, 3H), 1.87 1.82 (m, 2H), 1.52 (s, 3H), 1.29 (s, 3H). $^{13}$C NMR (125 MHz, CDCl$_3$): δ 202.9, 173.5, 172.2, 163.5, 155.1, 154.2, 128.1, 126.6, 114.3, 111.0, 103.8, 87.4, 76.7, 52.2, 48.5, 46.2, 46.1, 44.8, 41.9, 40.6, 31.5, 31.5, 24.6, 22.9, 17.6.

Example 13

Preparation of 7-phenylplatensimycin (6)

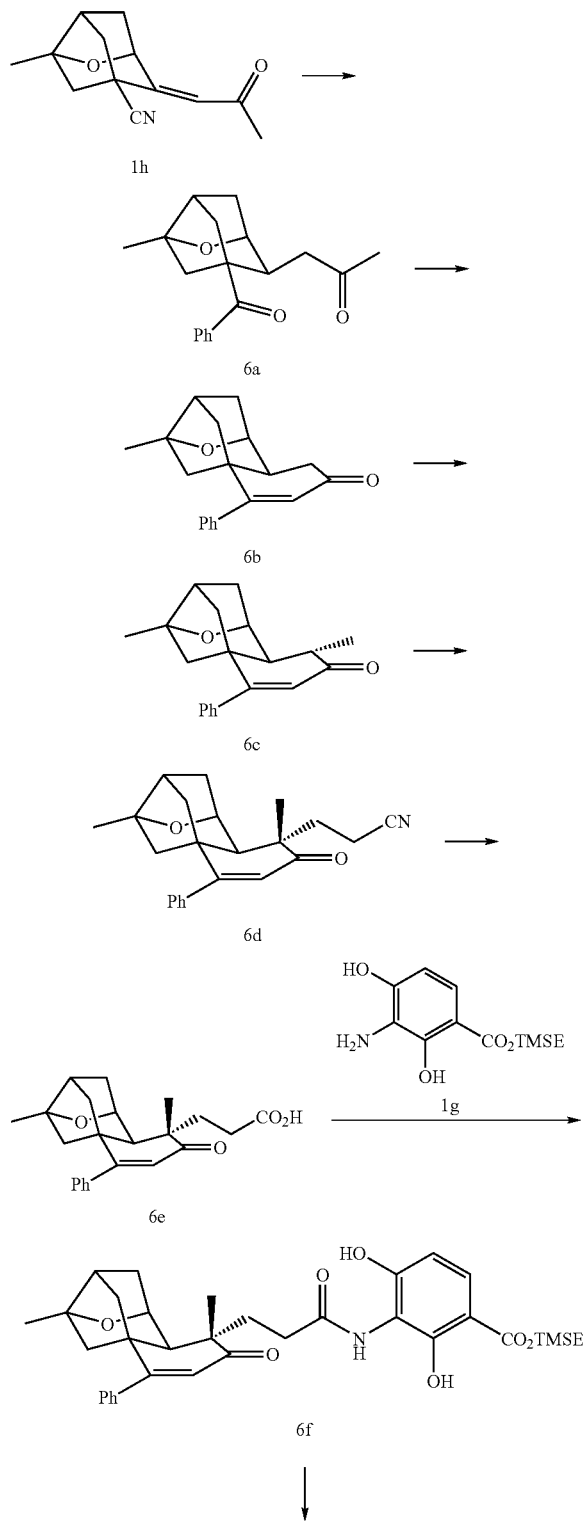

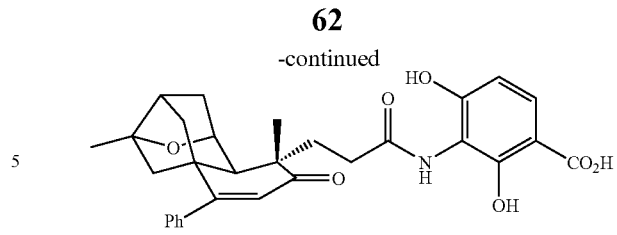

Preparation of Ketone (6a)

Dimethylphenylsilane (0.27 mL, 1.8 mmol) was added to a solution of enone (1h) (192 mg, 0.88 mmol) and $(Ph_3P)_3RhCl$ (16 mg, 0.018 mmol) in benzene (3.5 mL) at r.t. The reaction mixture was stirred for 1 h at 60° C. and cooled to −40° C. After slow addition of phenyl lithium (1.8M in diethylether, 2.5 mL, 4.5 mmol), the reaction mixture was stirred for 1 h and carefully quenched by addition of AcOH—$H_2O$ (1:1) solution (5 mL). The mixture was stirred vigorously at 0° C. for 1 h and diluted with EtOAc (30 mL). The mixture was washed with brine (5 mL×2), dried over $Na_2SO_4$, filtered and concentrated. This crude mixture was dissolved in THF (5 mL) before dropwise addition of 2 N HCl (0.2 mL) at 0° C. The mixture was stirred at 0° C. for 1 h and diluted with EtOAc (30 mL), washed with brine (5 mL), dried over $Na_2SO_4$, filtered and concentrated. The residue was purified by flash column chromatography (hexanes-acetone, 6:1) to give ketone (6a) (150 mg, 57%).

$R_f$ 0.42 (hexanes-acetone, 3:1). $^1$H NMR (500 MHz, $CDCl_3$): δ 7.89 7.81 (m, 2H), 7.55 7.47 (m, 1H), 7.46 7.39 (m, 2H), 4.30 (t, J=3.8 Hz, 1H), 3.23 3.18 (m, 1H), 2.54 (dd, J=2.9, 11.4 Hz, 1H), 2.40 (dd, J=4.8, 17.4 Hz, 1H), 2.29 2.21 (m, 2H), 2.01 1.92 (m, 2H), 1.94 (s, 3H), 1.91 1.85 (m, 1H), 1.82 (d, J=11.5 Hz, 1H), 1.75 (d, J=11.4 Hz, 1H), 1.42 (s, 3H). $^{13}$C NMR (125 MHz, $CDCl_3$): δ 206.2, 204.2, 137.8, 132.4, 128.5, 128.5, 86.5, 79.4, 60.1, 50.6, 43.2, 42.7, 40.5, 38.7, 37.8, 30.2, 23.2.

Preparation of Cyclic Enone (6b)

p-TsOH monohydrate (10 mol %, 9 mg) was added to a solution of ketone (6a) (140 mg, 0.47 mmol) in toluene (9 mL) and the mixture was heated under reflux for 2 h with concomitant removal of water (Dean-Stark trap). After cooling to r.t., the mixture was diluted with $Et_2O$ (20 mL), washed with sat. $NaHCO_3$ solution (5 mL), dried over $MgSO_4$, filtered and concentrated. Flash column chromatography (hexanes-acetone, 9:1) provided cyclic enone (6b) (127 mg, 97%).

$R_f$ 0.44 (hexanes-acetone, 3:1). $^1$H NMR (500 MHz, $CDCl_3$): δ 7.38 7.34 (m, 3H), 7.12 7.07 (m, 2H), 5.89 (s, 1H), 4.19 (t, J=3.3 Hz, 1H), 2.62 2.52 (m, 1H), 2.49 2.40 (m, 2H), 2.24 (t, J=6.2 Hz, 1H), 2.01 1.80 (m, 5H), 1.48 (d, J=11.2 Hz, 1H), 1.35 (s, 3H). $^{13}$C NMR (125 MHz, $CDCl_3$): δ 198.4, 166.8, 137.7, 129.0, 128.4, 128.2, 127.7, 86.6, 79.3, 49.9, 48.9, 43.9, 43.6, 41.8, 38.0, 37.7, 23.4.

Preparation of Enone (6c)

KHMDS (0.5 M solution in toluene, 0.44 mL, 0.22 mmol) was added to a solution of enone (6b) (31 mg, 0.11 mmol) in THF (2.5 mL) and HMPA (0.5 mL) at −78° C. The reaction mixture was allowed to stir at −78° C. for 30 min, after which MeI (0.05 mL, 0.80 mmol) was added. The reaction mixture was stirred at −10° C. for 1 h. The reaction mixture was quenched with sat. $NH_4Cl$ solution (3 mL) and extracted with ether (2×10 mL). The combined organic extracts were washed with brine (2×5 mL), dried over anhydrous $Na_2SO_4$, filtered and concentrated. The residue was purified by flash column chromatography (hexanes-acetone, 15:1) to give enone (6c) (29 mg, 89%).

$R_f$ 0.46 (hexanes-acetone, 3:1). $^{13}$C NMR (125 MHz, $CDCl_3$): δ 200.5, 165.6, 137.6, 128.4, 128.3, 128.2, 127.8, 86.4, 78.0, 49.9, 49.3, 44.1, 42.0, 41.3, 37.4, 23.4, 11.3.

Preparation of Enone (6d)

Enone (6c) (29 mg, 0.10 mmol) was dissolved in t-BuOH (1.0 mL) and 40% KOH solution (0.0016 mL, 0.020 mmol) was added to the solution. The reaction mixture was allowed to stir at 60° C. for 5 min, after which acrylonitrile (0.033 mL, 0.50 mmol) was slowly added over 2 h at 60° C. The reaction mixture was stirred at 60° C. for 12 h. The reaction mixture was quenched with sat. $NH_4Cl$ solution (2 mL) and extracted with ether (2×10 mL). The combined organic extracts were washed with brine (2×5 mL), dried over anhydrous $Na_2SO_4$, filtered and concentrated. The residue was purified by flash column chromatography (hexanes-acetone, 13:1) to give enone (6d) (27 mg, 79%).

$R_f$ 0.39 (hexanes-acetone, 3:1). $^1$H NMR (500 MHz, $CDCl_3$): δ 7.39 7.34 (m, 3H), 7.11 7.05 (m, 2H), 5.82 (s, 1H), 4.39 (s, 1H), 2.45 2.30 (m, 5H), 2.14 2.04 (m, 3H), 1.87 1.79 (m, 3H), 1.46 (d, J=11.3 Hz, 1H), 1.36 (s, 3H), 1.35 (s, 3H). $^{13}$C NMR (125 MHz, $CDCl_3$): δ 201.7, 165.3, 137.0, 128.3, 128.2, 127.8, 127.6, 119.8, 86.7, 76.5, 52.8, 48.5, 46.7, 46.3, 44.2, 42.0, 40.8, 31.8, 24.4, 23.2, 12.9.

Preparation of Carboxylic Acid (6e)

To a stirred solution of enone (6d) (25 mg, 0.072 mmol) in MeOH (0.7 mL) and THF (0.7 mL) was added 20% KOH solution (3.5 mL). The reaction mixture was heated under reflux for 3 h. After cooling to r.t., the reaction mixture was treated with 2 N HCl (10 mL) and extracted with EtOAc (20 mL×2). The combined organic extracts were washed with brine (2×5 mL), dried over anhydrous $Na_2SO_4$, filtered and concentrated. The residue was purified by flash column chromatography ($CHCl_3$-MeOH, 20:1) to give acid (6e) (26 mg, 99%).

$R_f$ 0.28 ($CHCl_3$-MeOH, 10:1). $^1$H NMR (500 MHz, $CDCl_3$): δ 7.40 7.32 (m, 3H), 7.13 7.03 (m, 2H), 5.82 (s, 1H), 4.46 (s, 1H), 2.51 (s, 1H), 2.47 2.38 (m, 1H), 2.37 2.28 (m, 3H), 2.13 2.06 (m, 3H), 1.87 1.76 (m, 3H), 1.46 (t, J=9.9 Hz, 1H), 1.35 (s, 3H), 1.34 (s, 3H). $^{13}$C NMR (125 MHz, $CDCl_3$): δ 202.6, 177.8, 164.8, 137.3, 128.2, 128.1, 127.9, 127.9, 86.7, 76.7, 52.8, 48.4, 46.7, 46.4, 44.3, 42.0, 40.8, 30.8, 29.2, 24.9, 23.2.

Preparation of 7-phenylplatensimycin TMSE ester (6f)

TEA (0.040 mL, 0.29 mmol) and HATU (86 mg, 0.22 mmol) were added to a solution of carboxylic acid (6e) (25 mg, 0.068 mmol) and aniline (1g) (59 mg, 0.22 mmol) in DMF (0.3 mL) at r.t. The reaction mixture was stirred at 24° C. for 15 h, after which brine (0.3 mL) was added. The resulting mixture was extracted with ether (4×5 mL), and the combined organic portions dried over $Na_2SO_4$. Concentration followed by flash column chromatography (hexanes-acetone, 8:1) afforded 7-phenylplatensimycin TMSE ester (6f) (25 mg, 59%).

$R_f$ 0.43 (hexanes-acetone, 3:1). $^1$H NMR (500 MHz, $CDCl_3$): δ 11.82 (s, 1H), 11.05 (s, 1H), 8.13 (s, 1H), 7.56 (d, J=9.0 Hz, 1H), 7.36 (dd, J=3.7, 6.7 Hz, 3H), 7.13 7.06 (m, 2H), 6.51 (d, J=9.0 Hz, 1H), 5.85 (s, 1H), 4.49 (s, 1H), 4.46 4.39 (m, 2H), 2.64 2.37 (m, 4H), 2.35 2.27 (m, 1H), 2.23 2.05 (m, 3H), 1.96 (ddd, J=5.4, 11.7, 13.9 Hz, 1H), 1.84 (dd, J=3.7, 11.3 Hz, 2H), 1.47 (d, J=11.3 Hz, 1H), 1.39 (s, 3H), 1.35 (s, 3H), 1.14 1.11 (m, 2H), 0.09 (s, 9H). $^{13}$C NMR (125 MHz, $CDCl_3$): δ 202.7, 173.6, 170.5, 165.0, 154.7, 153.9, 137.0, 128.0, 127.9, 127.6, 127.6, 127.4, 114.4, 111.1, 104.5, 86.4, 76.4, 63.7, 52.6, 48.3, 46.7, 46.5, 44.1, 41.8, 40.6, 32.1, 31.7, 24.5, 23.1, 17.4, −1.5.

Preparation of 7-phenylplatensimycin (6)

Tris(dimethylamino)sulfonium difluorotrimethylsilicate (18 mg, 0.064 mmol) was added to a stirred solution of 7-phenylplatensimycin TMSE ester (6f) (20 mg, 0.032 mmol) in DMF (0.6 mL), and the mixture was heated at 40° C. for 50 min. The solution was then cooled to r.t. and brine (0.6 mL) added. The mixture was extracted with $CHCl_3$ (5×5 mL) and the combined organic portions dried over $Na_2SO_4$. Concentration followed by flash column chromatography (EtOAc:hexanes:MeOH:$H_2O$:AcOH, 60:40:0.6:0.3:0.3) afforded synthetic 7-phenylplatensimycin (6) (16 mg, 95% yield).

$R_f$ 0.40 (EtOAc:hexanes:MeOH:$H_2O$:AcOH, 80:20:1:0.5:0.5). $^1$H NMR (500 MHz, THF): δ 9.04 (s, 1H), 7.55 (d, J=8.8 Hz, 1H), 7.36 7.29 (m, 3H), 7.12 (d, J=7.9 Hz, 2H), 6.39 (d, J=8.8 Hz, 1H), 5.71 (s, 1H), 4.46 (s, 1H), 2.64 2.41 (m, 3H), 2.39 2.29 (m, 1H), 2.24 (t, J=6.5 Hz, 1H), 2.17 2.08 (m, 2H), 2.03 1.95 (m, 1H), 1.94 1.85 (m, 1H), 1.84 1.73 (m, 2H), 1.45 (d, J=11.0 Hz, 1H), 1.34 (s, 3H), 1.26 (s, 3H). $^{13}$C NMR (125 MHz, THF): δ 203.0, 176.2, 174.5, 166.1, 158.2, 157.8, 139.7, 129.7, 129.7, 129.6, 129.4, 116.8, 112.3, 87.7, 78.3, 54.8, 50.3, 48.9, 48.2, 46.4, 43.7, 42.4, 33.5, 32.8, 31.7, 26.0, 24.5.

Example 14

Preparation of 15-phenylplatensimycin (7)

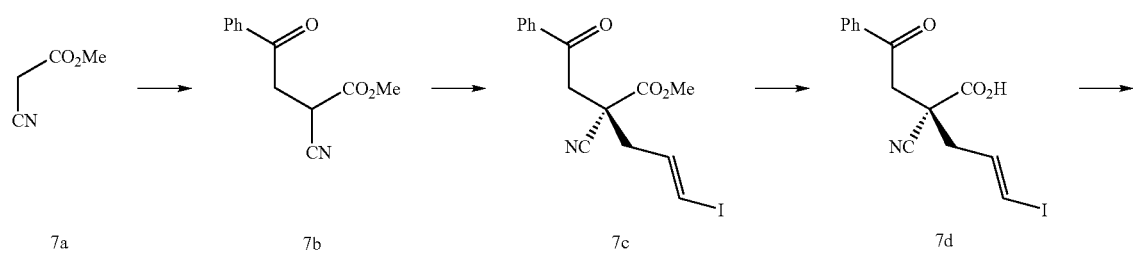

7a      7b      7c      7d

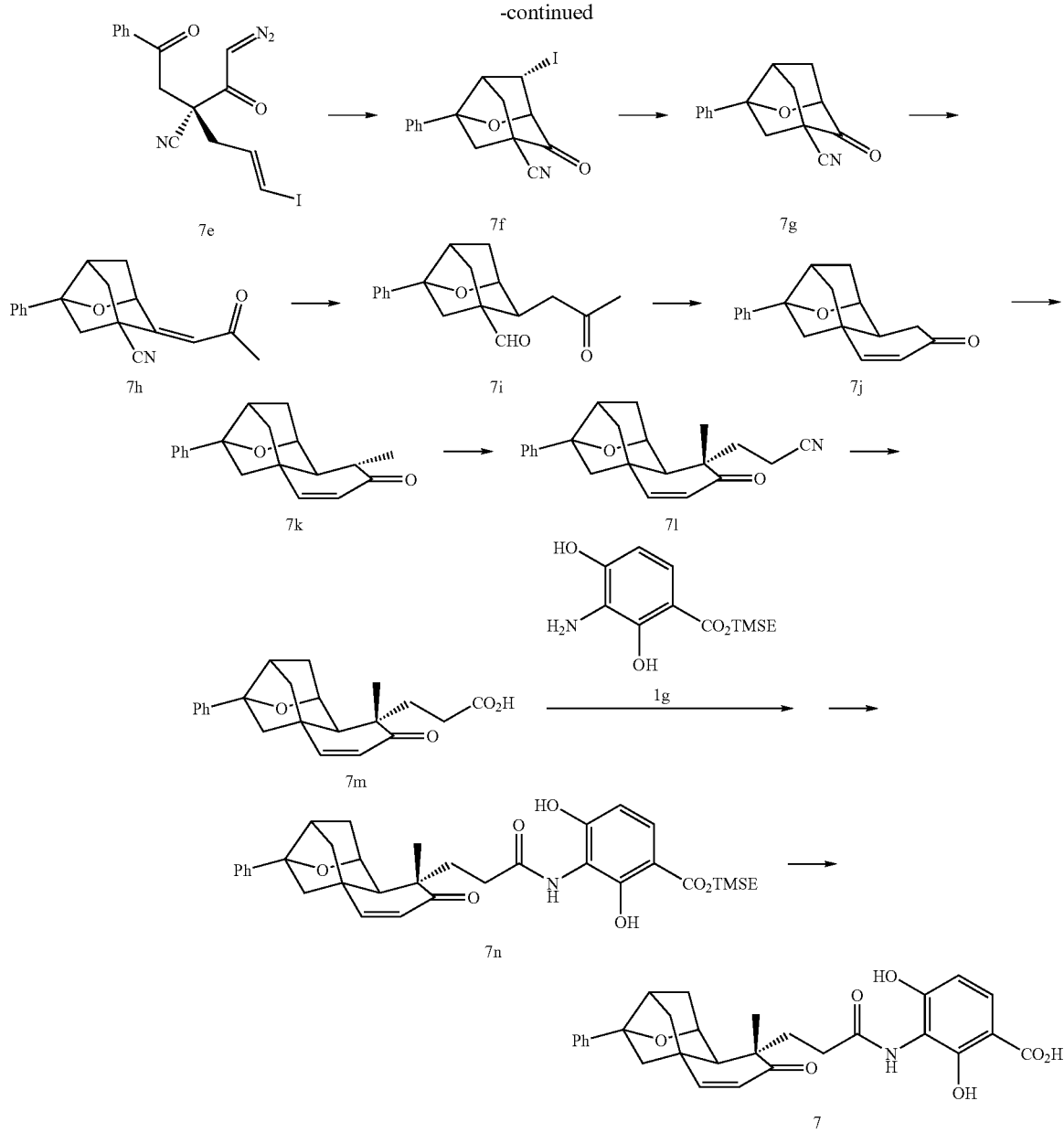

Preparation of Ester (7c)

Ethyl cyanoacetate (7a) (1.0 mL, 9.4 mmol) was added to a solution of sodium methoxide prepared from absolute methanol (10 mL) and sodium (220 mg, 9.6 mmol) at 0° C. After 10 min stirring, chloroacetophenone (1.45 g, 9.4 mmol) was added and the reaction mixture was stirred at r.t. for 12 h. After dilution with Et$_2$O (30 mL), the reaction mixture was cooled to 0° C. and treated with sat. NH$_4$Cl solution (30 mL). The aqueous phase was extracted with EtOAc (40 mL×2) and the combined organic extracts were washed with 1 N HCl solution (saturated with NaCl, 20 mL×2), dried over MgSO$_4$, filtered and concentrated. The residue was purified by flash column chromatography (hexanes-EtOAc, 2:1) to give ester (7b) (1.7 g, 83%).

R$_f$ 0.41 (hexanes-EtOAc, 2:1). $^1$H NMR (500 MHz, CDCl$_3$): δ 7.99 7.92 (m, 2H), 7.66 7.60 (m, 1H), 7.53 7.46 (m, 2H), 4.16 (dd, J=5.5, 6.6 Hz, 1H), 3.85 (s, 3H), 3.77 and 3.60 (ABX, J$_{AB}$=21.7, J$_{AX}$=6.7, J$_{BX}$=5.5 Hz, 2H). $^{13}$C NMR (125 MHz, CDCl$_3$): δ 194.4, 166.2, 135.4, 134.4, 129.1, 129.1, 128.4, 116.5, 54.1, 38.3, 32.0.

Ester (7b) (780 mg, 3.6 mmol) was added to a solution of sodium hydride (60% dispersion in mineral oil, 160 mg, 4.0 mmol) in THF (18 mL) at 0° C. The mixture was stirred for 10 min before addition of (E)-iodoallyl iodide (1.4 g, 4.7 mmol) and warmed to r.t. After 2 h, the reaction was quenched by addition of sat. NH$_4$Cl solution (20 mL), and the reaction mixture was extracted with Et$_2$O (100 mL×2). The organic phase was washed with brine (50 mL), dried over MgSO$_4$, filtered and concentrated. Purification of the residue by flash column chromatography (hexanes-EtOAc, 3:1) gave methyl ester (7c) (910 mg, 66%.).

R$_f$ 0.45 (hexanes-EtOAc, 2:1). $^1$H NMR (500 MHz, CDCl$_3$): δ 7.91 (t, J=6.8 Hz, 2H), 7.60 (t, J=7.4 Hz, 1H), 7.47

(t, J=7.8 Hz, 2H), 6.67 6.57 (m, 1H), 6.43 (d, J=14.4 Hz, 1H), 3.84 (s, 3H), 3.71 and 3.59 (ABq, J=18.0 Hz, 2H), 2.75-2.66 (m, 2H).

Preparation of Diazoketone (7e)

Ester (7c) (910 g, 2.4 mmol) was dissolved in MeOH (15 mL) and 1 N KOH solution (4.7 mL) was added to the solution at 0° C. The reaction mixture was stirred for 10 min at r.t. and treated slowly with 2 N HCl (2.4 mL) at 0° C. After extraction with EtOAc (100 mL×2), the organic phase was dried over $MgSO_4$, filtered and concentrated. The residue was dissolved in toluene (10 mL) and evaporated to provide the crude acid (7d) (880 mg, quant.) which was used in the next step without further purification.

TEA (0.40 mL, 2.9 mmol) was added to the solution of the crude acid (7d) (880 mg, 2.4 mmol) in THF (10 mL) at −20° C. and the mixture was treated with isobutyl chloroformate (0.34 mL, 2.6 mmol). After 30 min, an ethereal solution of diazomethane, which was prepared by the reaction of Diazald (3.0 g, 14 mmol) with KOH (3.0 g, 54 mmol), was slowly added to the reaction mixture. After stirring the reaction mixture for 3 h, excess diazomethane was decomposed by careful addition of acetic acid at 0° C. The reaction mixture was filtered through a short column of silica gel with the aid of $Et_2O$ and concentrated. The residue was purified by flash column chromatography (hexanes-EtOAc, 4:1) to provide diazoketone (7e) (800 mg, 86%, two steps).

$R_f$ 0.47 (hexanes-EtOAc, 2:1). $^1H$ NMR (500 MHz, $CDCl_3$): δ 7.91 (d, J=7.2 Hz, 2H), 7.61 (t, J=7.4 Hz, 1H), 7.52 7.45 (m, 2H), 6.65 6.57 (m, 1H), 6.46 (d, J=14.5 Hz, 1H), 6.18 (s, 1H)), 3.84 and 3.44 (ABq, J=16.8 Hz, 2H), 2.69 and 2.57 (ABX, $J_{AB}$=16.8, $J_{AX}$=7.5, $J_{BX}$=7.9 Hz, 2H).

Preparation of Enone (7h)

$Rh_2(OAc)_4$ (27 mg, 0.061 mmol) was added to a solution of diazoketone (7e) (800 mg, 2.0 mmol) in $CH_2Cl_2$ (200 mL). After stirring for 10 h, the reaction mixture was filtered through a short column of silica gel with the aid of hexanes-EtOAc (1:1) to remove the catalyst, and the filtrate was concentrated in vacuo. The residue was purified by flash column chromatography (hexanes-acetone-$CH_2Cl_2$, 4:1:1) to provide ketone (7f) (480 mg, 65%). $R_f$ 0.29 (hexanes-acetone-$CH_2Cl_2$, 4:1:1).

To a solution of hypophosphorous acid (50% aq. solution, 0.90 g, 6.8 mmol) in MeOH (27 mL), 1-ethylpiperidine (0.94 mL, 6.8 mmol) was slowly added at 0° C. After 10 min, a solution of ketone (7f) (500 mg, 1.4 mmol) in MeOH (3 mL) was added to the solution, followed by the addition of $Et_3B$ (1M in hexanes, 2.8 mL, 2.8 mmol). The reaction mixture was stirred 20 min before dilution with EtOAc (150 mL). The organic phase was washed with brine (30 mL×2), dried over $MgSO_4$, filtered and concentrated. Flash column chromatography (hexanes-EtOAc, 1:1) provided ketone (7 g) (300 mg, 92%) as a mixture of keto and hydrate forms. $R_f$ 0.30 (hexanes-EtOAc, 1:1).

Dimethyl 2-oxopropylphosphonate (1.2 mL, 1.4 mmol) was added to a stirred suspension of anhydrous LiCl (106 mg, 2.5 mmol) and DIPEA (0.33 mL, 1.9 mmol) in anhydrous MeCN (13 mL) at 0° C. After 15 min, a solution of ketone (7g) (300 mg, 1.3 mmol) in anhydrous MeCN (2 mL) was added to the mixture and the reaction mixture was stirred for 2 h at r.t. before dilution with $Et_2O$ (100 mL). The organic phase was washed with brine (20 mL×2), dried over $MgSO_4$, filtered and concentrated. The residue was purified by flash column chromatography (hexanes-EtOAc, 3:1) to give enone (7h) (270 mg, 77%).

$R_f$ 0.47 (hexanes-EtOAc, 4:1). $^1H$ NMR (500 MHz, $CDCl_3$): δ 7.41 7.25 (m, 5H), 6.50 (s, 1H), 6.04 (d, J=4.9 Hz, 1H), 2.88 (t, J=6.4 Hz, 1H), 2.62 (s, 2H), 2.57 (ddd, J=2.7, 6.7, 11.6 Hz, 1H), 2.29 (s, 3H), 2.28 2.23 (m, 1H), 2.14 (d, J=11.6 Hz, 1H), 1.89 (d, J=11.7 Hz, 1H). $^{13}C$ NMR (125 MHz, $CDCl_3$): δ 198.3, 149.4, 141.0, 128.7, 127.9, 125.2, 121.8, 118.6, 89.1, 75.3, 54.1, 48.8, 47.6, 46.3, 42.9, 32.0.

Preparation of Aldehyde (7i)

Dimethylphenylsilane (0.22 mL, 1.4 mmol) was added to a solution of enone (7h) (200 mg, 0.72 mmol) and $(Ph_3P)_3RhCl$ (33 mg, 0.036 mmol) in toluene (1 mL) at r.t. The reaction mixture was stirred for 1 h at 60° C. and cooled to −40° C. After slow addition of DIBAL (1M in toluene, 2.9 mL, 2.9 mmol), the reaction mixture was stirred for 1 h and carefully quenched by addition of AcOH—$H_2O$ (1:1) solution (3 mL). The mixture was stirred vigorously at 0° C. for 1 h and diluted with EtOAc (30 mL). The mixture was washed with brine (5 mL×2), dried over $Na_2SO_4$, filtered and concentrated. This crude mixture was dissolved in THF (3 mL) before dropwise addition of 2 N HCl (0.1 mL) at 0° C. The mixture was stirred at 0° C. for 1 h and diluted with EtOAc (30 mL), washed with brine (5 mL), dried over $Na_2SO_4$, filtered and concentrated. The residue was purified by flash column chromatography (hexanes-acetone, 13:1) to give aldehyde (7i) (128 mg, 63%).

$R_f$ 0.48 (hexanes-acetone, 3:1). $^1H$ NMR (500 MHz, $CDCl_3$): δ 9.42 (s, 1H), 7.43 7.24 (m, 5H), 4.48 (t, J=3.9 Hz, 1H), 2.96 (s, 1H), 2.76 2.64 (m, 2H), 2.29 2.14 (m, 6H), 2.12 2.06 (m, 1H), 2.04 1.94 (m, 1H), 1.88 (d, J=11.7 Hz, 1H), 1.84 (dd, J=3.4, 12.2 Hz, 1H). $^{13}C$ NMR (125 MHz, $CDCl_3$): δ 206.4, 202.5, 142.6, 128.5, 127.4, 125.2, 88.9, 79.1, 59.2, 48.8, 47.5, 42.6, 38.4, 38.1, 36.2, 30.4.

Preparation of Cyclic Enone (7j)

p-TsOH monohydrate (10 mol %, 9 mg) was added to a solution of aldehyde (7i) (128 mg, 0.45 mmol) in toluene (9 mL) and the mixture was heated under reflux for 2 h with concomitant removal of water (Dean-Stark trap). After cooling to r.t., the mixture was diluted with $Et_2O$ (20 mL), washed with sat. $NaHCO_3$ solution (3 mL), dried over $MgSO_4$, filtered and concentrated. Flash column chromatography (hexanes-acetone, 6.5:1) provided cyclic enone (7j) (115 mg, 96%).

$R_f$ 0.52 (hexanes-acetone, 3:1). $^1H$ NMR (500 MHz, $CDCl_3$): δ 7.46 7.41 (m, 2H), 7.40 7.34 (m, 2H), 7.30 7.25 (m, 1H), 6.70 (d, J=10.0 Hz, 1H), 5.99 (dd, J=0.6, 10.0 Hz, 1H), 4.38 (t, J=3.7 Hz, 1H), 2.70 (t, J=6.3 Hz, 1H), 2.54 (dt, J=3.9, 14.4 Hz, 1H), 2.47 2.33 (m, 2H), 2.22 2.13 (m, 2H), 2.10 2.02 (m, 1H), 1.99 (d, J=11.7 Hz, 1H), 1.97 1.88 (m, 2H). $^{13}C$ NMR (125 MHz, $CDCl_3$): δ 199.0, 154.9, 143.2, 129.4, 128.5, 127.4, 125.2, 90.3, 79.4, 52.6, 47.3, 46.6, 43.1, 42.7, 38.1, 37.6.

Preparation of Enone (7k)

KHMDS (0.5 M solution in toluene, 1.7 mL, 0.85 mmol) was added to a solution of enone (7j) (115 mg, 0.43 mmol) in THF (7.5 mL) and HMPA (1.5 mL) at −78° C. The reaction mixture was allowed to stir at −78° C. for 30 min, after which MeI (0.22 mL, 3.4 mmol) was added. The reaction mixture was stirred at −10° C. for 1 h. The reaction mixture was quenched with sat. $NH_4Cl$ solution (3 mL) and extracted with ether (2×15 mL). The combined organic extracts were washed with brine (2×5 mL), dried over anhydrous Na$_2$SO$_4$, filtered and concentrated. The residue was purified by flash column chromatography (hexanes-acetone, 20:1) to give enone (7k) (73 mg, 60%).

R$_f$ 0.57 (hexanes-acetone, 3:1). $^1$H NMR (500 MHz, CDCl$_3$): δ 7.45 7.41 (m, 2H), 7.39 7.34 (m, 2H), 7.30 7.26 (m, 1H), 6.63 (d, J=10.0 Hz, 1H), 5.98 (d, J=9.9 Hz, 1H), 4.59 (t, J=3.8 Hz, 1H), 2.75 2.70 (m, 1H), 2.44 (dq, J=6.7, 13.4 Hz, 1H), 2.22 (dd, J=3.1, 13.6 Hz, 1H), 2.16 (dd, J=1.8, 11.6 Hz, 1H), 2.12 (d, J=11.4 Hz, 1H), 2.10 2.02 (m, 1H), 2.00 1.91 (m, 3H), 1.19 (d, J=6.7 Hz, 3H). $^{13}$C NMR (125 MHz, CDCl$_3$): δ 201.2, 153.8, 143.3, 128.7, 128.5, 127.3, 125.2, 90.2, 78.1, 52.8, 49.0, 47.5, 47.2, 43.0, 41.5, 37.3, 11.2.

Preparation of Enone (7l)

To a stirred solution of enone (7k) (93 mg, 0.33 mmol) in t-BuOH (3.3 mL) and THF (0.8 mL) was added 40% KOH solution (0.0053 mL, 0.066 mmol) was added to the solution. The reaction mixture was allowed to stir at 60° C. for 5 min, after which acrylonitrile (0.15 mL, 2.3 mmol) was slowly added over 2 h at 60° C. The reaction mixture was stirred at 60° C. for 12 h. The reaction mixture was quenched with sat. NH$_4$Cl solution (2 mL) and extracted with ether (2×15 mL). The combined organic extracts were washed with brine (2×5 mL), dried over anhydrous Na$_2$SO$_4$, filtered and concentrated. The residue was purified by flash column chromatography (hexanes-acetone, 10:1) to give enone (7l) (42 mg, 38%).

R$_f$ 0.32 (hexanes-acetone, 3:1). $^1$H NMR (500 MHz, CDCl$_3$): δ 7.42 (dd, J=1.1, 8.2 Hz, 2H), 7.37 (t, J=7.6 Hz, 2H), 7.29 (t, J=7.2 Hz, 1H), 6.59 (d, J=10.1 Hz, 1H), 5.95 (d, J=10.1 Hz, 1H), 4.58 (s, 1H), 2.81 (t, J=6.6 Hz, 1H), 2.47 2.29 (m, 4H), 2.26 2.08 (m, 5H), 2.00 (dd, J=6.9, 12.0 Hz, 1H), 1.88 1.80 (m, 1H), 1.30 (s, 3H). $^{13}$C NMR (125 MHz, CDCl$_3$): δ 202.4, 153.6, 142.8, 128.5, 127.5, 127.5, 125.2, 119.7, 90.4, 76.7, 55.7, 47.6, 46.5, 46.5, 46.4, 43.6, 40.7, 31.9, 24.1, 12.9.

Preparation of Carboxylic Acid (7m)

To a stirred solution of enone (7l) (20 mg, 0.060 mmol) in MeOH (0.6 mL) and THF (0.6 mL) was added 20% KOH solution (3 mL). The reaction mixture was heated under reflux for 6 h. After cooling to r.t., the reaction mixture was treated with 2 N HCl (9 mL) and extracted with EtOAc (20 mL×2). The combined organic extracts were washed with brine (2×5 mL), dried over anhydrous Na$_2$SO$_4$, filtered and concentrated. The residue was purified by flash column chromatography (CHCl$_3$-MeOH, 20:1) to give acid (7m) (15 mg, 71%).

R$_f$ 0.31 (CHCl$_3$-MeOH, 10:1). $^1$H NMR (500 MHz, CDCl$_3$): δ 7.42 (d, J=8.1 Hz, 2H), 7.37 (t, J=7.6 Hz, 2H), 7.30 7.26 (m, 1H), 6.56 (d, J=10.1 Hz, 1H), 5.95 (d, J=10.0 Hz, 1H), 4.63 (s, 1H), 2.79 (t, J=6.5 Hz, 1H), 2.49 (s, 1H), 2.48 2.40 (m, 1H), 2.37 2.27 (m, 2H), 2.24 2.15 (m, 2H), 2.15 2.07 (m, 3H), 1.98 (dd, J=6.8, 11.9 Hz, 1H), 1.85 1.76 (m, 1H), 1.29 (s, 3H). $^{13}$C NMR (125 MHz, CDCl$_3$): δ 203.3, 178.1, 153.3, 143.1, 128.5, 127.8, 127.4, 125.2, 90.4, 76.9, 55.7, 47.7, 46.6, 46.5, 46.4, 43.6, 40.7, 30.8, 29.2, 24.7.

Preparation of 15-phenylplatensimycin TMSE ester (7n)

TEA (0.065 mL, 0.47 mmol) and HATU (142 mg, 0.37 mmol) were added to a solution of carboxylic acid (7m) (33 mg, 0.094 mmol) and aniline (1g) (100 mg, 0.37 mmol) in DMF (0.5 mL) at r.t. The reaction mixture was stirred at 24° C. for 22 h, after which brine (0.5 mL) was added. The resulting mixture was extracted with ether (4×7 mL), and the combined organic portions dried over Na$_2$SO$_4$. Concentration followed by flash column chromatography (hexanes-iPrOH, 30:1) afforded 15-phenylplatensimycin TMSE ester (7n) (25 mg, 44%).

R$_f$ 0.47 (hexanes-acetone, 3:1). $^1$H NMR (500 MHz, CDCl$_3$): δ 11.82 (s, 1H), 11.05 (s, 1H), 8.09 (s, 1H), 7.56 (d, J=9.0 Hz, 1H), 7.45 7.34 (m, 4H), 7.30 7.26 (m, 1H), 6.60 (d, J=10.1 Hz, 1H), 6.50 (t, J=7.5 Hz, 1H), 5.98 (d, J=10.1 Hz, 1H), 4.68 (s, 1H), 4.45 4.39 (m, 2H), 2.81 (t, J=6.5 Hz, 1H), 2.59 (ddd, J=5.4, 12.1, 15.0 Hz, 1H), 2.52 (s, 1H), 2.47 2.37 (m, 2H), 2.26 2.19 (m, 2H), 2.16 2.09 (m, 3H), 2.05 1.93 (m, 2H), 1.33 (s, 3H), 1.17 1.10 (m, 2H), 0.09 (s, 9H). $^{13}$C NMR (125 MHz, CDCl$_3$): δ 203.4, 173.5, 170.5, 154.7, 153.9, 153.4, 142.8, 128.3, 127.5, 127.4, 127.2, 125.0, 114.3, 111.1, 104.5, 90.1, 76.6, 63.7, 55.6, 47.5, 46.7, 46.4, 46.3, 43.4, 40.5, 32.2, 31.7, 24.3, 17.4, −1.5.

Preparation of 15-phenylplatensimycin (7)

Tris(dimethylamino)sulfonium difluorotrimethylsilicate (21 mg, 0.076 mmol) was added to a stirred solution of 15-phenylplatensimycin TMSE ester (7n) (23 mg, 0.038 mmol) in DMF (0.4 mL), and the mixture was heated at 40° C. for 50 min. The solution was then cooled to r.t. and brine (0.4 mL) added. The mixture was extracted with CHCl$_3$ (5×5 mL) and the combined organic portions dried over Na$_2$SO$_4$. Concentration followed by flash column chromatography (hexanes:acetone:AcOH, 70:30:0.5) afforded synthetic 15-phenylplatensimycin (7) (19 mg, 97% yield).

R$_f$ 0.54 (hexanes:acetone:AcOH, 40:60:1). $^1$H NMR (500 MHz, acetone): δ 11.96 (s, 1H), 10.77 (s, 1H), 9.14 (s, 1H), 7.67 (d, J=8.9 Hz, 1H), 7.51 7.46 (m, 2H), 7.39 7.33 (m, 2H), 7.29 7.23 (m, 1H), 6.75 (d, J=10.1 Hz, 1H), 6.51 (d, J=8.9 Hz, 1H), 5.90 (d, J=10.1 Hz, 1H), 4.72 (s, 1H), 2.80 2.72 (m, 2H), 2.56 (s, 1H), 2.52 2.43 (m, 1H), 2.38 (ddd, J=4.6, 11.6, 14.1 Hz, 1H), 2.27 (d, J=11.2 Hz, 1H), 2.25 2.19 (m, 2H), 2.18 2.10 (m, 2H), 2.01 (dd, J=3.8, 11.2 Hz, 1H), 1.98 1.93 (m, 1H), 1.32 (s, 3H). $^{13}$C NMR (125 MHz, acetone): δ 203.2, 175.3, 172.6, 157.0, 156.4, 154.2, 144.7, 128.9, 128.8, 127.9, 127.6, 125.8, 115.4, 111.2, 105.0, 90.7, 77.3, 56.4, 48.8, 47.3, 47.2, 47.1, 43.7, 41.1, 32.3, 32.0, 24.8.

Example 15

Preparation of Isoplatensimycin (8)

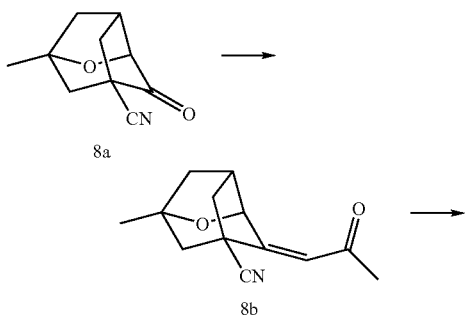

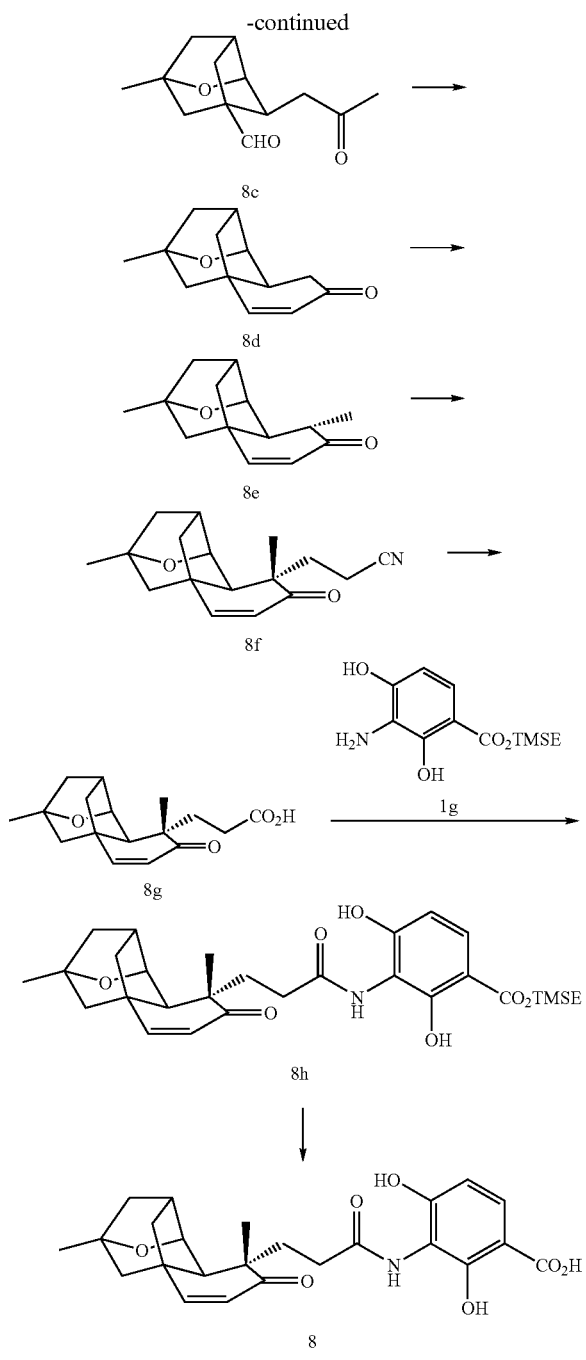

$R_f$ 0.58 (hexanes-EtOAc, 1:1). $^1$H NMR (500 MHz, CDCl$_3$): δ 6.30 (s, 1H), 5.72 (d, J=5.3 Hz, 1H), 2.93 (dd, J=6.1, 12.2 Hz, 1H), 2.30 (s, 3H), 2.18 (dt, J=2.3, 12.8 Hz, 1H), 2.11 (d, J=12.8 Hz, 1H), 2.07 (d, J=11.8 Hz, 1H), 1.98 1.92 (m, 1H), 1.88 (d, J=11.3 Hz, 1H), 1.86 1.81 (m, 1H), 1.30 (s, 3H). $^{13}$C NMR (125 MHz, CDCl$_3$): δ 197.8, 156.5, 118.9, 116.0, 80.4, 75.8, 47.6, 46.2, 43.3, 41.7, 39.2, 31.8, 22.7.

Preparation of Aldehyde (8c)

Dimethylphenylsilane (0.21 mL, 1.4 mmol) was added to a solution of enone (8b) (147 mg, 0.68 mmol) and [Rh{(R,R)-Phebox-iPr}(OAc)$_2$].H$_2$O (7.3 mg, 0.014 mmol) in toluene (1.4 mL) at r.t. The reaction mixture was stirred for 1 h at 60° C. and cooled to −40° C. After slow addition of DIBAL (1M in toluene, 2.7 mL, 2.7 mmol), the reaction mixture was stirred for 1 h and carefully quenched by addition of AcOH—H$_2$O (1:1) solution (3 mL). The mixture was stirred vigorously at 0° C. for 1 h and diluted with EtOAc (15 mL). The mixture was washed with brine (5 mL×2), dried over Na$_2$SO$_4$, filtered and concentrated. This crude mixture was dissolved in THF (2 mL) before dropwise addition of 2 N HCl (0.1 mL) at 0° C. The mixture was stirred at 0° C. for 1 h and diluted with EtOAc (15 mL), washed with brine (5 mL), dried over Na$_2$SO$_4$, filtered and concentrated. The residue was purified by flash column chromatography (hexanes-acetone, 7:1) to give aldehyde (8c) (77 mg, 51%).

$R_f$ 0.31 (hexanes-acetone, 3:1). $^1$H NMR (500 MHz, CDCl$_3$): δ 9.52 (s, 1H), 4.30 (d, J=5.0 Hz, 1H), 2.82 2.74 (m, 2H), 2.44 (dd, J=6.4, 17.8 Hz, 1H), 2.21 2.10 (m, 5H), 1.96 (dt, J=2.6, 12.9 Hz, 1H), 1.78 1.73 (m, 1H), 1.69 (d, J=11.0 Hz, 1H), 1.65 (d, J=12.8 Hz, 1H), 1.50 (dd, J=1.8, 12.5 Hz, 1H), 1.32 (s, 3H). $^{13}$C NMR (125 MHz, CDCl$_3$): δ 206.5, 203.0, 84.8, 80.4, 57.7, 48.3, 47.2, 41.2, 40.9, 39.5, 37.2, 30.4, 23.7.

Preparation of Cyclic Enone (8d)

p-TsOH monohydrate (10 mol %, 7 mg) was added to a solution of aldehyde (8c) (82 mg, 0.37 mmol) in toluene (7 mL) and the mixture was heated under reflux for 2 h with concomitant removal of water (Dean-Stark trap). After cooling to r.t., the mixture was diluted with Et$_2$O (20 mL), washed with sat. NaHCO$_3$ solution (5 mL), dried over MgSO$_4$, filtered and concentrated. Flash column chromatography (hexanes-acetone, 7:1) provided cyclic enone (8d) (70 mg, 93%).

$R_f$ 0.35 (hexanes-acetone, 3:1). $^1$H NMR (500 MHz, CDCl$_3$): δ 6.70 (d, J=10.0 Hz, 1H), 5.85 (d, J=10.1 Hz, 1H), 4.34 (d, J=4.9 Hz, 1H), 2.93 (dt, J=4.1, 7.2 Hz, 1H), 2.62 2.55 (m, 1H), 2.47 (dd, J=6.1, 17.5 Hz, 1H), 2.24 (dd, J=6.2, 20.5 Hz, 1H), 2.11 2.05 (m, 1H), 1.80 1.74 (m, 3H), 1.70 (dd, J=1.6, 12.3 Hz, 1H), 1.66 1.62 (m, 1H), 1.30 (s, 3H). $^{13}$C NMR (125 MHz, CDCl$_3$): δ 198.2, 154.2, 128.8, 83.9, 80.8, 54.0, 48.4, 45.5, 44.5, 43.4, 42.6, 36.4, 30.6, 23.8.

Preparation of Enone (8e)

KHMDS (0.5 M solution in toluene, 0.44 mL, 0.22 mmol) was added to a solution of enone (8d) (22 mg, 0.11 mmol) in THF (2.5 mL) and HMPA (0.5 mL) at −78° C. The reaction mixture was allowed to stir at −78° C. for 30 min, after which MeI (0.055 mL, 8.6 mmol) was added. The reaction mixture was stirred at −10° C. for 1 h. The reaction mixture was quenched with sat. NH$_4$Cl solution (2 mL) and extracted with ether (2×10 mL). The combined organic extracts were washed with brine (2×3 mL), dried over anhydrous Na$_2$SO$_4$, Preparation of Enone (8b)

NaH (60% dispersion in mineral oil, 5.3 mg, 0.13 mmol) was added to a stirred suspension of anhydrous LiCl (9 mg, 0.21 mmol) and molecular sieves (4, 20 mg) and dimethyl 2-oxopropylphosphonate (0.16 mL, 0.12 mmol) in THF (1 mL) at 0° C. After 15 min, a solution of ketone (8a) (19 mg, 0.11 mmol) in THF (0.3 mL) was added to the mixture and the reaction mixture was stirred for 15 h at r.t. before dilution with Et$_2$O (20 mL). The organic phase was washed with brine (5 mL×2), dried over MgSO$_4$, filtered and concentrated. The residue was purified by flash column chromatography (hexanes-EtOAc, 3:1) to give enone (8b) (15 mg, 65%).

filtered and concentrated. The residue was purified by flash column chromatography (hexanes-acetone, 12:1) to give enone (8e) (18 mg, 77%).

$R_f$ 0.44 (hexanes-acetone, 3:1). $^1$H NMR (500 MHz, CDCl$_3$): δ 6.64 (d, J=10.0 Hz, 1H), 5.85 (d, J=10.0 Hz, 1H), 4.49 (d, J=5.0 Hz, 1H), 2.93 (ddd, J=3.5, 6.0, 11.8 Hz, 1H), 2.30 2.21 (m, 2H), 2.12 (ddd, J=3.5, 5.5, 8.2 Hz, 1H), 1.78 1.73 (m, 3H), 1.69 (dd, J=1.1, 12.3 Hz, 1H), 1.66 1.60 (m, 1H), 1.30 (s, 3H), 1.21 (d, J=6.1 Hz, 3H). $^{13}$C NMR (125 MHz, CDCl$_3$): δ 200.5, 153.0, 128.4, 82.8, 80.8, 61.5, 48.5, 45.8, 45.2, 43.7, 42.8, 39.4, 23.8, 12.7.

Preparation of Enone (8f)

Enone (8e) (40 mg, 0.18 mmol) was dissolved in t-BuOH (1.8 mL) and 40% KOH solution (0.0030 mL, 0.036 mmol) was added to the solution. The reaction mixture was allowed to stir at 60° C. for 5 min, after which acrylonitrile (0.061 mL, 0.90 mmol) was slowly added over 2 h at 60° C. The reaction mixture was stirred at 60° C. for 12 h. The reaction mixture was quenched with sat. NH$_4$Cl solution (2 mL) and extracted with ether (2×20 mL). The combined organic extracts were washed with brine (2×5 mL), dried over anhydrous Na$_2$SO$_4$, filtered and concentrated. The residue was purified by flash column chromatography (hexanes-acetone, 7:1) to give enone (8f) (44 mg, 88%).

$R_f$ 0.37 (hexanes-acetone, 3:1). $^1$H NMR (500 MHz, CDCl$_3$): δ 6.71 (d, J=10.0 Hz, 1H), 5.88 (d, J=10.0 Hz, 1H), 4.57 (d, J=4.9 Hz, 1H), 2.94 2.84 (m, 1H), 2.49 (ddd, J=5.0, 11.2, 16.4 Hz, 1H), 2.38 2.28 (m, 2H), 2.18 2.10 (m, 1H), 2.10 2.04 (m, 1H), 1.90 (ddd, J=5.0, 11.2, 13.9 Hz, 1H), 1.83 1.71 (m, 4H), 1.66 (d, J=12.7 Hz, 1H), 1.31 (s, 3H), 1.16 (s, 3H). $^{13}$C NMR (125 MHz, CDCl$_3$): δ 201.5, 153.4, 127.9, 119.7, 82.5, 81.2, 59.8, 48.7, 47.4, 46.4, 45.9, 44.7, 43.5, 36.5, 23.6, 22.9, 13.3.

Preparation of Carboxylic Acid (8g)

Enone (8f) (18 mg, 0.066 mmol) was dissolved in MeOH (0.5 mL) and 20% KOH (3 mL, 0.13 mmol) was added to the solution. The reaction mixture was heated under reflux for 2 h. After cooling to r.t., the reaction mixture was treated with 2N HCl (8 mL) and extracted with EtOAc (30 mL×2). The combined organic extracts were washed with brine (2×5 mL), dried over anhydrous Na$_2$SO$_4$, filtered and concentrated. The residue was purified by flash column chromatography (CHCl$_3$-MeOH, 20:1) to give acid (8g) (17 mg, 88%).

$R_f$ 0.44 (CHCl$_3$-MeOH, 10:1). $^1$H NMR (500 MHz, CDCl$_3$): δ 6.68 (d, J=10.0 Hz, 1H), 5.87 (d, J=10.0 Hz, 1H), 4.65 (d, J=4.9 Hz, 1H), 2.87 (td, J=4.1, 7.2 Hz, 1H), 2.50 2.39 (m, 2H), 2.29 (ddd, J=5.1, 11.7, 16.5 Hz, 1H), 2.08 1.99 (m, 2H), 1.89 (ddd, J=4.9, 11.7, 13.9 Hz, 1H), 1.79 (d, J=2.9 Hz, 2H), 1.77 1.66 (m, 3H), 1.31 (s, 3H), 1.15 (s, 3H). $^{13}$C NMR (125 MHz, CDCl$_3$): δ 202.4, 177.0, 153.0, 128.2, 82.9, 81.4, 59.2, 48.6, 47.3, 46.8, 45.7, 44.7, 43.3, 36.2, 29.4, 23.5, 23.3.

Preparation of isoplatensimycin TMSE ester (8h)

TEA (0.028 mL, 0.20 mmol) and HATU (59 mg, 0.15 mmol) were added to a solution of carboxylic acid (8g) (14 mg, 0.048 mmol) and aniline (1g) (40 mg, 0.15 mmol) in DMF (0.2 mL) at r.t. The reaction mixture was stirred at 24° C. for 15 h, after which brine (0.2 mL) was added. The resulting mixture was extracted with ether (4×10 mL), and the combined organic portions dried over Na$_2$SO$_4$. Concentration followed by flash column chromatography (hexanes-acetone, 7:1) afforded isoplatensimycin TMSE ester (8h) (10 mg, 38%).

$R_f$ 0.34 (hexanes-acetone, 3:1). $^1$H NMR (500 MHz, CDCl$_3$): δ 11.81 (s, 1H), 10.98 (s, 1H), 7.96 (s, 1H), 7.55 (d, J=8.9 Hz, 1H), 6.71 (d, J=10.0 Hz, 1H), 6.50 (d, J=9.0 Hz, 1H), 5.90 (d, J=10.0 Hz, 1H), 4.63 (d, J=4.9 Hz, 1H), 4.46 4.39 (m, 2H), 2.92 2.85 (m, 1H), 2.66 (ddd, J=5.4, 11.2, 15.0 Hz, 1H), 2.51 2.44 (m, 1H), 2.44 2.41 (m, 1H), 2.18 (ddd, J=4.9, 11.3, 13.9 Hz, 1H), 2.11 2.05 (m, 1H), 2.02 (ddd, J=5.4, 11.3, 13.8 Hz, 1H), 1.83 1.71 (m, 4H), 1.67 (d, J=12.6 Hz, 1H), 1.30 (s, 3H), 1.19 (s, 3H), 1.16 1.11 (m, 2H), 0.09 (s, 9H). $^{13}$C NMR (125 MHz, CDCl$_3$): δ 202.3, 173.3, 170.5, 154.7, 153.9, 153.0, 127.9, 127.4, 114.3, 111.2, 104.4, 82.5, 80.8, 63.8, 59.6, 48.5, 47.2, 46.3, 45.7, 44.8, 43.2, 36.5, 32.4, 23.4, 23.0, 17.4, −1.5.

Preparation of Isoplatensimycin (8)

Tris(dimethylamino)sulfonium difluorotrimethylsilicate (8.5 mg, 0.031 mmol) was added to a stirred solution of isoplatensimycin TMSE ester (8h) (8.4 mg, 0.016 mmol) in DMF (0.3 mL), and the mixture was heated at 40° C. for 50 min. The solution was then cooled to r.t. and brine (0.3 mL) added. The mixture was extracted with CHCl$_3$ (5×5 mL) and the combined organic portions dried over Na$_2$SO$_4$. Concentration followed by flash column chromatography (EtOAc: hexanes:MeOH:H$_2$O:AcOH, 60:40:0.6:0.3:0.3) afforded synthetic isoplatensimycin (8) (6.5 mg, 95% yield).

$R_f$ 0.21 (EtOAc:hexanes:MeOH:H$_2$O:AcOH, 80:20:1:0.5: 0.5). $^1$H NMR (500 MHz, CDCl$_3$): δ 11.78 (s, 1H), 11.05 (s, 1H), 8.07 (s, 1H), 7.59 (d, J=8.9 Hz, 1H), 6.77 (d, J=10.0 Hz, 1H), 6.48 (d, J=8.9 Hz, 1H), 5.96 (d, J=10.0 Hz, 1H), 4.79 (d, J=4.9 Hz, 1H), 2.95 (s, 1H), 2.77 2.65 (m, 1H), 2.62 2.52 (m, 2H), 2.22 2.05 (m, 3H), 1.85 (d, J=2.9 Hz, 2H), 1.83 1.75 (m, 3H), 1.36 (s, 3H), 1.22 (s, 3H). $^{13}$C NMR (125 MHz, CDCl$_3$): δ 203.0, 173.3, 172.3, 155.2, 154.2, 153.6, 128.2, 127.8, 114.2, 111.2, 103.6, 82.7, 81.9, 59.2, 48.3, 47.0, 46.4, 45.7, 44.7, 43.1, 36.9, 31.9, 23.1, 22.8.

Example 16

Preparation of 11-methylisoplatensimycin (9)

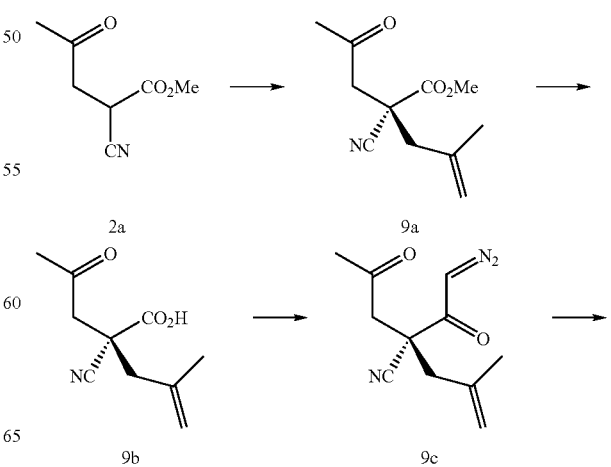

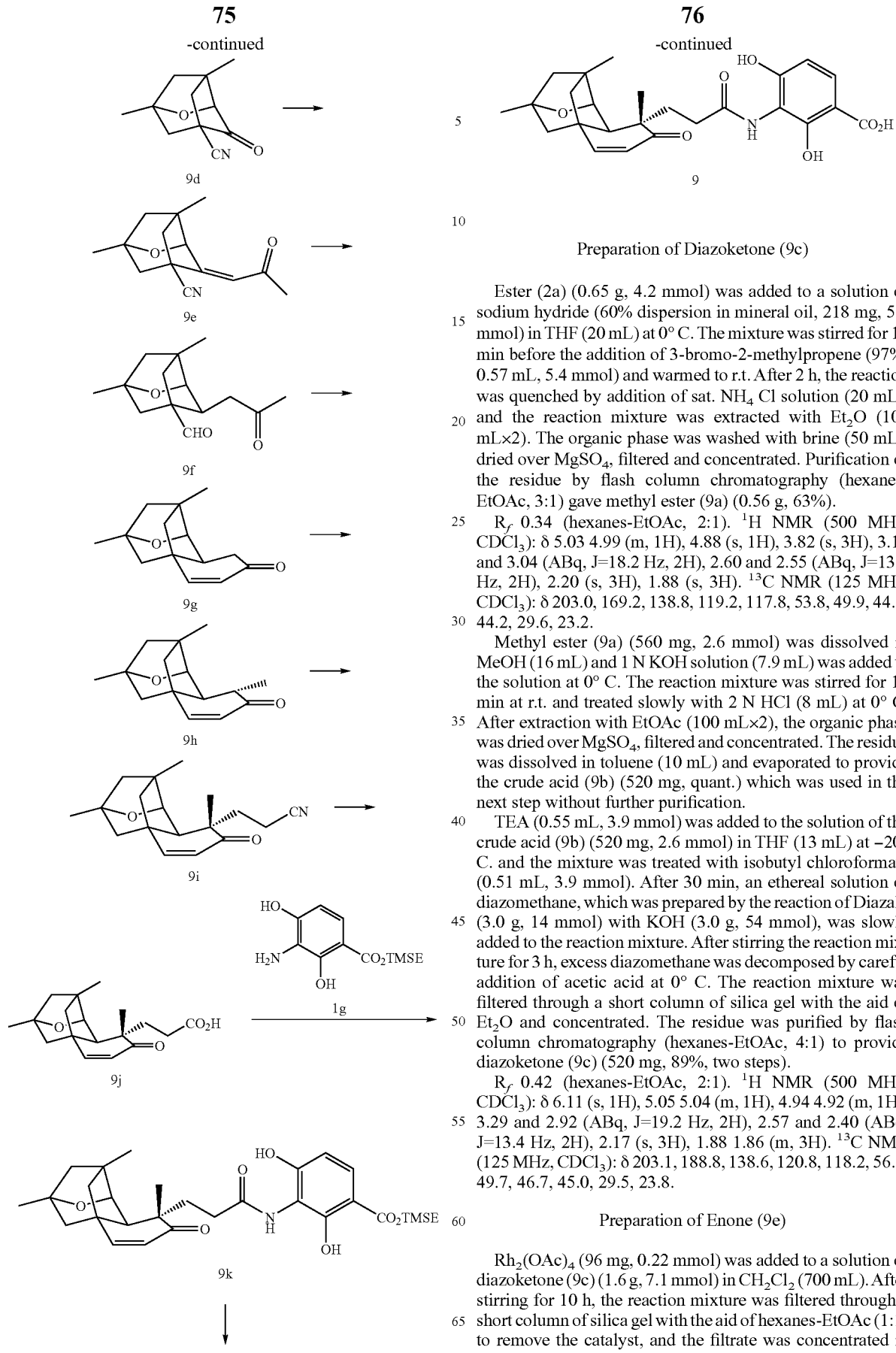

Preparation of Diazoketone (9c)

Ester (2a) (0.65 g, 4.2 mmol) was added to a solution of sodium hydride (60% dispersion in mineral oil, 218 mg, 5.4 mmol) in THF (20 mL) at 0° C. The mixture was stirred for 10 min before the addition of 3-bromo-2-methylpropene (97%, 0.57 mL, 5.4 mmol) and warmed to r.t. After 2 h, the reaction was quenched by addition of sat. NH$_4$Cl solution (20 mL), and the reaction mixture was extracted with Et$_2$O (100 mL×2). The organic phase was washed with brine (50 mL), dried over MgSO$_4$, filtered and concentrated. Purification of the residue by flash column chromatography (hexanes-EtOAc, 3:1) gave methyl ester (9a) (0.56 g, 63%).

R$_f$ 0.34 (hexanes-EtOAc, 2:1). $^1$H NMR (500 MHz, CDCl$_3$): δ 5.03 4.99 (m, 1H), 4.88 (s, 1H), 3.82 (s, 3H), 3.19 and 3.04 (ABq, J=18.2 Hz, 2H), 2.60 and 2.55 (ABq, J=13.5 Hz, 2H), 2.20 (s, 3H), 1.88 (s, 3H). $^{13}$C NMR (125 MHz, CDCl$_3$): δ 203.0, 169.2, 138.8, 119.2, 117.8, 53.8, 49.9, 44.9, 44.2, 29.6, 23.2.

Methyl ester (9a) (560 mg, 2.6 mmol) was dissolved in MeOH (16 mL) and 1 N KOH solution (7.9 mL) was added to the solution at 0° C. The reaction mixture was stirred for 10 min at r.t. and treated slowly with 2 N HCl (8 mL) at 0° C. After extraction with EtOAc (100 mL×2), the organic phase was dried over MgSO$_4$, filtered and concentrated. The residue was dissolved in toluene (10 mL) and evaporated to provide the crude acid (9b) (520 mg, quant.) which was used in the next step without further purification.

TEA (0.55 mL, 3.9 mmol) was added to the solution of the crude acid (9b) (520 mg, 2.6 mmol) in THF (13 mL) at −20° C. and the mixture was treated with isobutyl chloroformate (0.51 mL, 3.9 mmol). After 30 min, an ethereal solution of diazomethane, which was prepared by the reaction of Diazald (3.0 g, 14 mmol) with KOH (3.0 g, 54 mmol), was slowly added to the reaction mixture. After stirring the reaction mixture for 3 h, excess diazomethane was decomposed by careful addition of acetic acid at 0° C. The reaction mixture was filtered through a short column of silica gel with the aid of Et$_2$O and concentrated. The residue was purified by flash column chromatography (hexanes-EtOAc, 4:1) to provide diazoketone (9c) (520 mg, 89%, two steps).

R$_f$ 0.42 (hexanes-EtOAc, 2:1). $^1$H NMR (500 MHz, CDCl$_3$): δ 6.11 (s, 1H), 5.05 5.04 (m, 1H), 4.94 4.92 (m, 1H), 3.29 and 2.92 (ABq, J=19.2 Hz, 2H), 2.57 and 2.40 (ABq, J=13.4 Hz, 2H), 2.17 (s, 3H), 1.88 1.86 (m, 3H). $^{13}$C NMR (125 MHz, CDCl$_3$): δ 203.1, 188.8, 138.6, 120.8, 118.2, 56.1, 49.7, 46.7, 45.0, 29.5, 23.8.

Preparation of Enone (9e)

Rh$_2$(OAc)$_4$ (96 mg, 0.22 mmol) was added to a solution of diazoketone (9c) (1.6 g, 7.1 mmol) in CH$_2$Cl$_2$ (700 mL). After stirring for 10 h, the reaction mixture was filtered through a short column of silica gel with the aid of hexanes-EtOAc (1:1) to remove the catalyst, and the filtrate was concentrated in vacuo. The residue was purified by flash column chromatography (hexanes-acetone-$CH_2Cl_2$, 4:1:1) to provide ketone (9d) (1.0 g, 71%). $R_f$ 0.16 (hexanes-acetone-$CH_2Cl_2$, 4:1:1).

NaH (60% dispersion in mineral oil, 98 mg, 2.4 mmol) was added to a stirred suspension of anhydrous LiCl (139 mg, 3.2 mmol) and dimethyl 2-oxopropylphosphonate (0.25 mL, 1.8 mmol) in THF (15 mL) at 0° C. After 15 min, a solution of (9d) (320 mg, 1.6 mmol) in THF (2 mL) was added to the mixture and the reaction mixture was stirred for 15 h at r.t. before dilution with $Et_2O$ (100 mL). The organic phase was washed with brine (20 mL×2), dried over $MgSO_4$, filtered and concentrated. The residue was purified by flash column chromatography (hexanes-EtOAc, 4:1) to give enone (9e) (185 mg, 49%).

$R_f$ 0.39 (hexanes-EtOAc, 2:1). $^1H$ NMR (500 MHz, $CDCl_3$): δ 6.30 (s, 1H), 5.23 (s, 1H), 2.30 (s, 3H), 2.19 (dt, J=2.3, 12.7 Hz, 1H), 2.12 (d, J=10.6 Hz, 1H), 2.10 (d, J=12.7 Hz, 1H), 1.88 (d, J=11.2 Hz, 1H), 1.80 1.72 (m, 2H), 1.30 (s, 3H), 1.29 (s, 3H). $^{13}C$ NMR (125 MHz, $CDCl_3$): δ 197.7, 156.2, 118.7, 116.2, 81.4, 81.1, 53.0, 48.0, 47.3, 47.0, 44.3, 31.8, 22.8, 22.6.

Preparation of Aldehyde (9f)

Dimethylphenylsilane (0.080 mL, 0.52 mmol) was added to a solution of enone (9e) (62 mg, 0.26 mmol) and [Rh{(R,R)-Phebox-iPr}$(OAc)_2$]·$H_2O$ (2.8 mg, 0.0052 mmol) in toluene (0.5 mL) at r.t. The reaction mixture was stirred for 1 h at 60° C. and cooled to −40° C. After slow addition of DIBAL (1M in toluene, 1.1 mL, 1.1 mmol), the reaction mixture was stirred for 1 h and carefully quenched by addition of AcOH—$H_2O$ (1:1) solution (1.5 mL). The mixture was stirred vigorously at 0° C. for 1 h and diluted with EtOAc (15 mL). The mixture was washed with brine (5 mL×2), dried over $Na_2SO_4$, filtered and concentrated. This crude mixture was dissolved in THF (2 mL) before dropwise addition of 2 N HCl (0.1 mL) at 0° C. The mixture was stirred at 0° C. for 1 h and diluted with EtOAc (15 mL), washed with brine (5 mL), dried over $Na_2SO_4$, filtered and concentrated. The residue was purified by flash column chromatography (hexanes-acetone, 6:1) to give aldehyde (90 (45 mg, 73%).

$R_f$ 0.27 (hexanes-acetone, 3:1). $^1H$ NMR (500 MHz, $CDCl_3$): δ 9.50 (s, 1H), 3.81 (s, 1H), 2.73 (td, J=1.6, 6.8 Hz, 1H), 2.52 (dd, J=6.7, 17.8 Hz, 1H), 2.22 (dd, J=6.9, 17.8 Hz, 1H), 2.13 (s, 3H), 2.01 (dt, J=2.4, 12.3 Hz, 1H), 1.96 (dt, J=2.4, 12.8 Hz, 1H), 1.72 (d, J=10.8 Hz, 1H), 1.68 1.62 (m, 2H), 1.57 (dd, J=1.7, 12.3 Hz, 1H), 1.31 (s, 3H), 1.29 (s, 3H). $^{13}C$ NMR (125 MHz, $CDCl_3$): δ 206.4, 202.9, 90.3, 81.5, 58.6, 55.2, 47.8, 47.5, 43.5, 41.4, 40.5, 30.5, 24.0, 23.8.

Preparation of Cyclic Enone (9g)

p-TsOH monohydrate (10 mol %, 10 mg) was added to a solution of aldehyde (9f) (122 mg, 0.52 mmol) in toluene (10 mL) and the mixture was heated under reflux for 2 h with concomitant removal of water (Dean-Stark trap). After cooling to r.t., the mixture was diluted with $Et_2O$ (20 mL), washed with sat. $NaHCO_3$ solution (5 mL), dried over $MgSO_4$, filtered and concentrated. Flash column chromatography (hexanes-acetone, 8:1) provided cyclic enone (9g) (89 mg, 79%).

$R_f$ 0.36 (hexanes-acetone, 3:1). $^1H$ NMR (500 MHz, $CDCl_3$): δ 6.69 (d, J=10.0 Hz, 1H), 5.87 (d, J=10.0 Hz, 1H), 3.84 (s, 1H), 2.50 (dd, J=6.0, 18.3 Hz, 2H), 2.27 (dd, J=15.6, 18.5 Hz, 1H), 1.96 (dt, J=2.5, 12.2 Hz, 1H), 1.80 1.72 (m, 3H), 1.66 (ddt, J=2.3, 12.6, 15.0 Hz, 2H), 1.31 (s, 3H), 1.30 (s, 3H). $^{13}C$ NMR (125 MHz, $CDCl_3$): δ 198.2, 154.2, 128.8, 89.2, 82.0, 55.3, 54.0, 50.9, 49.7, 45.5, 45.1, 36.7, 24.0, 23.7.

Preparation of Enone (9h)

KHMDS (0.5 M solution in toluene, 0.60 mL, 0.30 mmol) was added to a solution of enone (9g) (33 mg, 0.15 mmol) in THF (3 mL) and HMPA (0.6 mL) at −78° C. The reaction mixture was allowed to stir at −78° C. for 30 min, after which MeI (0.075 mL, 1.2 mmol) was added. The reaction mixture was stirred at −10° C. for 1 h. The reaction mixture was quenched with sat. $NH_4Cl$ solution (2 mL) and extracted with ether (2×10 mL). The combined organic extracts were washed with brine (2×5 mL), dried over anhydrous $Na_2SO_4$, filtered and concentrated. The residue was purified by flash column chromatography (hexanes-acetone, 15:1) to give enone (9h) (30 mg, 86%).

$R_f$ 0.47 (hexanes-acetone, 3:1). $^1H$ NMR (500 MHz, $CDCl_3$): δ 6.63 (d, J=10.0 Hz, 1H), 5.86 (d, J=10.0 Hz, 1H), 3.99 (s, 1H), 2.31 (td, J=6.2, 12.9 Hz, 1H), 2.15 (d, J=13.4 Hz, 1H), 1.99 (d, J=12.1 Hz, 1H), 1.80 1.60 (m, 6H), 1.31 (s, 3H), 1.29 (s, 3H), 1.22 (d, J=6.6 Hz, 3H). $^{13}C$ NMR (125 MHz, $CDCl_3$): δ 200.5, 152.9, 128.4, 88.2, 82.0, 61.5, 55.4, 51.0, 50.0, 46.2, 45.4, 39.7, 23.9, 23.8, 12.7.

Preparation of Enone (9i)

Enone (9h) (35 mg, 0.15 mmol) was dissolved in t-BuOH (1.5 mL) and 40% KOH solution (0.0025 mL, 0.030 mmol) was added to the solution. The reaction mixture was allowed to stir at 60° C. for 5 min, after which acrylonitrile (0.072 mL, 1.1 mmol) was slowly added over 2 h at 60° C. The reaction mixture was stirred at 60° C. for 12 h. The reaction mixture was quenched with sat. $NH_4Cl$ solution (2 mL) and extracted with ether (2×10 mL). The combined organic extracts were washed with brine (2×5 mL), dried over anhydrous $Na_2SO_4$, filtered and concentrated. The residue was purified by flash column chromatography (hexanes-acetone, 8:1) to give enone (9i) (31 mg, 72%).

$R_f$ 0.42 (hexanes-acetone, 3:1). $^1H$ NMR (500 MHz, $CDCl_3$): δ 6.67 (d, J=10.1 Hz, 1H), 5.87 (d, J=10.1 Hz, 1H), 4.08 (s, 1H), 2.49 (ddd, J=5.0, 11.3, 16.4 Hz, 1H), 2.37 2.29 (m, 2H), 2.15 (ddd, J=5.2, 11.3, 13.9 Hz, 1H), 2.00 (dt, J=2.6, 12.3 Hz, 1H), 1.89 (ddd, J=5.0, 11.3, 13.9 Hz, 1H), 1.81 (d, J=10.7 Hz, 1H), 1.78 1.69 (m, 3H), 1.65 (dt, J=2.5, 12.7 Hz, 1H), 1.31 (s, 3H), 1.30 (s, 3H), 1.20 (s, 3H). $^{13}C$ NMR (125 MHz, $CDCl_3$): δ 201.7, 152.8, 127.7, 119.7, 87.9, 82.0, 60.6, 56.0, 51.2, 51.1, 47.3, 46.8, 44.7, 35.9, 24.2, 23.7, 22.3, 13.3.

Preparation of Carboxylic Acid (9j)

Enone (9i) (31 mg, 0.11 mmol) was dissolved in MeOH (0.9 mL) and 20% KOH solution (5.4 mL) was added to the solution. The reaction mixture was heated under reflux for 2 h. After cooling to r.t., the reaction mixture was treated with 2N HCl (15 mL) and extracted with EtOAc (50 mL×2). The combined organic extracts were washed with brine (2×20 mL), dried over anhydrous $Na_2SO_4$, filtered and concentrated. The residue was purified by flash column chromatography ($CHCl_3$-MeOH, 20:1) to give acid (9j) (27 mg, 82%).

$R_f$ 0.30 ($CHCl_3$-MeOH, 10:1). $^1H$ NMR (500 MHz, $CDCl_3$): δ 6.64 (d, J=10.1 Hz, 1H), 5.87 (d, J=10.0 Hz, 1H), 4.18 (s, 1H), 2.47 2.38 (m, 2H), 2.29 (ddd, J=5.0, 11.7, 16.5 Hz, 1H), 2.10 2.02 (m, 1H), 1.96 (dt, J=2.3, 12.2 Hz, 1H), 1.91 1.83 (m, 1H), 1.80 (d, J=10.8 Hz, 1H), 1.75 (dd, J=2.0, 12.2 Hz, 1H), 1.72 1.66 (m, 3H), 1.30 (s, 6H), 1.19 (s, 3H). $^{13}C$ NMR (125 MHz, $CDCl_3$): δ 202.6, 177.0, 152.5, 128.1, 88.2, 82.2, 60.2, 56.0, 51.7, 50.8, 47.2, 46.7, 44.8, 35.6, 29.5, 24.7, 23.6, 22.3.

Preparation of 11-methylisoplatensimycin TMSE ester (9k)

TEA (0.052 mL, 0.37 mmol) and HATU (112 mg, 0.28 mmol) were added to a solution of carboxylic acid (9j) (27 mg, 0.089 mmol) and aniline (1g) (77 mg, 0.28 mmol) in DMF (0.6 mL) at r.t. The reaction mixture was stirred at 24° C. for 15 h, after which brine (0.5 mL) was added. The resulting mixture was extracted with ether (4×10 mL), and the combined organic portions dried over $Na_2SO_4$. Concentration followed by flash column chromatography (hexanes-acetone, 7:1) afforded 11-methylisoplatensimycin TMSE ester (9k) (26 mg, 53%).

$R_f$ 0.34 (hexanes-acetone, 3:1). $^1$H NMR (500 MHz, $CDCl_3$): δ 11.81 (s, 1H), 10.98 (s, 1H), 7.97 (s, 1H), 7.55 (d, J=8.9 Hz, 1H), 6.67 (d, J=10.1 Hz, 1H), 6.50 (d, J=9.0 Hz, 1H), 5.90 (d, J=10.0 Hz, 1H), 4.44 4.40 (m, 2H), 4.15 (s, 1H), 2.65 (ddd, J=5.5, 11.2, 15.0 Hz, 1H), 2.50 2.41 (m, 2H), 2.20 (ddd, J=4.7, 11.1, 13.7 Hz, 1H), 2.05 1.97 (m, 2H), 1.81 (d, J=10.7 Hz, 1H), 1.77 1.64 (m, 4H), 1.32 (s, 3H), 1.28 (s, 3H), 1.23 (s, 3H), 1.16 1.11 (m, 2H), 0.10 (s, 9H). $^{13}$C NMR (125 MHz, $CDCl_3$): δ 202.6, 173.4, 170.6, 154.8, 153.9, 152.5, 127.8, 127.4, 114.4, 111.2, 104.4, 87.9, 81.7, 63.8, 60.5, 55.9, 51.1, 50.8, 47.2, 46.6, 45.0, 35.8, 32.6, 24.4, 23.5, 22.2, 17.4.

Preparation of 11-methylisoplatensimycin (9)

Tris(dimethylamino)sulfonium difluorotrimethylsilicate (26 mg, 0.094 mmol) was added to a stirred solution of 11-methylisoplatensimycin TMSE ester (9k) (26 mg, 0.047 mmol) in DMF (0.5 mL), and the mixture was heated at 40° C. for 50 min. The solution was then cooled to r.t. and brine (0.3 mL) added. The mixture was extracted with $CHCl_3$ (5×5 mL) and the combined organic portions dried over $Na_2SO_4$. Concentration followed by flash column chromatography (EtOAc:hexanes:MeOH:$H_2$O:AcOH, 60:40:0.6:0.3:0.3) afforded synthetic 11-methylisoplatensimycin (9) (15 mg, 70% yield).

$R_f$ 0.30 (EtOAc:hexanes:MeOH:$H_2$O:AcOH, 80:20:1:0.5: 0.5). $^1$H NMR (500 MHz, $CDCl_3$): δ 11.78 (s, 1H), 11.05 (s, 1H), 8.04 (s, 1H), 7.58 (d, J=8.9 Hz, 1H), 6.73 (d, J=10.0 Hz, 1H), 6.47 (d, J=8.9 Hz, 1H), 5.95 (d, J=10.0 Hz, 1H), 4.33 (s, 1H), 2.74 2.63 (m, 1H), 2.60 2.49 (m, 2H), 2.19 (td, J=3.6, 12.2 Hz, 1H), 2.11 2.00 (m, 2H), 1.89 1.74 (m, 5H), 1.36 (s, 3H), 1.34 (s, 3H), 1.26 (s, 3H). $^{13}$C NMR (125 MHz, $CDCl_3$): δ 203.4, 173.5, 172.7, 155.3, 154.4, 153.3, 128.4, 127.9, 114.4, 111.3, 103.9, 88.3, 83.1, 60.3, 55.9, 51.4, 51.0, 47.1, 46.8, 45.1, 36.4, 32.1, 24.5, 23.4, 22.3.

INDUSTRIAL APPLICABILITY

Platensimycin derivatives of the present invention retain the backbone structure of platensimycin known as an antibiotic but contain diverse substituents. The invention includes not only platensimycin derivatives but also isoplatensimycin and its derivatives, which are expected to have similar antibiotic activity to platensimycin. Platensimycin derivates, isoplatensimycin derivatives, platensimycin and isoplatensimycin can be synthesized, particularly mass-produced, in high yield and high purity but without side reactions by using the preparing method described in the present invention.

In addition, tetracyclo derivatives, the major intermediates for the production of platensimycin and its derivatives or isoplatensimycin and its derivatives can be synthesized in high purity and high yield from tricyclo ketone derivatives prepared by carbonyl ylide [3+2] cycloaddition according to the present invention.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. Platensimycin derivatives represented by formula 1;

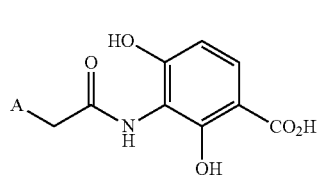

[Formula 1]

[In formula 1, A is

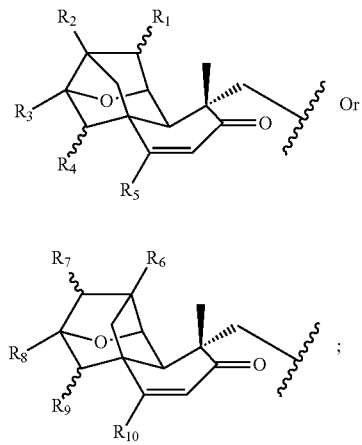

$R_1$ and $R_6$ are independently H, (C1-C10) alkyl, iodo, bromo or chloro;

$R_2$, $R_3$, $R_5$, $R_7$, $R_8$ and $R_{10}$ are independently H, (C1-C10) alkyl or (C6-C20) aryl;

$R_4$ and $R_9$ are independently H, (C1-C10) alkyl, (C6-C20) aryl or (C6-C20) aryl (C1-C10) alkyl;

But, it is excluded that $R_1$=$R_2$=$R_4$=$R_5$=H and $R_3$=methyl].

2. Platensimycin derivatives according to claim 1, wherein the platensimycin derivatives and isoplatensimycin derivatives are represented by formula 2 or formula 3;

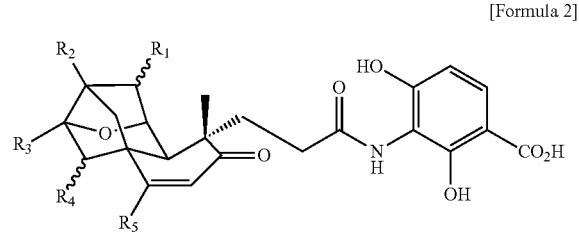

[Formula 2]

-continued

[Formula 3]

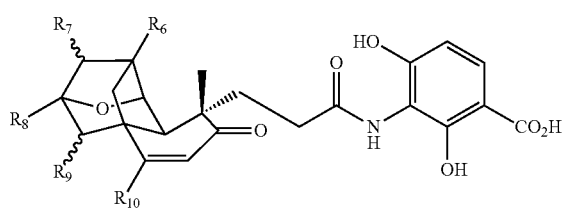

[R$_1$ and R$_6$ are independently H, methyl, ethyl, n-propyl, i-propyl, n-butyl, i-butyl, t-butyl, iodo, bromo or chloro; R$_2$, R$_3$, R$_7$ and R$_8$ are independently H, methyl, ethyl, n-propyl, i-propyl, n-butyl, i-butyl, t-butyl or phenyl; R$_4$ and R$_9$ are independently H, methyl, ethyl, n-propyl, i-propyl, n-butyl, i-butyl, t-butyl, phenyl or benzyl; R$_5$ and R$_{10}$ are independently H, methyl, ethyl, n-propyl, i-propyl, n-butyl, i-butyl, t-butyl or phenyl; but, it is excluded that R$_1$=R$_2$=R$_4$=R$_5$=H and R$_3$=methyl].

3. A preparing method of platensimycin and its derivatives represented by formula 2 comprising the following steps:

1) reacting enone derivative represented by formula 5 and acrylonitrile, leading to cyanoethylation to give enone derivative represented by formula 6;
2) hydrolyzing enone derivative represented by formula 6 to give carboxylic acid derivative represented by formula 7;
3) reacting carboxylic acid derivative represented by formula 7 and aniline derivative represented by formula 8, leading to amidation to give ester compound represented by formula 9; and
4) de-protecting the protection group of ester compound represented by formula 9 to give platensimycin and its derivatives represented by formula 2

[Formula 2]

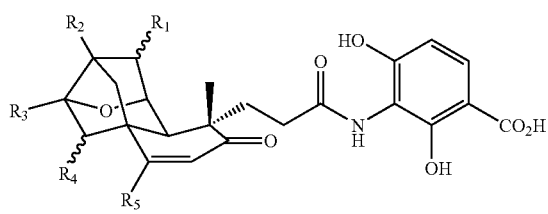

[Formula 5]

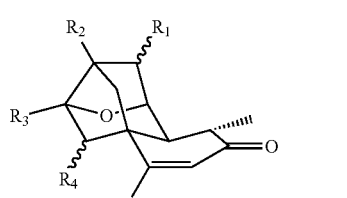

[Formula 6]

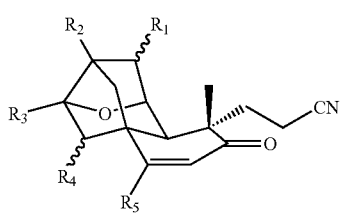

[Formula 7]

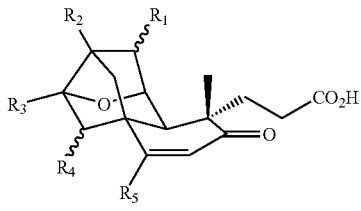

[Formula 8]

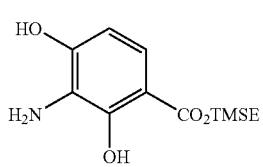

[Formula 9]

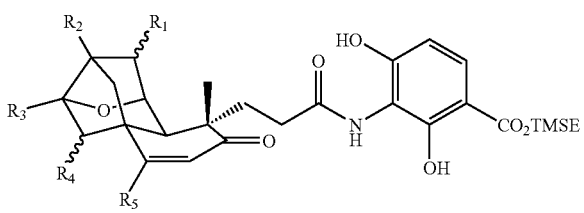

[In formulas 2, 5, 6, 7 and 9, R$_1$ is H, (C1-C10)alkyl, iodo, bromo or chloro; R$_2$, R$_3$ and R$_5$ are independently H, (C1-C10)alkyl or (C6-C20)aryl; R$_4$ is H, (C1-C10)alkyl, (C6-C20)aryl or (C6-C20)aryl(C1-C10)alkyl].

4. The preparing method of platensimycin and its derivatives represented by formula 2 according to claim 3, wherein the enone derivative represented by formula 5 is prepared by the following steps:

5) reacting tricyclo ketone derivative represented by formula 10 and dimethyl 2-oxopropylphosphonate to give enone compound represented by formula 11;
6) inducing hydrosilylation of enone compound represented by formula 11 in the presence of ruthenium(I) catalyst, which is reduced into diisobutylaluminum hydride or diisopropylaluminum hydride or reacted with organic lithium (R$_5$—Li; R$_5$=(C1-C10)alkyl or (C6-C20)aryl), followed by hydrolysis to give ketoaldehyde compound represented by formula 12;
7) inducing intramolecular condensation of ketoaldehyde compound represented by formula 12 to give tetracyclo derivative represented by formula 4; and
8) inducing methylation of tetracyclo derivative represented by formula 4 to give enone derivative represented by formula 5;

[Formula 5]

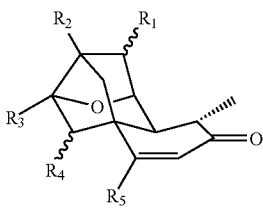

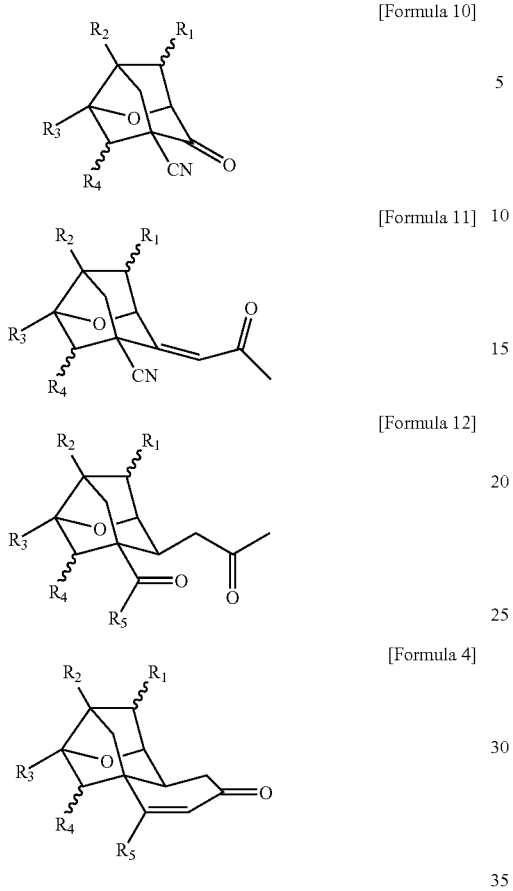

[In formulas 4, 5, 10, 11 and 12, $R_1$ is H, (C1-C10)alkyl, iodo, bromo or chloro; $R_2$, $R_3$ and $R_5$ are independently H, (C1-C10)alkyl or (C6-C20)aryl; $R_4$ is H, (C1-C10)alkyl, (C6-C20)aryl or (C6-C20)aryl(C1-C10)alkyl].

5. The method for producing platensimycin represented by formula 2 and its derivatives according to claim 3, wherein enone derivative represented by formula 5 is prepared by the following steps:

5-1) inducing dehalogenation of tricyclo ketone derivative represented by formula 10 to give the compound represented by formula 10-1;

5-2) reacting the compound represented by formula 10-1 with dimethyl 2-oxopropylphosphonate to give enone compound represented by formula 11-1;

6) inducing hydrosilylation of the compound represented by formula 10-1 in the presence of ruthenium(I) catalyst, followed by reducing thereof to diisobutylaluminum hydride or diisopropylaluminum hydride, or reacting the said compound with organic lithium (R5-Li; R5=(C1-C10)alkyl or (C6-C20)aryl), followed by hydrolyzing thereof to give the compound represented by formula 12-1;

7) inducing intramolecular condensation of the compound represented by formula 12-1 to give tetracyclo derivative represented by formula 4-1; and 8) inducing methylation of tetracyclo derivative represented by formula 4-1 to give enone derivative represented by formula 5-1;

[In formulas 4-1, 5-1, 10, 11-1 and 12-1, $R_1$ is iodo, bromo or chloro; $R_2$, $R_3$ and $R_5$ are independently H, (C1-C10)alkyl or (C6-C20)aryl; $R_4$ is H, (C1-C10)alkyl, (C6-C20)aryl or (C6-C20)aryl(C1-C10)alkyl].

6. The preparing method of platensimycin and its derivatives represented by formula 2 according to claim 3, wherein the enone derivative represented by formula 6, in which $R_5$ is (C1-C10)alkyl or (C6-C20)aryl, is prepared by the following steps:

9) reacting CuI and organic lithium ($R_5$—Li; $R_5$=(C1-C10)alkyl or (C6-C20)aryl), to which the compound represented by formula 6-1 and tri(C1-C10)alkylsilyl chloride are added to give the compound represented by formula 6-2; and 10) inducing oxidation and de-protection of the compound represented by formula 6-2 in the presence of DDQ (2,3-dichloro-5,6-dicyano-1,4-benzoquinone) and HMDS (hexamethyldisilazide) to give the compound represented by formula 6;

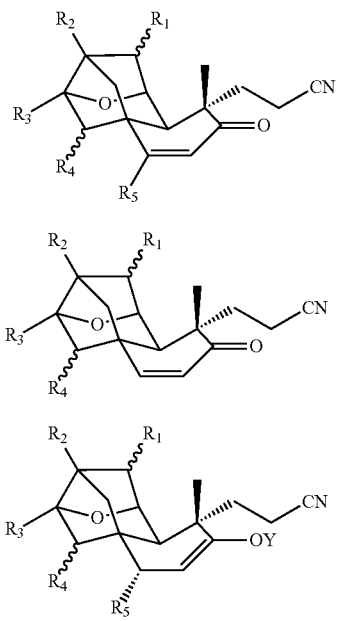

[Formula 6]

[Formula 6-1]

[Formula 6-2]

[In formulas 6, 6-1 and 6-2, $R_1$ is H, (C1-C10)alkyl, iodo, bromo or chloro; $R_2$ and $R_3$ are independently H, (C1-C10)alkyl or (C6-C20)aryl; $R_4$ is H, (C1-C10)alkyl, (C6-C20)aryl or (C6-C20)aryl(C1-C10)alkyl; $R_5$ is (C1-C10)alkyl or (C6-C20) aryl; Y is tri(C1-C10)alkylsilyl].

7. The preparing method of platensimycin and its derivatives represented by formula 2 according to claim 4, wherein the tricyclo ketone derivative represented by formula 10 is prepared by the following steps:

11) reacting the compound represented by formula 16 and allyl derivative represented by formula 17 in the presence of sodium hydride, followed by hydrolysis and reaction with diazomethane to give diazoketone derivative represented by formula 13; and 12) inducing carbonyl ylide [3+2] cycloaddition of diazoketone derivative represented by formula 13 in the presence of rhodium catalyst to give tricyclo ketone derivative represented by formula 10;

[Formula 10]

[Formula 16]

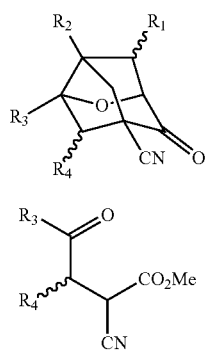

[Formula 17]

[Formula 13]

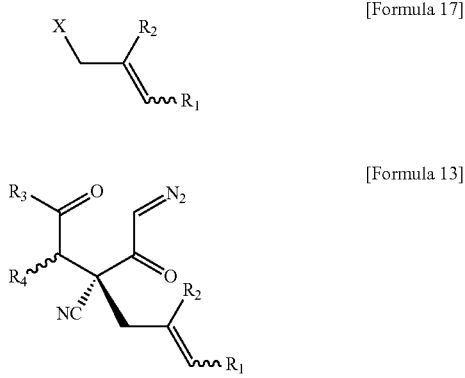

[In formulas 10, 13, 16 and 17, $R_1$ is (C1-C10)alkyl, iodo, bromo or chloro; $R_2$ and $R_3$ are independently H, (C1-C10)alkyl or (C6-C20)aryl; $R_4$ is H, (C1-C10)alkyl, (C6-C20)aryl or (C6-C20)aryl(C1-C10)alkyl; X is iodo, bromo or chloro].

8. A tricyclo ketone derivative represented by formula 10 or formula 24;

[Formula 10]

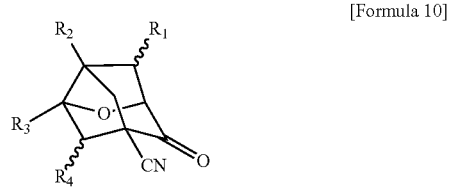

[Formula 24]

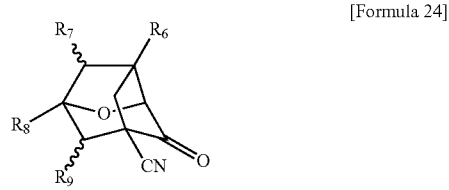

[In formulas 10 and 24, $R_1$ and $R_6$ are independently H, (C1-C10)alkyl, iodo, bromo or chloro; $R_2$, $R_3$, $R_7$ and $R_8$ are independently H, (C1-C10)alkyl or (C6-C20)aryl; $R_4$ and $R_9$ are independently H, (C1-C10)alkyl, (C6-C20)aryl or (C6-C20)aryl(C1-C10)alkyl].

9. A preparing method of tricyclo ketone derivative represented by formula 10 or formula 24 of claim 8, wherein the tricyclo ketone derivative represented by formula 10 or formula 24 is prepared by carbonyl ylide [3+2] cycloaddition of diazoketone derivative represented by formula 13 or formula 27 in the presence of rhodium catalyst;

[Formula 10]

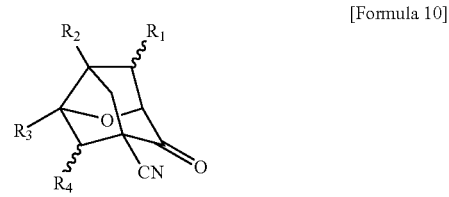

-continued

[Formula 24]

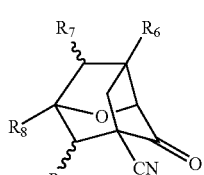

[Formula 13]

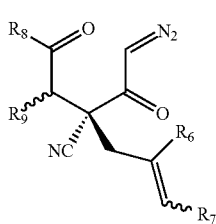

[Formula 27]

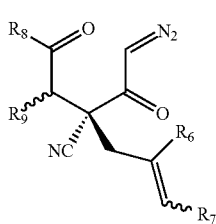

[In formulas 10, 13, 24 and 27, $R_1$ is (C1-C10)alkyl, iodo, bromo or chloro; $R_2$ and $R_3$ are independently H, (C1-C10)alkyl or (C6-C20)aryl; $R_4$ is H, (C1-C10)alkyl, (C6-C20)aryl or (C6-C20)aryl(C1-C10)alkyl; $R_6$ is H, (C1-C10)alkyl, iodo, bromo or chloro; $R_7$ and $R_8$ are independently H, (C1-C10)alkyl or (C6-C20)aryl; $R_9$ is H, (C1-C10)alkyl, (C6-C20)aryl or (C6-C20)aryl(C1-C10)alkyl].

10. A diazoketone derivative represented by formula 13 or formula 27;

[Formula 13]

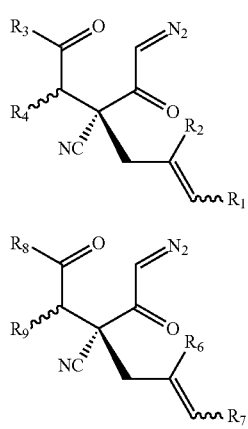

[Formula 27]

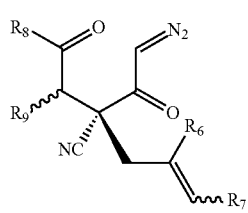

[In formula 13 and 27, $R_1$ is (C1-C10)alkyl, iodo, bromo or chloro; $R_2$ and $R_3$ are independently H, (C1-C10)alkyl or (C6-C20)aryl; $R_4$ is H, (C1-C10)alkyl, (C6-C20)aryl or (C6-C20)aryl(C1-C10)alkyl; $R_6$ is H, (C1-C10)alkyl, iodo, bromo or chloro; $R_7$ and $R_8$ are independently H, (C1-C10)alkyl or (C6-C20)aryl; $R_9$ is H, (C1-C10)alkyl, (C6-C20)aryl or (C6-C20)aryl(C1-C10)alkyl].

11. A preparing method of diazoketone derivative represented by formula 13 comprising the following steps:

13) reacting ethyl cyanoacetate represented by formula 14 and carbonyl chloride compound represented by formula 15 in the presence of sodium(C1-C10)alkoxide to give the compound represented by formula 16;

14) reacting the compound represented by formula 16 and allyl derivative represented by formula 17 in the presence of sodium hydride, followed by hydrolysis to give the compound represented by formula 18; and 15) reacting the compound represented by formula 18 and diazomethane to give diazoketone derivative represented by formula 13;

[Formula 13]

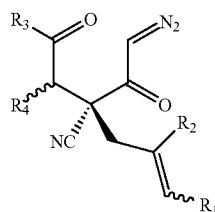

[Formula 14]

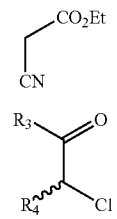

[Formula 15]

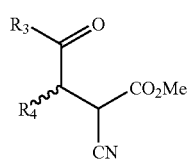

[Formula 16]

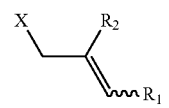

[Formula 17]

[Formula 18]

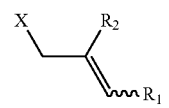

[In formulas 13 and 15 to 18, $R_1$ is (C1-C10)alkyl, iodo, bromo or chloro; $R_2$ and $R_3$ are independently H, (C1-C10)alkyl or (C6-C20)aryl; $R_4$ is H, (C1-C10)alkyl, (C6-C20)aryl or (C6-C20)aryl(C1-C10)alkyl; X is iodo, bromo or chloro].

12. A method for producing diazoketone derivative represented by formula 13 comprising the following steps:

13) reacting isopropyl 2-cyanoacetate, (S)-propyleneoxide derivative represented by formula C and allyl derivative represented by formula 17 stepwise in the presence of sodium hydride to give lactone compound represented by formula A;

14) reacting 2-methyl-2-propanethiol, the lactone compound represented by formula A prepared above and DMP (Dess-Martin periodinane) stepwise in the presence of trimethylaluminum to give thioester compound represented by formula B; and 15) hydrolyzing the thioester compound represented by formula B prepared above, followed by reaction with diazomethane to give diazoketone derivative represented by formula 13;

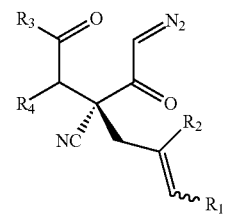
[Formula 13]

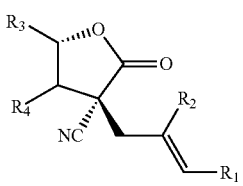
[Formula A]

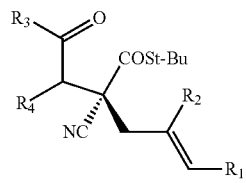
[Formula B]

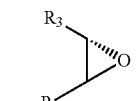
[Formula C]

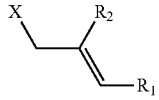
[Formula 17]

[In formulas 13, A, B, C and 17, $R_1$ is iodo, bromo or chloro; $R_2$ and $R_3$ are independently H, (C1-C10)alkyl or (C6-C20)aryl; $R_4$ is H, (C1-C10)alkyl, (C6-C20)aryl or (C6-C20)aryl(C1-C10)alkyl; X is iodo, bromo or chloro].

* * * * *

UNITED STATES PATENT AND TRADEMARK OFFICE
CERTIFICATE OF CORRECTION

PATENT NO. : 8,471,043 B2
APPLICATION NO. : 12/936856
DATED : June 25, 2013
INVENTOR(S) : Eun Lee et al.

It is certified that error appears in the above-identified patent and that said Letters Patent is hereby corrected as shown below:

In the Claims

Column 80, Line 50, Claim 1, delete "But" and insert -- but --

Column 81, Line 38, Claim 3, delete "2" and insert -- 2; --

Column 83, Line 57, Claim 5, delete "(R5-Li; R5" and insert -- ($R_5$-Li; $R_5$ --

Column 84, Line 51, Claim 5, after "10," insert -- 10-1, --

Signed and Sealed this
Twelfth Day of November, 2013

Teresa Stanek Rea
*Deputy Director of the United States Patent and Trademark Office*